(12) United States Patent
Kagawa et al.

(10) Patent No.: US 11,492,578 B2
(45) Date of Patent: Nov. 8, 2022

(54) MEMBRANE SEPARATION METHOD OF CELL SUSPENSION, AND CELL CULTURE DEVICE

(71) Applicant: FUJIFILM CORPORATION, Tokyo (JP)

(72) Inventors: Hideaki Kagawa, Kanagawa (JP); Yoichi Nagai, Kanagawa (JP); Shinichi Nakai, Kanagawa (JP); Souichi Kohashi, Kanagawa (JP); Toshiki Takei, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 381 days.

(21) Appl. No.: 16/219,872

(22) Filed: Dec. 13, 2018

(65) Prior Publication Data

US 2019/0112565 A1    Apr. 18, 2019

Related U.S. Application Data

(63) Continuation of application No. PCT/JP2017/021700, filed on Jun. 12, 2017.

(30) Foreign Application Priority Data

Jun. 30, 2016 (JP) ............................. JP2016-130579
May 12, 2017 (JP) ............................. JP2017-095673

(51) Int. Cl.
*C12M 3/02*     (2006.01)
*B01D 39/08*    (2006.01)
(Continued)

(52) U.S. Cl.
CPC .............. *C12M 3/02* (2013.01); *B01D 29/01* (2013.01); *B01D 39/08* (2013.01); *B01D 39/10* (2013.01);
(Continued)

(58) Field of Classification Search
None
See application file for complete search history.

(56) References Cited

U.S. PATENT DOCUMENTS 4,797,211 A * 1/1989 Ehrfeld ................. B01D 69/02
210/500.25
5,624,560 A 4/1997 Voll et al.
(Continued)

FOREIGN PATENT DOCUMENTS

CN    201061219 Y    5/2008
CN    102703319 A    10/2012
(Continued)

OTHER PUBLICATIONS

Zhou et al., Separable Bilayer Microfiltration Device for Viable Label-free Enrichment of Circulating Tumour Cells, Dec. 9, 2014, Scientific Reports 4:7392 (Year: 2014).*
(Continued)

*Primary Examiner* — Holly Kipouros
(74) *Attorney, Agent, or Firm* — Solaris Intellectual Property Group, PLLC

(57) ABSTRACT

The present disclosure provides a membrane separation method of a cell suspension which can appropriately separate cells from debris, and a cell culture device. That is, membrane separation processing of the cell suspension is performed using a filtration membrane which includes an inlet-side opening formed on one surface and an outlet-side opening, which is formed on the other surface and communicates with the inlet-side opening, and in which the inlet-side opening and the outlet-side opening are disposed at positions deviated in a direction parallel to the surfaces of the membrane.

24 Claims, 20 Drawing Sheets

(51) Int. Cl.
  B01D 39/10 (2006.01)
  B01D 39/14 (2006.01)
  B01D 29/01 (2006.01)
  C12M 1/00 (2006.01)
  C12M 3/06 (2006.01)
  C12M 1/26 (2006.01)
  C12N 5/078 (2010.01)

(52) U.S. Cl.
  CPC .............. *B01D 39/14* (2013.01); *C12M 3/06* (2013.01); *C12M 33/14* (2013.01); *C12M 47/02* (2013.01); *C12N 5/0644* (2013.01)

(56) References Cited

U.S. PATENT DOCUMENTS

| | | | |
|---|---|---|---|
| 6,309,546 | B1 | 10/2001 | Herrmann et al. |
| 2002/0074282 | A1 | 6/2002 | Herrmann et al. |
| 2011/0111412 | A1* | 5/2011 | Tai .................. B01D 61/18 435/6.14 |
| 2011/0233148 | A1* | 9/2011 | Antonchuk .......... G01N 1/4077 210/772 |
| 2013/0259772 | A1 | 10/2013 | Huang et al. |
| 2013/0288360 | A1 | 10/2013 | Jeon et al. |
| 2013/0327712 | A1 | 12/2013 | DelGiacco et al. |
| 2014/0190903 | A1* | 7/2014 | Huang ................ B01L 3/50255 210/323.1 |
| 2014/0217013 | A1 | 8/2014 | Sato et al. |
| 2014/0227784 | A1* | 8/2014 | Ejiri .................. C12M 23/12 435/402 |
| 2014/0335496 | A1* | 11/2014 | Grego ................ C12M 25/02 434/272 |
| 2015/0076049 | A1* | 3/2015 | Arya .................. G01N 1/4077 210/223 |
| 2015/0087016 | A1 | 3/2015 | Takagi |
| 2016/0002586 | A1* | 1/2016 | Mitchell ............. C12M 23/58 435/377 |
| 2016/0059576 | A1 | 3/2016 | Ito et al. |
| 2016/0144320 | A1 | 5/2016 | Nishino et al. |
| 2016/0252436 | A1 | 9/2016 | Jeon et al. |
| 2016/0263297 | A1* | 9/2016 | Suzuki ............... A61M 1/3496 |
| 2017/0306286 | A1 | 10/2017 | Ishii et al. |

FOREIGN PATENT DOCUMENTS

| | | |
|---|---|---|
| CN | 103189122 A | 7/2013 |
| CN | 103270151 A | 8/2013 |
| CN | 103484358 A | 1/2014 |
| CN | 103614298 A | 3/2014 |
| CN | 103270151 B | 1/2016 |
| JP | H04-142441 A | 5/1992 |
| JP | H07-021114 U | 4/1995 |
| JP | H09-253431 A | 9/1997 |
| JP | H10-10046 A | 1/1998 |
| JP | 2001-205011 A | 7/2001 |
| JP | 2001-252507 A | 9/2001 |
| JP | 2005-152849 A | 6/2005 |
| JP | 2007-181818 A | 7/2007 |
| JP | 2008-055359 A | 3/2008 |
| JP | 2009-261329 A | 11/2009 |
| JP | 2012-075802 A | 4/2012 |
| JP | 2012-139611 A | 7/2012 |
| JP | 2012-161790 A | 8/2012 |
| JP | 2013-42689 A | 3/2013 |
| JP | 2014-195757 A | 10/2014 |
| JP | 2015-87382 A | 5/2015 |
| JP | 2015-183064 A | 10/2015 |
| JP | 2016-022433 A | 2/2016 |
| JP | 2016-034614 A | 3/2016 |
| JP | 2016-049725 A | 4/2016 |
| WO | 1998/030315 A1 | 7/1998 |
| WO | 2005/095578 A1 | 10/2005 |
| WO | 2011139445 A1 | 11/2011 |
| WO | 2013/035747 A1 | 3/2013 |
| WO | 2014095959 A1 | 6/2014 |
| WO | 2014/204002 A1 | 12/2014 |
| WO | 2016/043163 A1 | 3/2016 |
| WO | 2016/047444 A1 | 3/2016 |
| WO | 2016117486 A1 | 7/2016 |

OTHER PUBLICATIONS

Lewis et al., Genomic landscapes of Chinese hamster ovary cell lines as revealed by the Cricetulus griseus draft genome, Aug. 2013, Nature Biotechnology, vol. 31 No. 8 (Year: 2013).*
Tao et al., Development and evaluation of a prototype non-woven fabric filter for purification of malaria-infected blood, 2011, Malaria Journal, 10:251 (Year: 2011).*
Wei et al., Particle sorting using a porous membrane in a microfluidic device, Lab on a Chip, Issue 2, 2011, pp. 238-245 (Year: 2011).*
Kelly et al., Understanding and Modeling Alternating Tangential Flow Filtration for Perfusion Cell Culture, 2014, American Institute of Chemical Engineers, published online in Wiley Online Library (wileyonlinelibrary.com) (Year: 2014).*
English language translation of the following: Office action dated Jun. 8, 2020 from the KIPO in a Korean patent application No. 10-2018-7037523 corresponding to the instant patent application. This office action translation is submitted now in order to supplement the understanding of the cited reference which is being disclosed in the instant Information Disclosure Statement.
A. Cencic et al., "Porcine blood cell separation by porous cellulose acetate membranes", Cytotechnology, vol. 26, No. 3, Mar. 1, 1998 (Mar. 1, 1998), Kluwer Academic Publishers, Netherlands, pp. 165-171.
Extended European Search Report dated Jun. 4, 2019, issued in corresponding EP Patent Application No. 17819840.4.
English language translation of the following: Office action dated Jun. 2, 2020 from the JPO in a Japanese patent application No. 2018-525021 corresponding to the instant patent application. This office action translation is submitted now in order to supplement the understanding of the cited references which are being disclosed in the instant Information Disclosure Statement.
International Search Report issued in International Application No. PCT/JP2017/021700 dated Aug. 29, 2017.
Written Opinion of the ISA issued in International Application No. PCT/JP2017/021700 dated Aug. 29, 2017.
English language translation of the following: Office action dated Nov. 5, 2019 from the JPO in a Japanese patent application No. 2018-525021 corresponding to the instant patent application.
Yoshiyuki Mori et al., "Hollow Fiber Module Applied for Effective Proliferation and Harvest of Cultured Chondrocytes", Materials Sciences and Applications, vol. 04, No. 08, Sep. 2013, pp. 62-67.
Office Action dated Jul. 1, 2021, issued by the EPO in corresponding EP Patent Application No. 17819840.4.
English language translation of the following: Office action dated Jul. 8, 2021 from the SIPO in a Chinese patent application No. 201780039579.4 corresponding to the instant patent application. This office action translation is submitted now in order to supplement the understanding of the cited references which are being disclosed in the instant Information Disclosure Statement.
English language translation of the following: Office action dated Dec. 29, 2021 from the SIPO in a Chinese patent application No. 201780039579.4 corresponding to the instant patent application. This office action translation is submitted now in order to supplement the understanding of the cited reference which is being disclosed in the instant Information Disclosure Statement.
English language translation of the following: Office action dated Mar. 31, 2022 from the SIPO in a Chinese patent application No. 201780039579.4 corresponding to the instant patent application.
English language translation of the following: Office action dated Aug. 8, 2022 from the SIPO in a Chinese patent application No. 201780039579.4 corresponding to the instant patent application.

* cited by examiner

SUBCULTURE PROCESSING

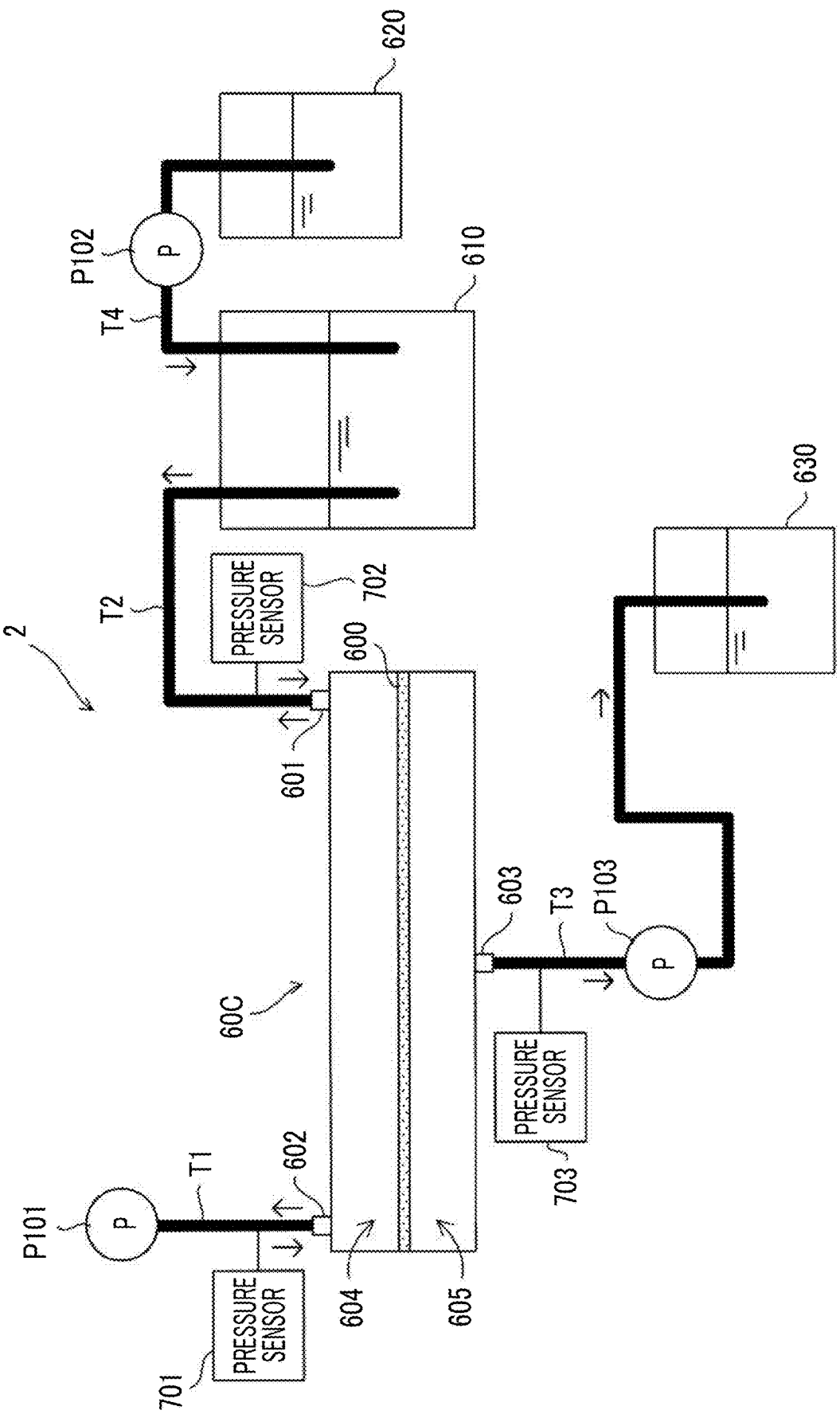

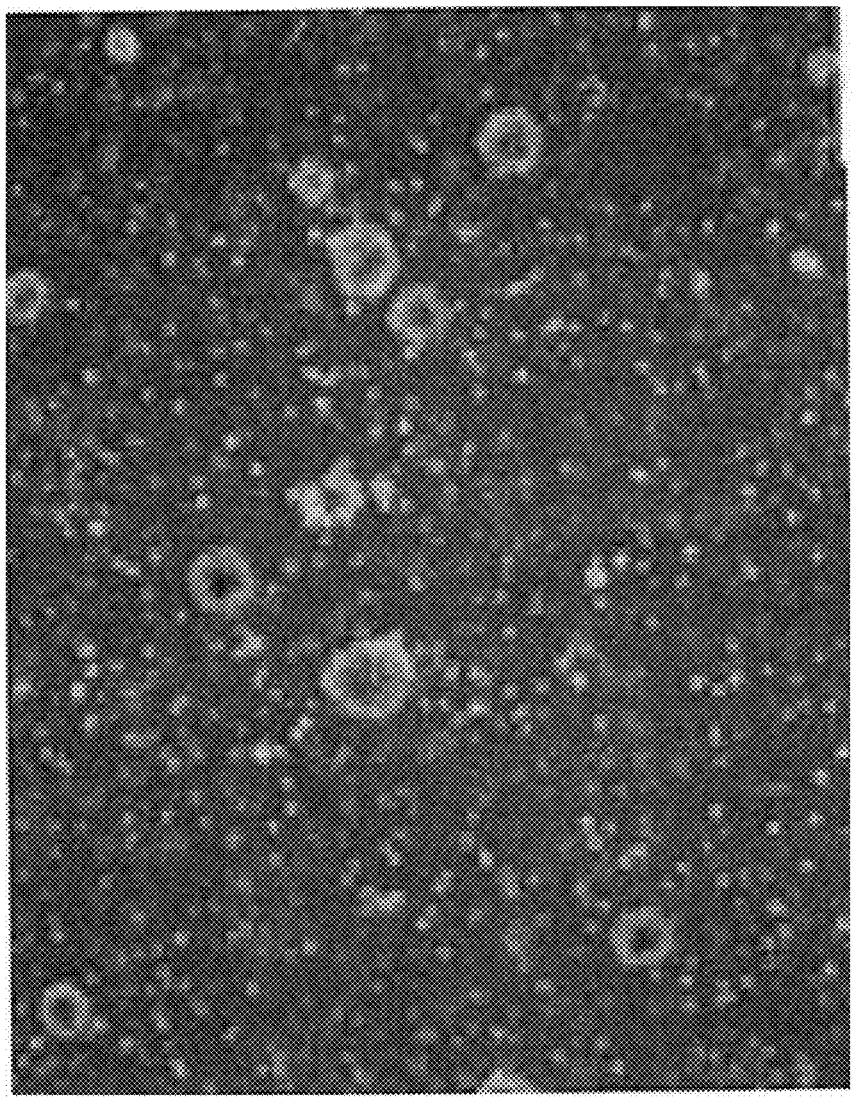
FIG. 18A  CELL SUSPENSION BEFORE MEMBRANE SEPARATION PROCESSING

CELL SUSPENSION AFTER MEMBRANE SEPARATION PROCESSING (EXAMPLE 3)

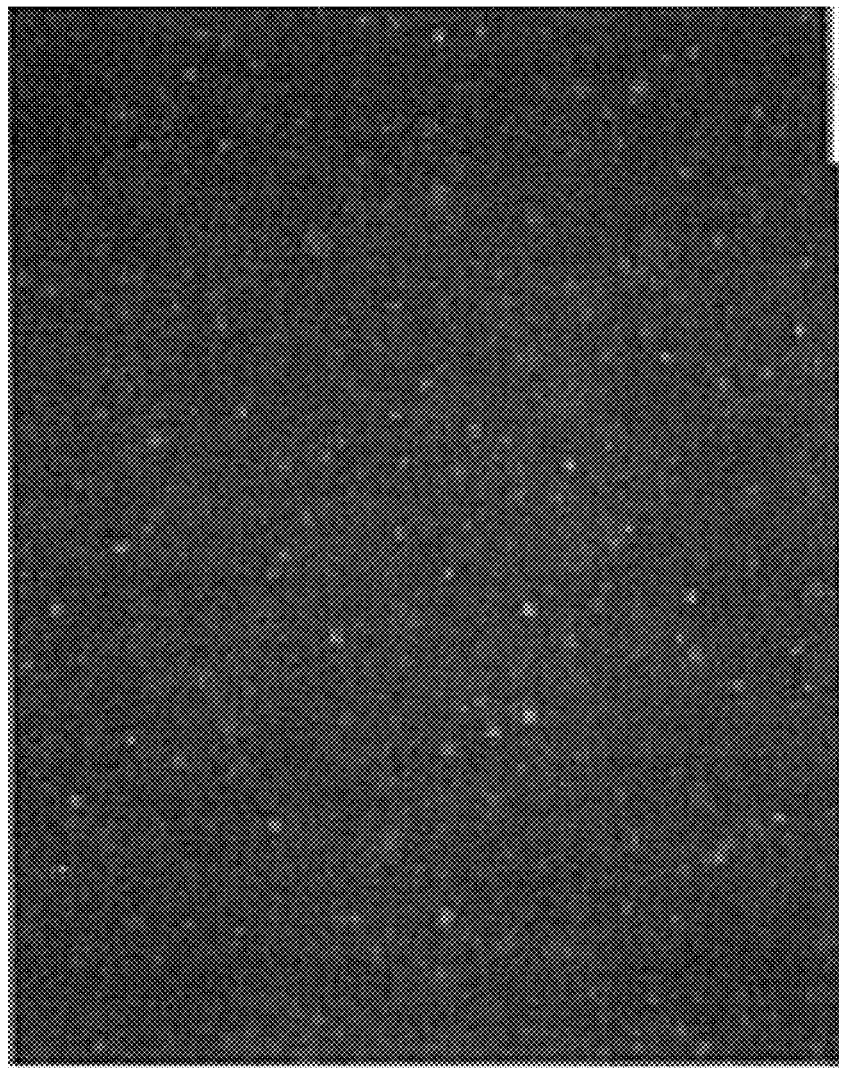
FIG. 18C FILTRATE AFTER MEMBRANE SEPARATION PROCESSING (EXAMPLE 3)

FIG. 18D  FILTRATE AFTER MEMBRANE SEPARATION PROCESSING (COMPARATIVE EXAMPLE 1)

MEMBRANE SEPARATION METHOD OF CELL SUSPENSION, AND CELL CULTURE DEVICE

CROSS-REFERENCE TO RELATED APPLICATIONS

This application is a continuation application of International Application No. PCT/JP2017/021700, filed on Jun. 12, 2017, which is incorporated herein by reference in its entirety. Further, this application claims priority from Japanese Patent Application No. 2016-130579, filed on Jun. 30, 2016, and from Japanese Patent Application No. 2017-095673, filed on May 12, 2017, the entire disclosures of which are incorporated by reference herein.

BACKGROUND

Technical Field

The present disclosure relates to a membrane separation method of a cell suspension and a cell culture device.

Related Art

The following techniques are known as techniques relating to membrane separation processing of a cell suspension using a filter. For example, JP2013-042689A discloses that cancer cells circulating in blood are captured using a cancer cell concentration filter which includes a metal substrate having a plurality of through-holes formed therein and in which opening shapes of the through-holes are rectangles or rounded rectangles having a length of a short side of 5.0 µm to 15.0 µm.

In addition, JP2015-087382A discloses that rare cells are separated from a blood specimen using a filter, which has elliptical holes having a minor axis diameter of 3.0 µm to 15 µm and a major axis diameter 1.1 to 3 times the minor axis diameter with a hole density of 200 holes/mm$^2$ to 40,000 holes/mm$^2$, by filtering the blood specimen so that the filtering capacity of a filter becomes less than or equal to 6 µl/hole in terms of blood.

In culturing of cells, membrane separation processing in which debris such as dead cells, crushed cells, and cell secretions are removed from a cell suspension using a filtration membrane (filter) having a plurality of openings is performed during medium replacement processing performed during a culture period. However, in the membrane separation processing in which the filtration membrane in the related art is used, clogging in which the openings of the filtration membrane are blocked by debris occurs, and therefore, there is a possibility that the debris cannot be appropriately discharged. In addition, in a case where the filtration membrane is clogged, the pressure of the cell suspension coming into contact with the filtration membrane increases, and therefore, there is a possibility that cells may be damaged. In a case where an opening diameter of the filtration membrane is increased in order to prevent the clogging in the filtration membrane, cells to be collected also permeate through the filtration membrane together with the debris.

In addition, membrane separation processing in which debris such as dead cells, crushed cells, and cell secretions, and single cells are removed using a filtration membrane (filter) having a plurality of openings is performed on cells forming aggregations of cells (hereinafter, referred to as cell aggregations) called spheres such as embryonic stem cells (ES cells) and induced pluripotent stem cells (iPS cells). However, in the membrane separation processing in which the filtration membrane in the related art is used, clogging in which the openings of the filtration membrane are blocked by debris and single cells occurs, and therefore, there is a possibility that the debris and the single cells cannot be appropriately discharged. In addition, in a case where the filtration membrane is clogged, the pressure of the cell suspension coming into contact with the filtration membrane increases, and therefore, there is a concern that cells may be damaged. In a case where an opening diameter of the filtration membrane is increased in order to prevent the clogging in the filtration membrane, cell aggregations to be collected also permeate through the filtration membrane together with the debris and single cells.

SUMMARY

The present disclosure provides a membrane separation method of a cell suspension which can appropriately separate cell aggregations from single cells and debris (such as dead cells, crushed cells, and cell secretions) which have smaller diameters than those of the cell aggregations, and a cell culture device.

In addition, the present disclosure also provides a membrane separation method of a cell suspension which can appropriately separate single cells from debris (such as dead cells, crushed cells, and cell secretions) having smaller diameters than those of the single cells, and a cell culture device.

According to a first aspect of the present disclosure, there is provided a membrane separation method of a cell suspension for performing membrane separation processing of the cell suspension using a filtration membrane which includes an inlet-side opening formed on a first surface and an outlet-side opening, which is formed on a second surface on an opposite side of the first surface and communicates with the inlet-side opening, and in which the inlet-side opening and the outlet-side opening are disposed at positions deviated in a direction parallel to the surfaces of the membrane.

According to a second aspect of the present disclosure, there is provided a membrane separation method of a cell suspension for performing membrane separation processing of the cell suspension using a filtration membrane which includes an inlet-side opening formed on a first surface and an outlet-side opening, which is formed on a second surface on an opposite side of the first surface and communicates with the inlet-side opening, and in which a path connecting the inlet-side opening to the outlet-side opening is nonlinear.

In a third aspect according to the present disclosure, in a case where the cell suspension of the above-described aspects contains a cell aggregation, a single cell, and debris, the membrane separation method according to the present disclosure may include separating the cell aggregation from the single cell and the debris using the filtration membrane in the membrane separation processing.

In a fourth aspect according to the present disclosure, in a case where the cell suspension of the above-described aspects contains a single cell and debris, the membrane separation method according to the present disclosure may include separating the single cell from the debris using the filtration membrane in the membrane separation processing.

In a fifth aspect according to the present disclosure, it is preferable that a diameter of the inlet-side opening of the filtration membrane of the above-described third aspect is 0.01 to 3.0 times a diameter of the cell aggregation.

In a sixth aspect according to the present disclosure, it is preferable that, in a case where the single cell of the above-described fourth aspect is a human-derived cell, a diameter of the inlet-side opening of the filtration membrane is 0.05 to 0.8 times a diameter of the single cell.

In a seventh aspect according to the present disclosure, it is preferable that, in a case where the single cell of the above-described fourth aspect is a non-human cell, a diameter of the inlet-side opening of the filtration membrane is 0.1 to 2 times a diameter of the single cell.

In an eighth aspect according to the present disclosure, it is preferable that, in a case where the single cell of the above-described fourth and seventh aspects is a non-human cell, $0<\sigma/X\leq 0.1$ is satisfied, where an average value of opening diameter distribution of the filtration membrane is set to X and a standard deviation is set to $\sigma$.

In a ninth aspect according to the present disclosure, it is preferable that, in a case where the single cell of the above-described fourth, seventh, and eighth aspects is a non-human cell, a thickness of the filtration membrane is less than or equal to 150 μm.

In a tenth aspect according to the present disclosure, it is preferable that, in a case where the single cell of the above-described fourth and seventh to ninth aspects is a non-human cell, a gauge pressure applied to the first surface of the filtration membrane is −70 kilopascals to 70 kilopascals.

In an eleventh aspect according to the present disclosure, it is preferable that, in a case where the single cell of the above-described fourth and seventh to tenth aspects is a non-human cell, a number density of the single cell contained in a filtrate that has permeated through the filtration membrane is less than or equal to 50% of a number density of the single cell contained in the cell suspension before permeating through the filtration membrane.

In a twelfth aspect according to the present disclosure, it is preferable that, in a case where the single cell of the above-described fourth and seventh to eleventh aspects is a non-human cell, a number density of debris which has a diameter of 1/10 to 1/2 of the diameter of the single cell and is contained in the filtrate that has permeated through the filtration membrane is 50% to 100% of a number density of debris which has a diameter of 1/10 to 1/2 of the diameter of the single cell and is contained in the cell suspension before permeating through the filtration membrane.

In a thirteenth aspect according to the present disclosure, it is preferable that, in a case where the single cell of the above-described fourth and seventh to twelfth aspects is a non-human cell, the diameter of the single cell is 5 μm to 25 μm.

In a fourteenth aspect according to the present disclosure, the single cell of the above-described fourth and seventh to thirteenth aspects may be a CHO cell.

In a fifteenth aspect according to the present disclosure, the cell aggregation of the above-described third aspect may be an aggregation of human-derived cells, and the single cell may be a human-derived cell.

In the sixteenth to nineteenth aspects according to the present disclosure, in a case where the cell aggregation or the single cell of the above-described sixth and fifteenth aspects contains a human-derived cell, the human-derived cell may be a stem cell or a megakaryocyte.

In a twentieth aspect according to the present disclosure, the membrane separation processing of the above-described aspects may be performed by setting a difference between the pressure applied to the first surface of the filtration membrane and a pressure applied to the second surface of the filtration membrane to 0.01 kilopascals to 60 kilopascals.

In a twenty-first aspect according to the present disclosure, the membrane separation processing of the above-described aspects may be performed using the filtration membrane whose surfaces have been subjected to hydrophilic treatment.

In a twenty-second aspect according to the present disclosure, the filtration membrane of the above-described aspects may be configured to include a mesh formed by twill-weaving a fibrous member. In addition, in a twenty-third aspect of the present disclosure, the mesh may be configured to contain metal.

In a twenty-fourth aspect according to the present disclosure, the filtration membrane of the above-described first to twenty-first aspects may be suitably used which is configured by laminating a plurality of meshes, each of which has through-holes, while deviating the positions of the through-holes to each other in a direction parallel to the surfaces of the filtration membrane. In addition, a plurality of the meshes of the twenty-third aspect of the present disclosure may be configured to contain metal.

In a twenty-fifth aspect according to the present disclosure, the membrane separation processing of the above-described aspects may be performed by allowing the cell suspension to flow along a direction of the surfaces of the filtration membrane. In a twenty-sixth aspect according to the present disclosure, the membrane separation processing of the above-described twenty-fifth aspect may be performed by reciprocating the cell suspension along the surfaces of the filtration membrane.

According to a twenty-seventh aspect of the present disclosure, there is provided a membrane separation method for performing membrane separation processing of a cell suspension supplied from a culture container for culturing cells, using a filtration membrane, in which an inlet-side opening formed on a first surface and an outlet-side opening which is formed on a second surface on an opposite side of the first surface and communicates with the inlet-side opening are disposed at positions deviated in a direction parallel to the surfaces of the membrane, of a cell culture device including the culture container and a filtration portion which includes the filtration membrane and is connected to the culture container via a flow path in which cells cultured in the culture container circulate, in which $0.1 \leq N/L \leq 6$ is satisfied when the amount of the cell suspension in the culture container is set to L and the amount of a filtrate per day which has permeated through the filtration membrane in the membrane separation processing is set to N.

According to a twenty-eighth aspect of the present disclosure, there is provided a cell culture device comprising: a culture container for culturing cells; and a filtration portion which includes a filtration membrane connected to the culture container via a flow path in which cells cultured in the culture container circulate. The filtration portion includes a filtration membrane including an inlet-side opening formed on a first surface and an outlet-side opening which is formed on a second surface on an opposite side of the first surface and communicates with the inlet-side opening. The inlet-side opening and the outlet-side opening of the filtration membrane are disposed at positions deviated in a direction parallel to the surfaces of the filtration membrane.

According to a twenty-ninth aspect of the present disclosure, there is provided a cell culture device comprising: a culture container for culturing cells; and a filtration portion which includes a filtration membrane connected to the culture container via a flow path in which cells cultured in the culture container circulate. The filtration portion includes a filtration membrane including an inlet-side opening formed on a first surface and an outlet-side opening which is formed on a second surface on an opposite side of the first surface and communicates with the inlet-side opening. A path connecting the inlet-side opening to the outlet-side opening of the filtration membrane is nonlinear.

In a thirtieth aspect according to the present disclosure, the surfaces of the filtration membrane of the above-described twenty-eighth and twenty-ninth aspects may be subjected to hydrophilic treatment.

In a thirty-first aspect according to the present disclosure, the filtration membrane of the above-described twenty-eighth to thirtieth aspects may be configured to include a mesh formed by twill-weaving a fibrous member.

In a thirty-second aspect according to the present disclosure, the filtration membrane of the above-described twenty-eighth to thirtieth aspects may be configured by laminating a plurality of meshes having through-holes while deviating the positions of the through-holes to each other in a direction parallel to the surfaces of the filtration membrane.

According to the above-described aspects of the present disclosure, it is possible to separate cell aggregations from single cells and debris (such as dead cells, crushed cells, cell wastes, and proteins secreted from cells) which have smaller diameters than those of the cell aggregations while reducing damage to the cells.

In addition, according to the above-described aspects of the present disclosure, it is possible to separate single cells from single cells and debris (such as dead cells, crushed cells, cell wastes, and proteins secreted from cells) which have smaller diameters than those of the single cells while reducing damage to the cells.

BRIEF DESCRIPTION OF THE DRAWINGS

FIG. 17 is a view showing an example of a configuration of a cell culture device according to another exemplary embodiment of the present disclosure.

FIG. 18A is a micrograph of a cell suspension before membrane separation processing.

FIG. 18C is a micrograph of a filtrate discharged to a permeation side after membrane separation processing is performed under the condition of Example 1-1 in Table 1.

FIG. 18D is a micrograph of a filtrate discharged to a permeation side after membrane separation processing is performed under a condition of Comparative Example 1-1 in Table 1.

DESCRIPTION OF EMBODIMENTS

Figure 1:
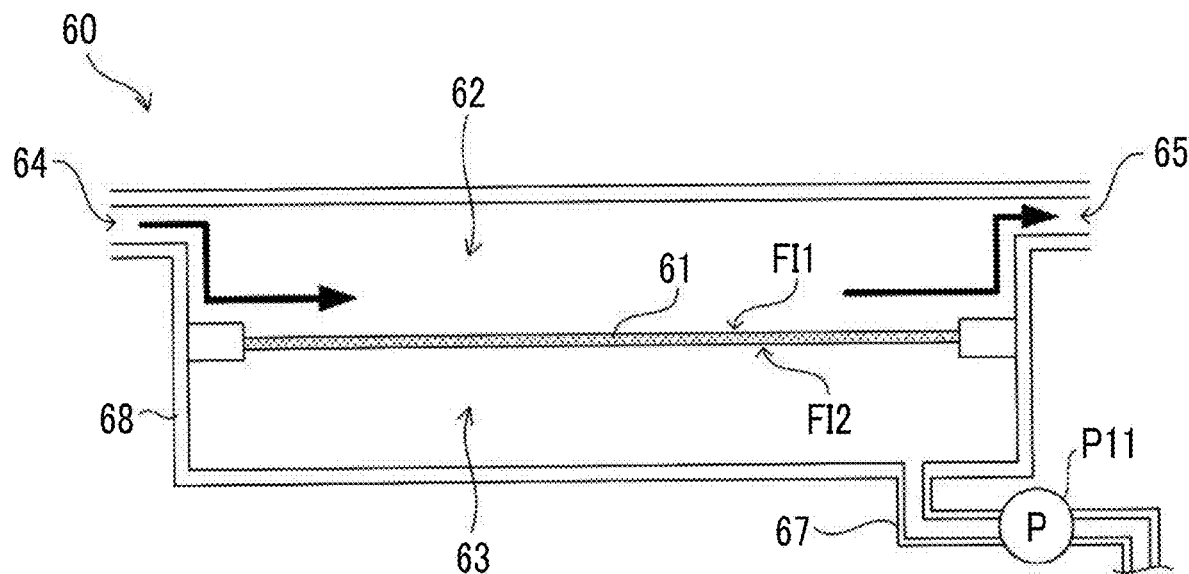
FIG. 1 is a view showing a schematic configuration of a filtration device according to exemplary embodiments of the present disclosure.

Hereinafter, an example of exemplary embodiments of the present disclosure will be described with reference to the drawings. The same reference numerals will be given to the same or equivalent constituent elements and portions in each drawing, and the description thereof will not be repeated.

First Exemplary Embodiment

A subject on which membrane separation processing is performed by a membrane separation method according to an exemplary embodiment of the present disclosure is, for example, a cell suspension containing at least one of single cells and cell aggregations.

The "cells" are not particularly limited as long as these are suitable for culture, and examples thereof include animal cells, insect cells, and yeast. Human cells or non-human animal cells are preferable as cells to which the membrane separation method according to the exemplary embodiment of the present disclosure is applied.

The human cells are not particularly limited as long as these are human-derived cells or tissues, and examples thereof include human ectodermal cells, human mesodermal cells, human endodermal cells, cells involved in a process of differentiation from a human embryo into these cells, human embryonic stem cells, and human somatic stem cells. Specific examples thereof include myoblasts; mesenchymal stem cells (derived from bone marrow, adipose tissues, peripheral blood, skin, hair roots, muscle tissues, endometrium, placenta, or umbilical cord blood); cardiomyocytes; fibroblasts; cardiac stem cells; pluripotent stem cells such as embryonic stem cells (ES cells), induced pluripotent stem cells (iPS cells), multilineage-differentiating stress enduring cells (Muse cells), embryonal carcinoma cells (EC cells), and embryonic germ cells (EG cells); pluripotent stem cell-derived cells; nasal mucosal epithelial cells; retinal pigment epithelial cells; synovial cells; chondrocytes; hepatocytes; kidney cells; adrenal cells; pancreatic cells such as islet cells; epithelial cells such as oral mucosal epithelial cells and endothelial cells; periodontal ligament cells; gingival cells; periosteal cells; skin cells; hematopoietic cells such as megakaryocytes; and blood cells such as platelets. Pluripotent stem cells, pluripotent stem cell-derived cells, megakaryocytes, and platelets are preferable and induced pluripotent stem cells (iPS cells) are more preferable.

The "pluripotent stem cell-derived cells" are not limited as long as these are cells derived from pluripotent stem cells, and an example thereof include differentiated cells.

The "differentiated cells" mean daughter cells having specific functional or morphological characteristics generated by differentiation of pluripotent stem cells. Differentiated cells are usually stable, proliferation potential thereof is low, and differentiation into other types of cells only exceptionally occurs.

The "non-human animal cells" are not particularly limited as long as these are animal cells other than human cells, and examples thereof include CHO cells derived from Chinese hamster ovary; BHK cells derived from baby hamster kidneys; HeLa cells derived from human cervical cancer; C-127 cells derived from mouse breast cancer; NIH/3T3 and BALB3T3 which are mouse fibroblast cells; VerotsS3 cells derived from African green monkey kidneys; mouse cell lines NS0 (ATCC CRL-1827) and SP2/0 (ATCC CRL-1581); SP2/0-Ag14 cells derived from mouse myelomas; Y3 Ag 1.2.3 cells (ATCC CRL-1631), YO cells (ECACC No: 85110501), YB2/3HL.P2.G11.16Ag.20 cells, and YB2/0 cells (ATCC CRL-1662) derived from rat myelomas; and BHK-21 cells (ATCC CCL-10) and MDCK (ATCC CCL-34) derived from Syrian hamster kidney tissues. CHO cells, BHK-21 cells, and SP2/0-Ag14 cells are preferable and CHO cells are more preferable.

In a case where the membrane separation method according to the exemplary embodiment of the present disclosure is used for separating cell aggregations from single cells and debris, human cells are preferable, human-derived pluripotent stem cells and human pluripotent stem cell-derived cells are more preferable, and human-derived induced pluripotent stem cells (hiPS cells) are still more preferable.

In a case where the membrane separation method according to the exemplary embodiment of the present disclosure is used for separating of single cells from debris, human cells or non-human cells are preferable, and human-derived induced pluripotent stem cells (hiPS cells), megakaryocytes, platelets, CHO cells, BHK-21 cells, and SP2/0-Ag14 cells are more preferable. In another aspect, non-human cells are preferable, CHO cells, BHK-21 cells, and SP2/0-Ag14 cells are more preferable, and CHO cells are still more preferable.

The membrane separation method according to the exemplary embodiment of the present disclosure can also be used for separating megakaryocytes (single cells) from platelets (debris) which are secretions of megakaryocytes.

The "cell aggregations" are aggregations of cells and are also called spheres.

The "single cells" mean individual cells that have not formed aggregations.

Examples of the "debris" include dead cells, crushed cells, and cell secretions.

Examples of the "cell secretions" include wastes of cells, proteins secreted from cells, and cells (for example, platelets) which are secreted from cells and different from the above-described cells.

Megakaryocyte precursor cells or megakaryoblast cells are included in the "megakaryocytes" in addition to mature megakaryocytes. The "megakaryocytes" may be megakaryocytes differentiated from cells having differentiation potency of pluripotent stem cells, hematopoietic precursor cells, mesenchymal cells, or the like, in addition to megakaryocytes collected from adult tissues.

FIG. 1 is a schematic diagram showing a configuration of a filtration device 60 that performs the membrane separation method of a cell suspension according to the exemplary embodiment of the present disclosure. The filtration device 60 is a device that performs membrane separation processing of a cell suspension in which cell aggregations contained in the cell suspension are separated from single cells and debris (such as dead cells, crushed cells, cell wastes, and proteins secreted from cells) which do not form a cell aggregation, using a filtration membrane 61. In addition, the filtration device 60 can also be used in a case of performing membrane separation processing for separating single cells from debris using the filtration membrane 61. The filtration device 60 can be used, for example, in medium replacement processing or the like for replacing a used medium containing debris used for cell culture with a fresh medium.

The filtration device 60 comprises a container 68 and the filtration membrane 61 separating the space inside the container 68 into a supply side 62 and a permeation side 63. In addition, the filtration device 60 includes an inflow port 64 into which a cell suspension flows and an outflow port 65 through which the cell suspension flows out, on the supply side 62. The cell suspension to be subjected to membrane separation processing passes through the filtration membrane 61 while flowing into the container 68 from the inflow port 64 and flowing out of the container 68 from the outflow port 65. Components which are contained in the cell suspension and have relatively small sizes permeate through the filtration membrane 61 together with a liquid such as a medium and are discharged to the permeation side 63. For example, in a case of separating the cell aggregations from single cells and debris using the filtration device 60, the single cells and the debris having smaller sizes than those of the cell aggregations permeate through the filtration membrane 61 and are discharged to the permeation side 63. In addition, in a case of separating single cells from debris using the filtration device 60, the debris having smaller sizes than those of the single cells permeate through the filtration membrane 61 and are discharged to the permeation side 63. A discharge flow path 67 provided with a pump P11 is connected to the permeation side 63 of the container 68, and the components discharged to the permeation side 63 are collected in a waste liquid collection container (not shown in the drawing) via the discharge flow path 67. On the other hand, components (cell aggregations or single cells) which are contained in the cell suspension and have relatively large sizes do not permeate through the filtration membrane 61, but flow out of the container 68 from the outflow port 65 and are collected. In this manner, it is possible to perform filtration in the filtration device 60 through a cross-flow (tangential flow) method in which a cell suspension is subjected to membrane separation processing flows along the surface of the filtration membrane 61. By performing the filtration through the cross-flow method in this manner, it is possible to suppress clogging in the filtration membrane 61 compared to a case of performing the filtration through a dead-end method. As a result, it is possible to suppress pressure increase on the supply side 62 during the membrane separation processing and to reduce damage to cells during the membrane separation processing.

Figure 2:
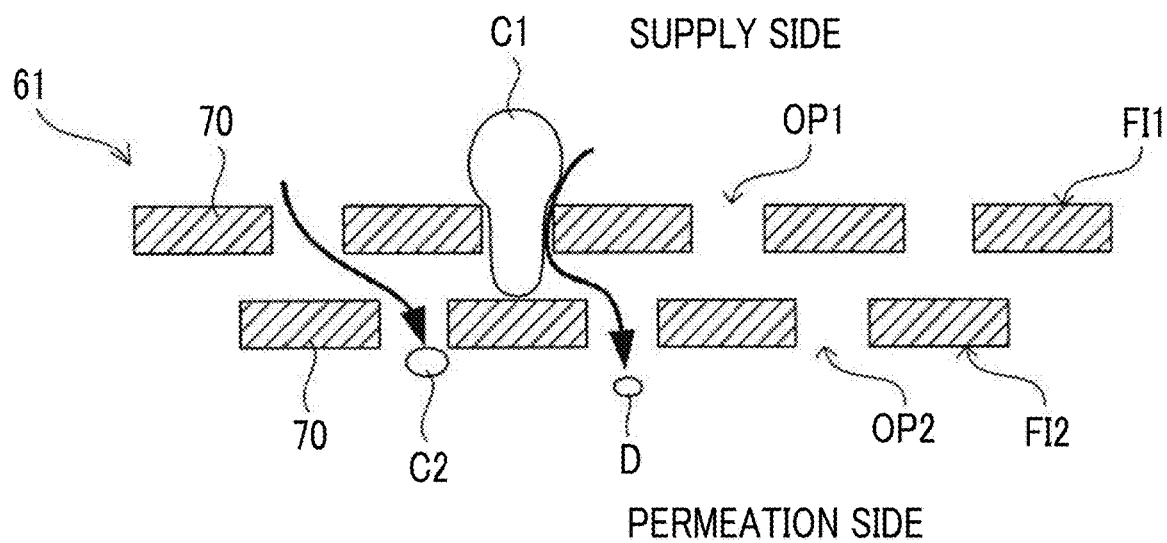
FIG. 2 is a cross-sectional view showing a typical structure of a filtration membrane according to the present exemplary embodiment.

FIG. 2 is a cross-sectional view showing a typical configuration of the filtration membrane 61 applicable to the membrane separation method of a cell suspension according to the present exemplary embodiment. In FIG. 2, a case of separating a cell aggregation C1 from a single cell C2 and debris D using the filtration membrane 61 is exemplified. The filtration membrane 61 includes an inlet-side opening OP1 formed on a first surface FI1 of the supply side 62 and an outlet-side opening OP2 which is formed on a second surface FI2 on the permeation side and communicates with the opening OP1. The openings OP1 and OP2 are disposed at positions deviated to each other in a direction parallel to the surface of the filtration membrane 61. In other words, a path connecting the opening OP1 to the opening OP2 is nonlinear, and bent or curved. In the present exemplary embodiment, the openings OP1 and OP2 do not have a portion overlapping each other. That is, the filtration membrane 61 does not have a visible hole which linearly penetrates through a space between the first surface FI1 and the second surface FI2. The openings OP1 and OP2 may partially overlap each other. The filtration membrane 61 may be a mesh-like filtration membrane formed by knitting a fibrous member 70 made of, for example, metal or plastic.

By using the filtration membrane 61 having the above-described structure, the cell aggregation C1 flowing along the surface of the filtration membrane 61 on the supply side of the container 68 of the filtration device 60 can enter the filtration membrane 61 from the opening OP1 on the supply side. However, since the opening OP2 on the permeation side of the filtration membrane 61 is disposed at a position deviated from the opening OP1 on the supply side, or since the path connecting the opening OP1 to the opening OP2 is nonlinear, the cell aggregation C1 which has entered the filtration membrane 61 cannot easily flow out to the permeation side compared to the single cell C2 and the debris D.

On the other hand, since the single cell C2 and the debris D which do not form a cell aggregation have a size sufficiently smaller than that of the cell aggregation C1, the single cell and the debris can easily flow out to the permeation side of the filtration membrane 61. In addition, the single cell C2 and the debris D can flow out to the permeation side through a side of the cell aggregation C which has entered the opening OP1 of the filtration membrane 61. It is assumed that the diameter of the cell aggregation C1 is about 50 μm to 300 μm and the diameter of the single cell C2 is about 5 μm to 25 μm. In addition, it is assumed that the diameters of a dead cell and a crushed cell as the debris D are smaller than that of the single cell C2 and are, for example, about one-half of the diameter of the single cell C2.

In a case where membrane separation processing is performed using, for example, a simple mesh-like filtration membrane formed by plain-weaving a fibrous member, the cell aggregation is deformed so as to easily flow out to the permeation side through a stitch of the filtration membrane. Clogging occurs in a case where the size of a net of the filtration membrane is reduced in order to prevent the cell aggregation from flowing out to the permeation side. In addition, the cell aggregation is divided by the net of the filtration membrane and flows out to the permeation side. In the case where the filtration membrane such as the plain weave mesh having a simple structure in the membrane separation processing in this manner, it is difficult to appropriately perform separation of the cell aggregation from the debris even if the size of the net of the filtration membrane is appropriately selected.

In contrast, according to the filtration membrane 61 of the present exemplary embodiment, since the opening OP2 on the permeation side is disposed at a position deviated from the opening OP1 on the supply side or the path connecting the opening OP1 to the opening OP2 or is nonlinear, the flowing out of the cell aggregation C1, which has entered the filtration membrane 61, to the permeation side is suppressed, and therefore, it is possible to appropriately separate the cell aggregation C1 from the single cell C2 and the debris D. In addition, according to the filtration membrane 61 according to the present exemplary embodiment, since it is difficult for the cell aggregation C1 to enter a deep portion of the filtration membrane 61 in a thickness direction, it is possible to suppress blocking (clogging) of the filtration membrane 61 and to reduce damage to cells in the membrane separation processing.

In a case of separating the cell aggregation C1 from the single cell C2 and the debris D using the filtration membrane 61, the diameters of the openings OP1 and OP2 of the filtration membrane 61 are preferably 0.01 to 3.0 times, more preferably 0.013 to 2.3 times, and still more preferably 0.02 to 2.0 times the diameter of the cell aggregation C1. By setting the diameters of the openings OP1 and OP2 to be greater than or equal to 0.01 times the diameter of the cell aggregation C1, it is possible to appropriately discharge the single cell C1 and the debris D among the cell aggregation C1, the single cell C2, and the debris D which are contained in the cell suspension to the permeation side. By setting the diameters of the openings OP1 and OP2 to be less than or equal to 3.0 times the diameter of the cell aggregation C1, it is possible to suppress the cell aggregation C1 from being caught on the surface of the filtration membrane 61 and to suppress the cell aggregation C1 from flowing out to the permeation side. The diameters of the openings OP1 and OP2 means a diameter of a circle in a case where the shapes of the openings OP1 and OP2 are circular, and means a length of a side of a polygon in a case where the shapes of the openings OP1 and OP2 are polygonal. A circle-equivalent diameter may be used as the diameter of the cell aggregation C1. The circle-equivalent diameter refers to a diameter of a circle in a case where a region defined by each outline of cell aggregations is regarded as a circle having the same area.

The case of separating cell aggregations from single cells and the debris has been exemplified using the filtration membrane 61 in the above-described description. However, it is also possible to separate single cells from debris using the filtration membrane 61. In the case of separating single cells and debris using the filtration membrane 61, it is preferable to perform the membrane separation processing using a filtration membrane having smaller diameters of the openings OP1 and OP2 than that of the filtration membrane used in a case of separating cell aggregations from single cells and debris. By using the filtration membrane 61 in the membrane separation processing for separating single cells from debris, single cells flowing along the surface of the filtration membrane 61 on the supply side of the container 68 of the filtration device 60 can enter the filtration membrane 61 from the opening OP1 on the supply side. However, since the opening OP2 on the permeation side of the filtration membrane 61 is disposed at a position deviated from the opening OP1 on the supply side, or since the path connecting the opening OP1 to the opening OP2 is nonlinear, the single cells which have entered the filtration membrane 61 cannot easily flow out to the permeation side compared to the debris. On the other hand, since the size of the debris is smaller than those of the single cells, the debris can easily flow out to the permeation side of the filtration membrane 61. In addition, the debris can flow out to the permeation side through a side of a single cell which has entered the opening OP1 of the filtration membrane 61. According to the filtration membrane 61 of the present exemplary embodiment, since the opening OP2 on the permeation side is disposed at a position deviated from the opening OP1 on the supply side or the path connecting the opening OP1 to the opening OP2 or is nonlinear, the flowing out of the single cell, which has entered the filtration membrane 61, to the permeation side is suppressed, and therefore, it is possible to appropriately separate the single cell from the debris. In addition, according to the filtration membrane 61 according to the present exemplary embodiment, since it is difficult for the single cell to enter a deep portion of the filtration membrane 61 in a thickness direction, it is possible to suppress blocking (clogging) of the filtration membrane 61 and to reduce damage to cells in the membrane separation processing.

In a case of separating single cells from debris using the filtration membrane 61, the diameters of the openings OP1 and OP2 of the filtration membrane 61 are preferably 0.05 to 0.8 times, more preferably 0.07 to 0.6 times, and still more preferably 0.1 to 0.4 times the diameters of the single cells. By setting the diameters of the openings OP1 and OP2 to be greater than or equal to 0.2 times the diameters of single cells, it is possible to appropriately discharge debris among the single cells and the debris which are contained in a cell suspension to the permeation side. By setting the diameters of the openings OP1 and OP2 to be less than or equal to 0.4 times the diameters of the single cells, it is possible to suppress the single cells from being caught on the surface of the filtration membrane 61 and to suppress the single cells from flowing out to the permeation side.

In addition, in the case of separating single cells from debris using the filtration membrane 61, it is particularly preferable to secure the uniformity of the diameters of the openings OP1 and OP2 of the filtration membrane 61. That is, when an average value of distribution of the diameters of the openings OP1 and OP2 of the filtration membrane 61 is set to X and a standard deviation is set to $\sigma$, $0<\sigma/X\leq 0.1$ is preferable satisfied, $0<\sigma/X\leq 0.05$ is more preferably satisfied, and $0<\sigma/X\leq 0.02$ is still more preferably satisfied. By satisfying $0<\sigma/X\leq 0.1$, it is possible to discharge the debris to the permeation side while suppressing the discharge of the single cells to the permeation side. $\sigma$ and X can be measured through a mercury intrusion method and can be obtained by a known statistical analysis method.

In addition, the first surface FI1 and the second surface FI2 of the filtration membrane 61 are subjected to hydrophilic treatment, and is preferably modified with a hydrophilic group. Accordingly, it is possible to improve wettability of the filtration membrane 61 and to suppress air bubbles staying in the first surface FI1, the second surface FI2, and the membrane. In addition, it is possible to suppress adhesion of proteins secreted from cells and cells themselves to the first surface FI1 and the second surface FI2. As a result, in the case of performing filtration through the cross-flow method, it is possible to form uniform flow along the surface of the filtration membrane 61 and to effectively use the first surface FI1 and the second surface FI2 of the filtration membrane 61.

The hydrophilic treatment or hydrophilic group modification with respect to the filtration membrane 61 can be performed, for example, through plasma treatment. In addition, a hydrophilic resin such as an acrylic resin having an anionic hydrophilic group may be applied to the filtration membrane 61. In addition, the hydrophilic treatment or the hydrophilic group modification may be performed using a photocatalytic action caused by introducing a titanium oxide resin into the filtration membrane 61. In addition, the filtration membrane 61 may be coated with an inorganic material such as an alkali silicate resin, a silicone resin, or water glass.

Figure 3A:
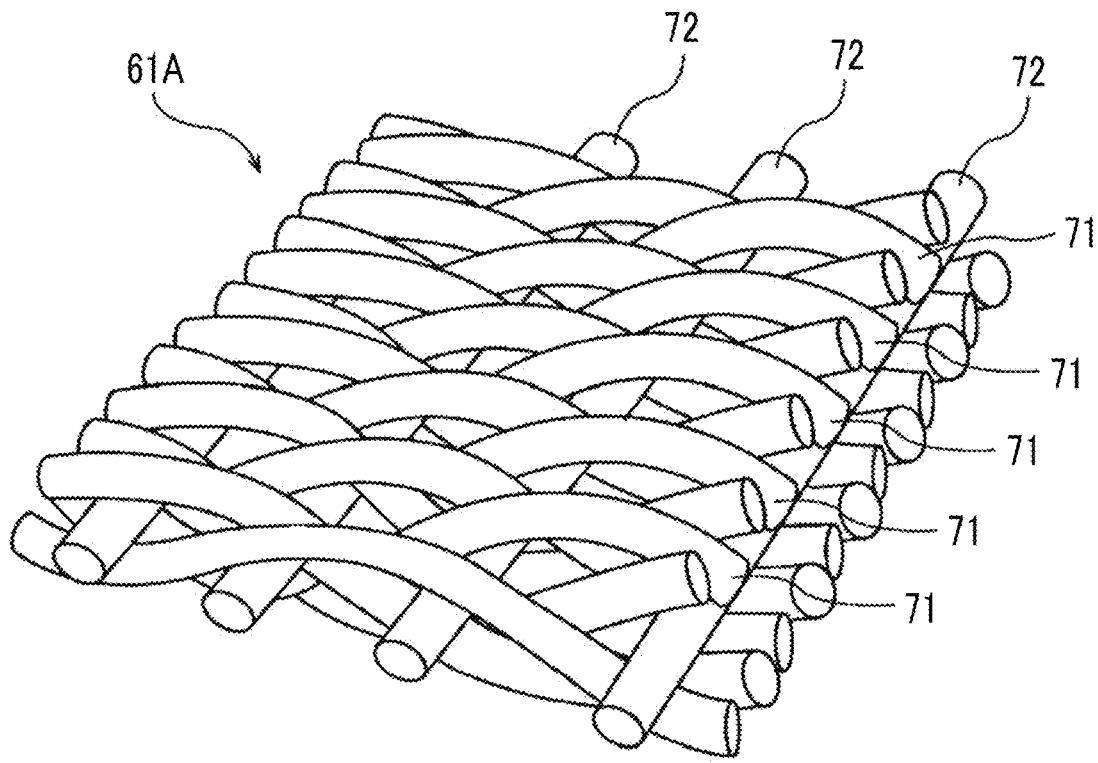
FIG. 3A is a perspective view showing a structure of a twill weave mesh that can be suitably used for a filtration membrane according to the present exemplary embodiment.

A twill weave mesh 61A formed by twill-weaving a fibrous member as shown in FIG. 3A can be suitability used as the filtration membrane 61, for example. The twill weave mesh 61A has a structure in which adjacent wefts 71 are sealed up with each other and warps 72 passing through the wefts at a constant interval are knitted such that the wefts 71 are entangled with the warps 72 while climbing over, for example, n pieces of the warps. Here, n is a natural number of 2 or more (n≥2). The twill weave mesh 61A has no visibility in the net, and openings are formed by gaps formed at intersection portions of the wefts 71 and the warps 72. The fibrous member used for the twill weave mesh 61A is made of, for example, a metal such as stainless steel or a resin such as polyester, and a metal such as stainless steel is preferable.

Figure 3B:
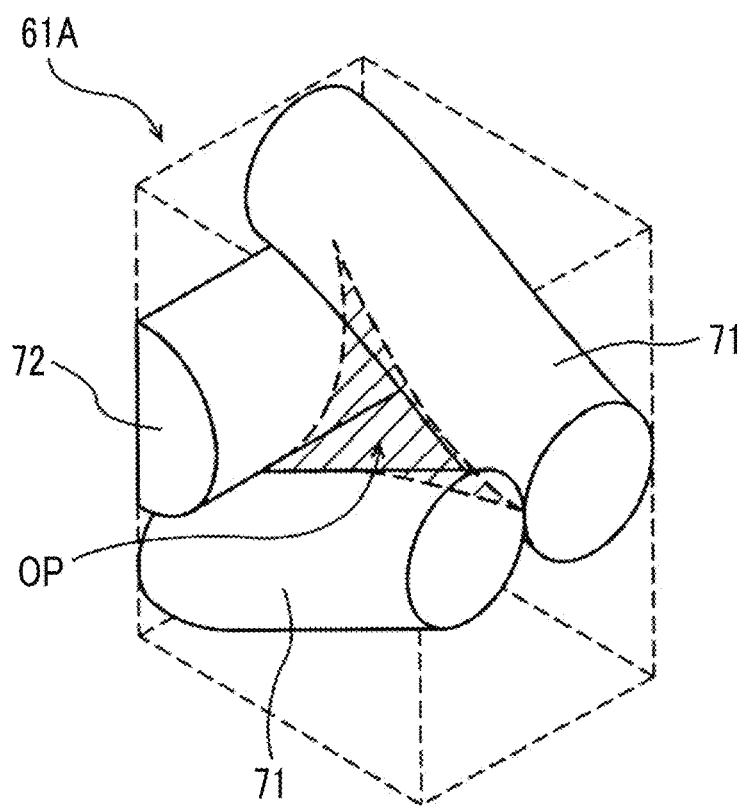
FIG. 3B is an enlarged perspective view showing an opening of the twill weave mesh.

FIG. 3B is an enlarged perspective view showing an opening OP of the twill weave mesh 61A. The opening OP of the twill weave mesh 61A is formed by a gap generated by a weave the two wefts 71 and one warp 72. The opening diameter OP of the twill weave mesh 61A is calculated as a particle diameter at which the blocking ratio becomes 95% (that is, a 95% separation particle diameter obtained from a particle permeation test) by performing the filtration test with standard particles. In a case of separating cell aggregations from single cells and debris using the twill weave mesh 61A as a filtration membrane, the 95% separation particle diameter of the twill weave mesh 61A is preferably 4 μm to 150 μm. By setting the 95% separation particle diameter of the twill weave mesh 61A to be greater than or equal to 4 μm, it is possible to appropriately discharge the single cells and the debris to the permeation side. By setting the 95% separation particle diameter of the twill weave mesh 61A to be less than or equal to 150 μm, it is possible to suppress the cell aggregations from being caught on the surface of the twill weave mesh 61A and to suppress the cell aggregations from flowing out to the permeation side.

In a case of separating single cells from debris using the twill weave mesh 61A as a filtration membrane, the 95% separation particle diameter of the twill weave mesh 61A is preferably 1 μm to 5 μm when the single cells are human cells. By setting the 95% separation particle diameter of the twill weave mesh 61A to be greater than or equal to 1 μm, it is possible to appropriately discharge the debris to the permeation side. By setting the 95% separation particle diameter of the twill weave mesh 61A to be less than or equal to 5 μm, it is possible to suppress the single cells from being caught on the surface of the twill weave mesh 61A and to suppress the single cells from flowing out to the permeation side.

In the case of separating single cells from debris, the 95% separation particle diameter of the twill weave mesh 61A is preferably 1 μm to 20 μm, more preferably 2 μm to 12 μm, and still preferably 3 μm to 7 μm when the single cells are non-human cells. By setting the 95% separation particle diameter of the twill weave mesh 61A to be greater than or equal to 1 μm, it is possible to appropriately discharge the debris to the permeation side. By setting the 95% separation particle diameter of the twill weave mesh 61A to be less than or equal to 20 μm, it is possible to suppress the single cells from being caught on the surface of the twill weave mesh 61A and to suppress the single cells from flowing out to the permeation side.

In the case of separating single cells from debris, the 95% separation particle diameter of the twill weave mesh 61A is preferably 1 μm to 20 μm, more preferably 2 μm to 12 μm, and still preferably 3 μm to 7 μm when the single cells are megakaryocytes and the debris is platelets. By setting the 95% separation particle diameter of the twill weave mesh 61A to be greater than or equal to 1 μm, it is possible to appropriately discharge the debris to the permeation side. By setting the 95% separation particle diameter of the twill weave mesh 61A to be less than or equal to 20 μm, it is possible to suppress the single cells from being caught on the surface of the twill weave mesh 61A and to suppress the cell aggregations from flowing out to the permeation side.

Figure 3C:
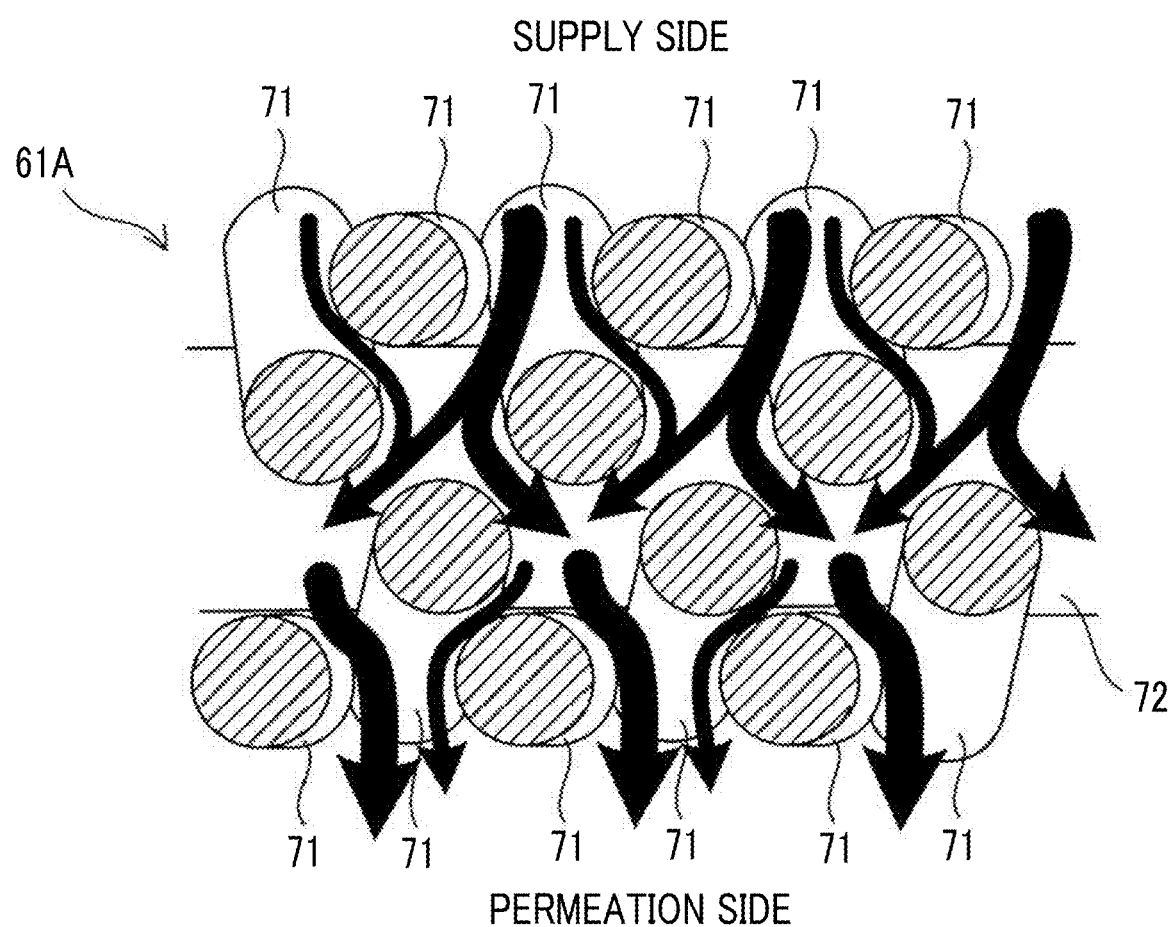
FIG. 3C is a view showing a flow of a fluid permeating through the twill weave mesh.

FIG. 3C is a view showing a cross-sectional structure of the twill weave mesh 61A. In FIG. 3C, flows of a fluid permeating through the twill weave mesh 61A is indicated by arrows. Since the twill weave mesh 61A does not have a visible hole linearly penetrating in the thickness direction, the fluid permeating through the twill weave mesh 61A flows toward the permeation side while changing the flow direction. Accordingly, particles which have a relatively large diameter and contained in the fluid tend to remain on the supply side without flowing out to the permeation side. That is, by using the twill weave mesh 61A as the filtration membrane 61, it is possible to suppress cell aggregations from flowing out to the permeation side in the membrane separation processing of a cell suspension similarly to the case of the typical structure shown in FIG. 2.

Figure 4:
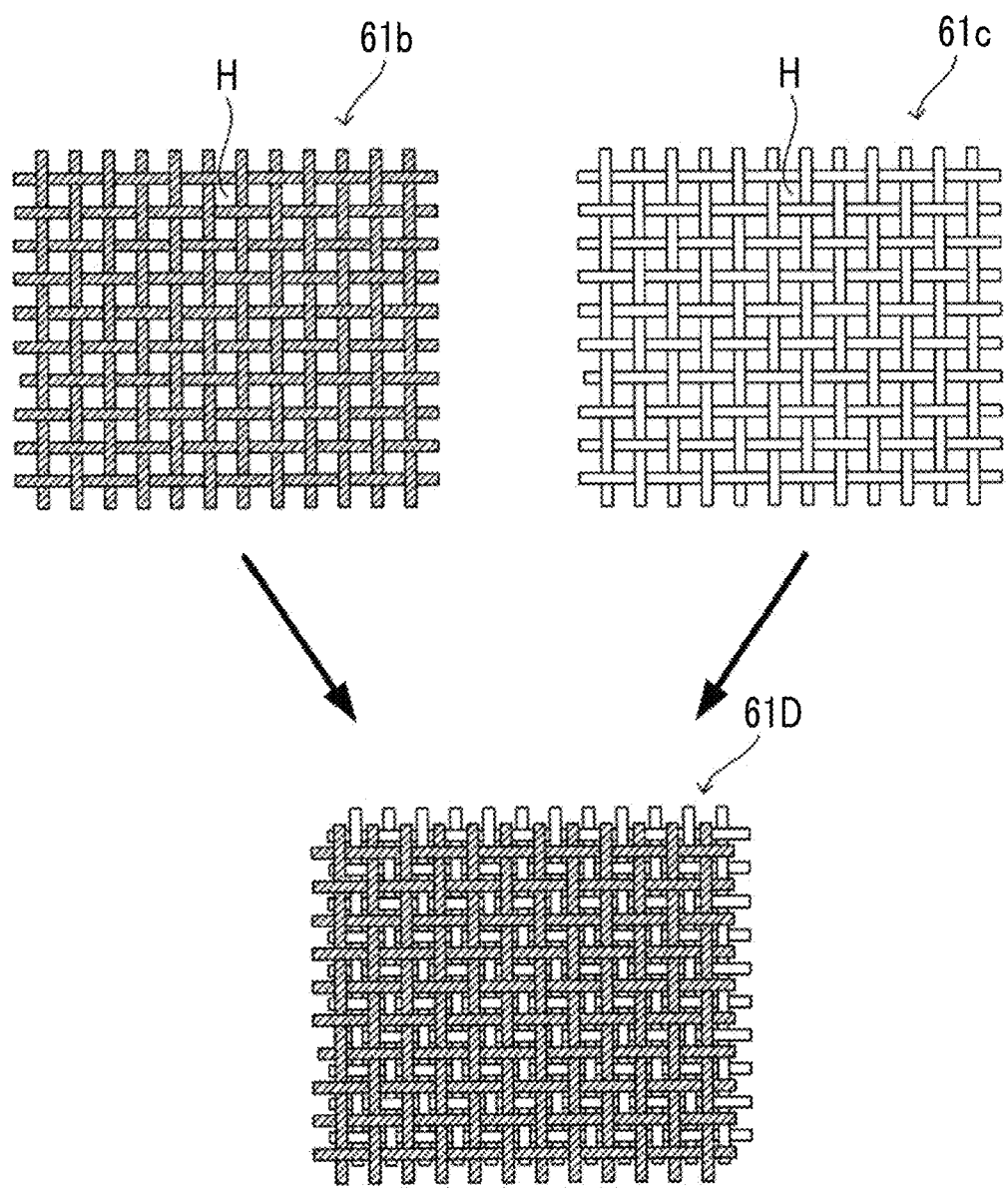
FIG. 4 is a view showing a structure of a laminated mesh that can be suitably used for the filtration membrane according to the present exemplary embodiment.

In addition, it is possible to use, for example, a laminated mesh 61D, which is formed by laminating two sheets of plain weave meshes 61b and 61c as shown in FIG. 4, as the filtration membrane 61. The plain weave meshes 61b and 61c are laminated so that the positions of respective through-holes H are deviated from each other. Even in the case of using the laminated mesh 61D, it is possible to suppress cell aggregations or single cells from flowing out to the permeation side in the membrane separation processing of a cell suspension. Three or more plain weave meshes may be laminated to form the laminated mesh 61D. The fibrous member used for the plain weave meshes 61b and 61c is made of, for example, a metal such as stainless steel or a resin such as polyester, and a metal such as stainless steel is preferable.

It is preferable to set the difference (hereinafter, referred to as a membrane surface differential pressure) between the pressure applied to the first surface FI1 on the supply side 62 of the filtration membrane 61 and the pressure applied to the second surface FI2 of the permeation side 63 of the filtration membrane 61 to 0.01 kilopascals to 60 kilopascals while performing the membrane separation processing of a cell suspension using the filtration device 60. By setting the membrane surface differential pressure of the filtration membrane 61 to be greater than or equal to 0.01 kilopascals, it is possible to appropriately discharge the debris from the supply side to the permeation side. In addition, by setting the membrane surface differential pressure of the filtration membrane 61 to be less than or equal to 60 kilopascals, it is possible to perform the membrane separation processing while suppressing cell aggregations or single cells from being divided (crushed) by the filtration membrane.

Figure 5:
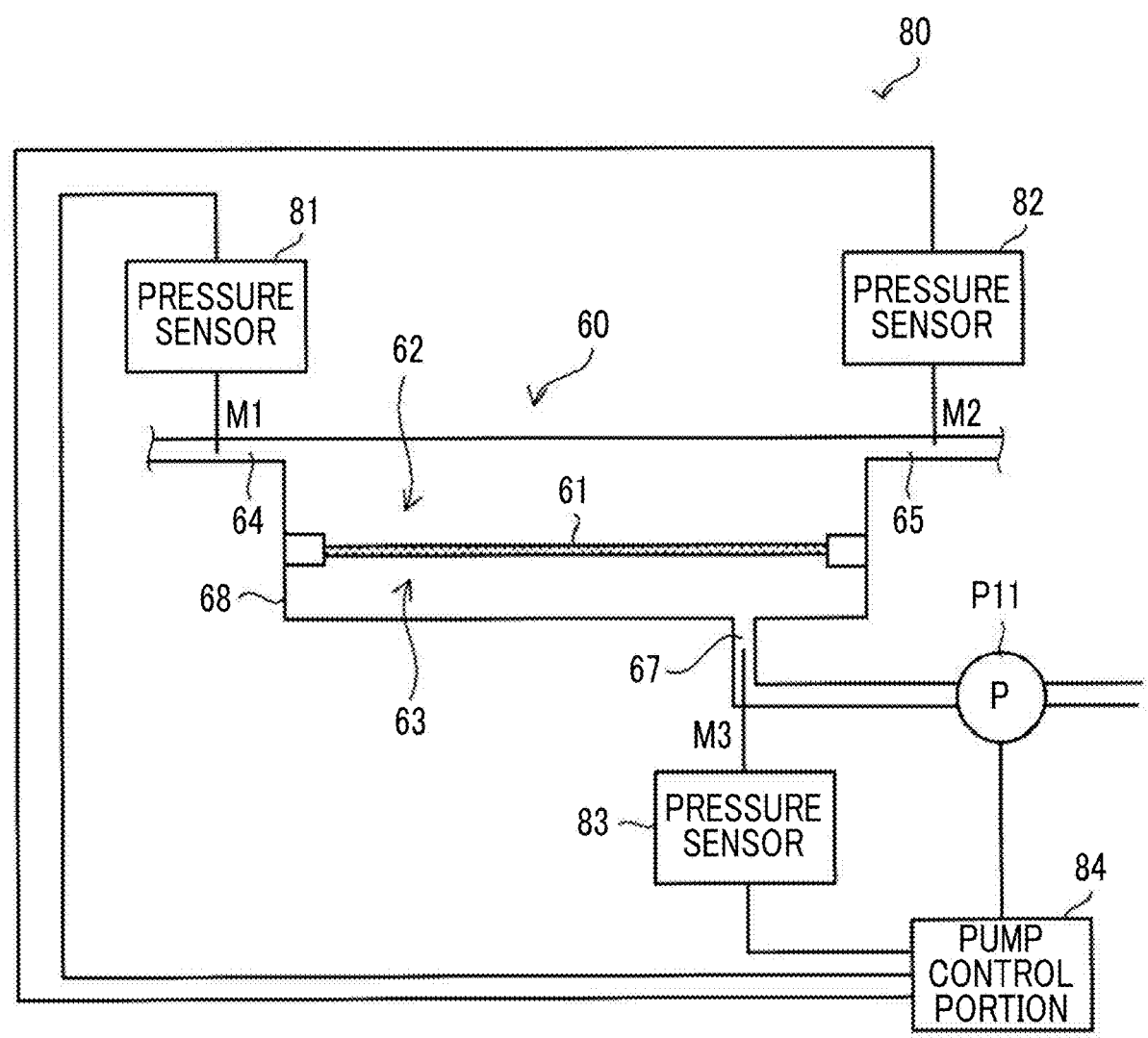
FIG. 5 is a view showing an example of a configuration of a control system that controls a membrane surface differential pressure of the filtration membrane according to the exemplary embodiment of the present disclosure.

FIG. 5 is a view showing an example of a configuration of a control system 80 that controls a membrane surface differential pressure of the filtration membrane 61 during the membrane separation processing of a cell suspension. The control system 80 includes pressure sensors 81, 82, and 83 and a pump control portion 84. The pressure sensor 81 detects a pressure M1 in the vicinity of the inflow port 64 of the filtration device 60 and supplies a detection signal indicating the magnitude of the detected pressure M1 to the pump control portion 84. The pressure sensor 82 detects a pressure M2 in the vicinity of the outflow port 65 of the filtration device 60 and supplies a detection signal indicating the magnitude of the detected pressure M2 to the pump control portion 84. The pressure sensor 83 detects a pressure M3 in the discharge flow path 67 of the filtration device 60 and supplies a detection signal indicating the magnitude of the detected pressure M3 to the pump control portion 84. The pump control portion 84 controls the rotational frequency of the pump P11 provided on the discharge flow path 67 per unit time based on the pressures M1, M2, and M3 indicated by the detected signals supplied from the pressure sensors 81, 82, and 83.

Here, the membrane surface differential pressure ΔM of the filtration membrane 61 during the membrane separation processing is represented by Equation (1).

$$\Delta M = (M1 + M2)/2 - M3 \qquad (1)$$

(M1+M2)/2 means an average value of the pressures on the supply side 62 of the filtration device 60. The pump control portion 84 calculates the membrane surface differential pressure ΔM by substituting the pressures M1, M2, and M3 detected by the pressure sensors 81, 82, and 83 into Equation (1). The pump control portion 84 controls the rotational frequency of the pump P11 per unit time so that the membrane surface differential pressure ΔM becomes a predetermined value within a range of 5 kilopascals to 60 kilopascals. The pump P11 operates so as to form a flow of discharging a liquid containing debris discharged to the permeation side 63 to the outside of the filtration device 60 via the discharge flow path 67. As the rotational frequency of the pump P11 per unit time increases, the pressure on the permeation side 63 decreases and the membrane surface differential pressure ΔM changes in a direction where the membrane surface differential pressure increases.

Figure 6:
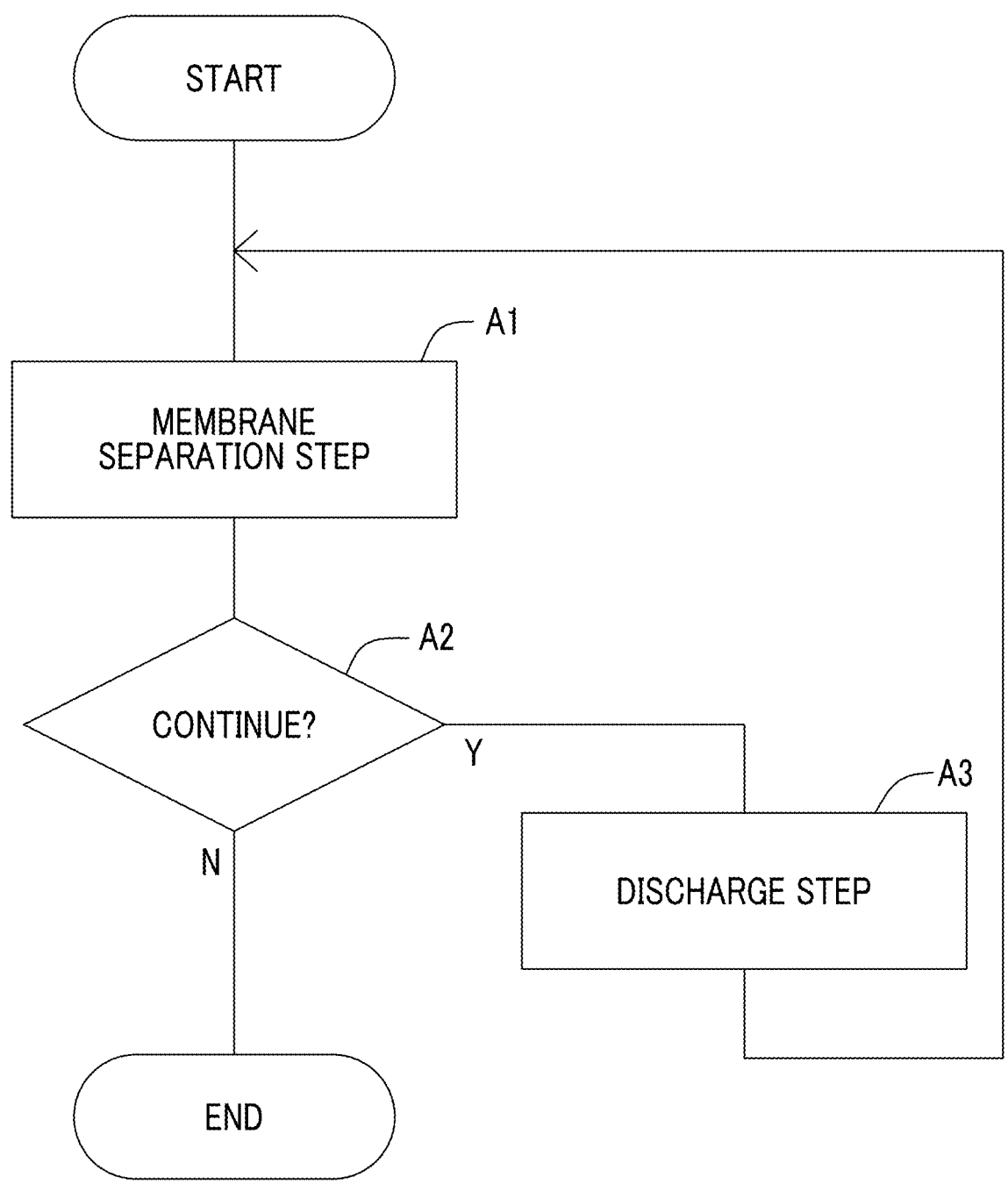
FIG. 6 is a flowchart showing an example of a membrane separation method of a cell suspension according to the exemplary embodiment of the present disclosure.

Processing for eliminating clogging in the filtration membrane 61 may be appropriately performed while performing the membrane separation processing of a cell suspension using the filtration device 60. FIG. 6 is a flowchart showing an example of the membrane separation method of a cell suspension which includes processing for eliminating clogging in the filtration membrane 61.

In a membrane separation step A1, the membrane separation processing of a cell suspension is performed by allowing the cell suspension to flow along a direction of the surface of the filtration membrane 61. At this time, the flow rate of the cell suspension is set to a velocity V1. In the membrane separation step A1, in some cases, air bubbles, cells, proteins secreted from cells, and the like may adhere to the surface of the filtration membrane 61. These cause clogging in the filtration membrane 61.

In a determination step A2, it is determined whether or not the membrane separation processing is to be continued. In a case where the membrane separation processing is not to be continued, the processing is finished. In a case where the membrane separation processing is to be continued, the processing is shifted to a discharge step A3.

In the discharge step A3, a cell suspension or a washing liquid is made to flow along the direction of the surface of the filtration membrane 61 at a velocity V2 greater than the velocity V1. By generating a liquid flow having a relatively high flow rate on the surface of the filtration membrane 61 in this manner, air bubbles, cells, proteins, and the like which have adhered to the filtration membrane 61 are scratched, and clogging of the filtration membrane 61 is eliminated.

Figure 7:
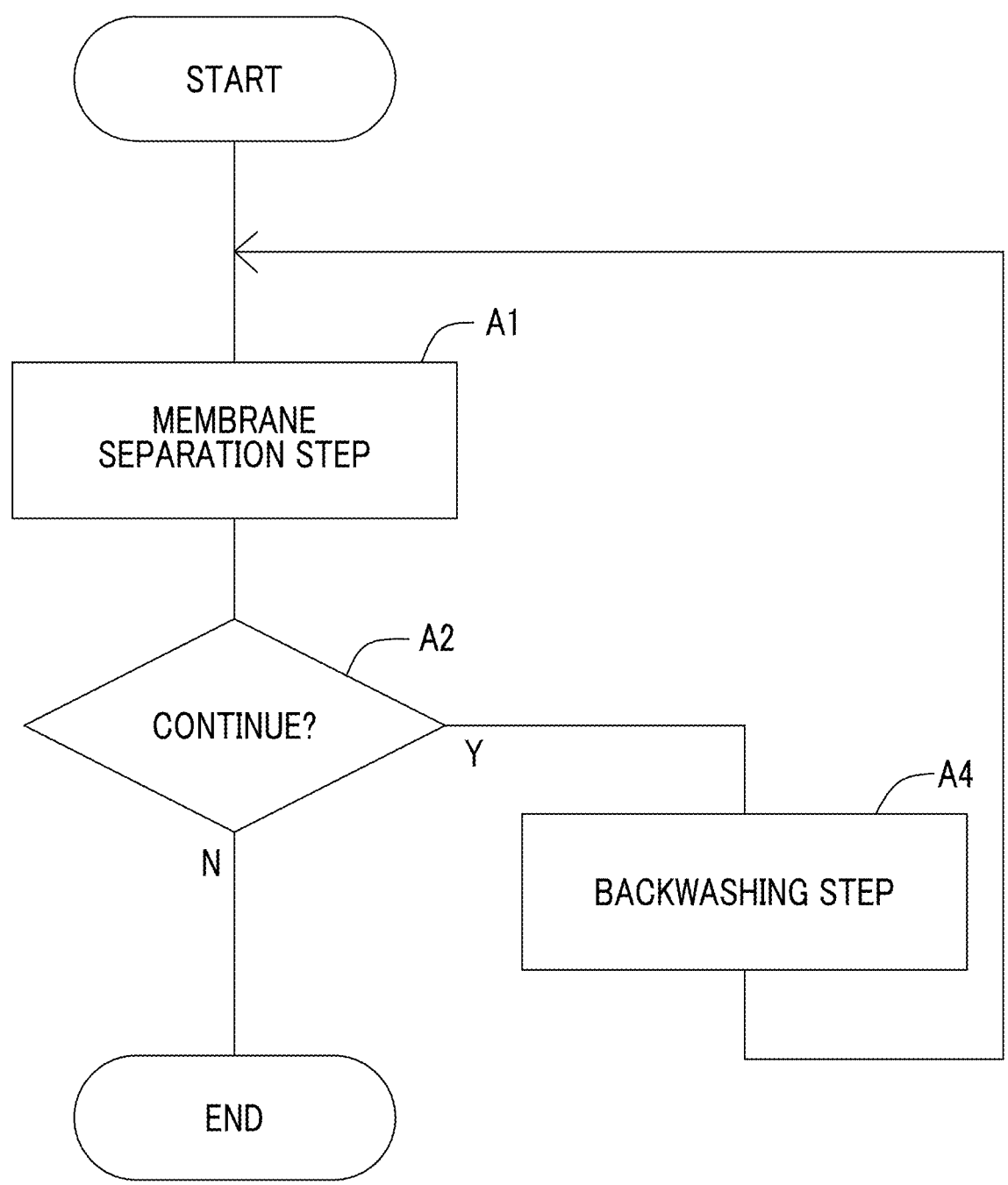
FIG. 7 is a flowchart showing an example of the membrane separation method of the cell suspension according to the exemplary embodiment of the present disclosure.

The above-described discharge step A3 may be replaced with a backwashing step A4 as shown in FIG. 7. In the backwashing step A4, the pump P11 provided on the discharge flow path 67 of the filtration device 60 is stopped, and gas or a washing liquid such as a medium is injected into the permeation side 63 of the container 68 to generate a liquid flow or airflow from the permeation side 63 to the supply side 62. In other words, the pressure applied to the second surface FI2 of the permeation side 63 of the filtration membrane 61 is made larger than the pressure applied to the first surface FI1 on the supply side. That is, in the backwashing step A4, the magnitude relation of the pressure applied to the first surface FI1 and the second surface FI2 of the filtration membrane 61 is opposite to that of the membrane separation step A1. By generating a liquid flow or airflow flowing from the permeation side 63 to the supply side 62 in this manner, air bubbles, cells, proteins, and the like which have adhered to the filtration membrane 61 are removed from the filtration membrane 61, and clogging in the filtration membrane 61 is eliminated.

Figure 8:
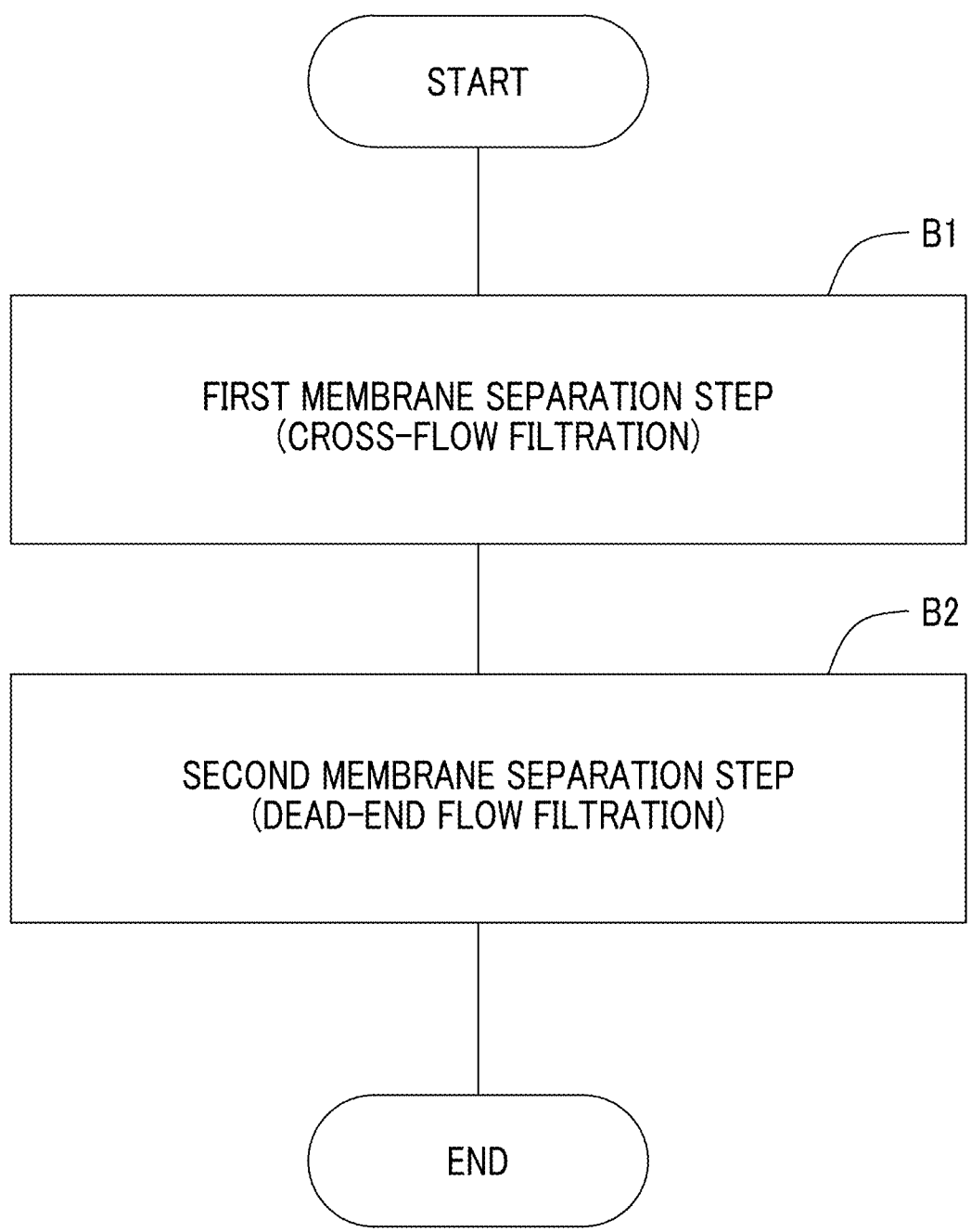
FIG. 8 is a flowchart showing an example of the membrane separation method of the cell suspension according to the exemplary embodiment of the present disclosure.

FIG. 8 is a flowchart showing another example of the membrane separation method of a cell suspension using the filtration device 60. In a first membrane separation step B1, filtration is performed by a cross-flow method in which a cell suspension flows along the surface of the filtration membrane 61 from the inflow port 64 toward the outflow port 65. Subsequently, in a second membrane separation step B2, the cell suspension subjected to the membrane separation processing through the first membrane separation step B1 is made to flow in again from the inflow port 64 in a state in which the outflow port 65 is closed. Accordingly, in the second membrane separation step B2, filtration is performed by a dead-end flow method in which the flow direction of the cell suspension is orthogonal to the surface of the filtration membrane 61.

According to the filtration through the cross-flow method, it is possible to suppress clogging in the filtration membrane 61 and to suppress damage to cells. However, it is not easy to concentrate the cell suspension to a high concentration. On the other hand, according to the dead-end flow method, it is possible to concentrate the cell suspension to a high concentration whereas clogging in the filtration membrane 61 is liable to occur and there is a concern that cells are damaged. By using the filtration through the cross-flow method and the filtration through the dead-end flow method, it is easy to concentrate the cell suspension to a desired concentration while minimizing clogging in the filtration membrane 61 and damage to the cells.

Figure 9:
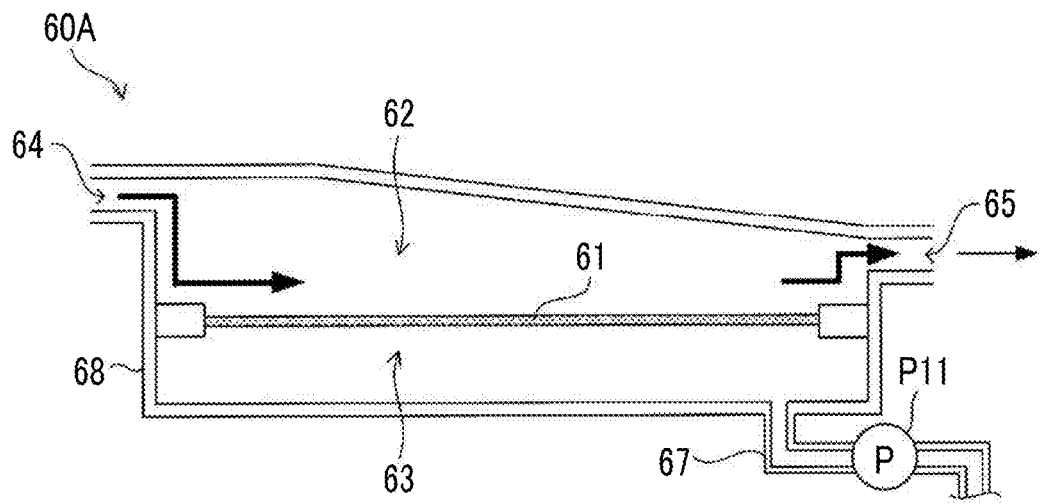
FIG. 9 is a view showing a configuration of a filtration device according to an exemplary embodiment of the present disclosure.

FIG. 9 is a view showing a configuration of a filtration device 60A according to another exemplary embodiment of the present disclosure. In the filtration device 60A, the cross-sectional area of a flow path of a cell suspension on a supply side 62 gradually decreases from an upstream side (inflow port 64 side) to a downstream side (outflow port 65 side) of the flow path.

Here, in a case where the amount of liquid flowing in from the inflow port 64 per unit time is set to Q1, the amount of liquid flowing out from the outflow port 65 is set to Q2, and the amount of liquid discharged from a discharge flow path 67 per unit time is set to Q3, a relationship represented by Equation (2) is satisfied between Q1, Q2, and Q3.

$$Q2 = Q1 - Q3 \qquad (2)$$

That is, the amount Q2 of liquid flowing out from the outflow port 65 is smaller than the amount Q1 of liquid flowing in from the inflow port 64. Accordingly, in a case where the cross-sectional area of the flow path of the cell suspension is made constant, the flow rate on the downstream side (outflow port 65 side) of the flow path becomes smaller than that on the upstream side (inflow port 64 side). In this case, cell aggregations or single cells tend to be deposited on the filtration membrane 61 on the downstream side where the flow rate decreases. In order to avoid this, it is conceivable to increase the flow rate on the upstream side in anticipation of the decrease in the flow rate on the downstream side. However, in this case, there is a concern that damage to cells may increase, which is not preferable.

According to the filtration device 60A of the present exemplary embodiment, the cross-sectional area of the flow path of the cell suspension gradually decreases from the upstream side (inflow port 64 side) to the downstream side (outflow port 65 side), and therefore, the flow rate of the cell suspension becomes substantially constant between the upstream side and the downstream side of the flow path. That is, according to the filtration device 60A, it is possible to suppress the decrease in the flow rate on the downstream side of the flow path while suppressing damage to the cells, and to suppress the deposition of cell aggregations or single cells on the filtration membrane 61.

Figure 10:
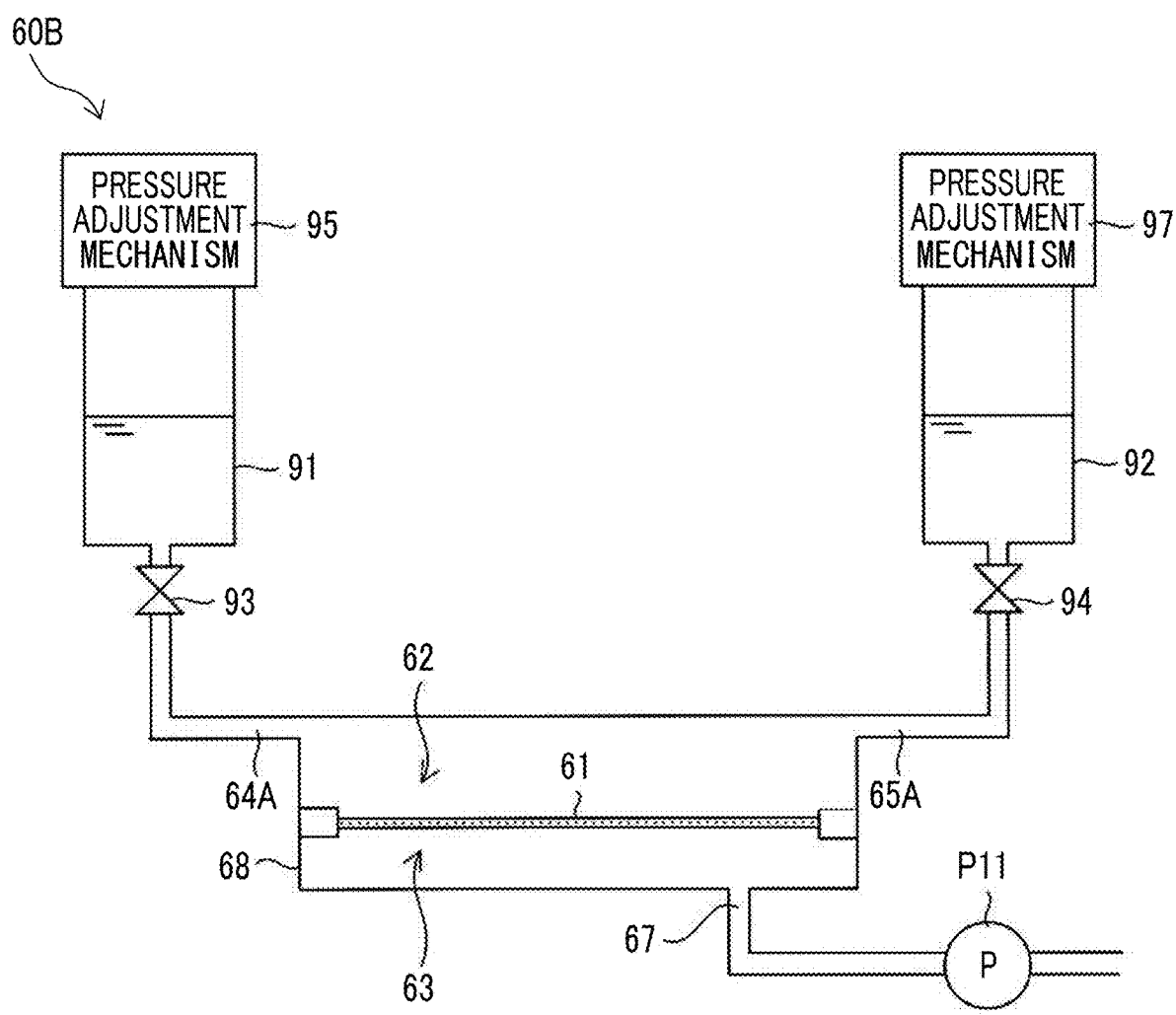
FIG. 10 is a view showing a configuration of a filtration device according to an exemplary embodiment of the present disclosure.

FIG. 10 is a view showing a configuration of a filtration device 60B according to another exemplary embodiment of the present disclosure. The filtration device 60B includes a first circulation port 64A and a second circulation port 65A respectively corresponding to the inflow port 64 and the outflow port 65 of the filtration device 60 shown in FIG. 1. In addition, the filtration device 60B includes a first storage container 91 connected to the first circulation port 64A and a second storage container 92 connected to the second circulation port 65A. A pressure adjustment mechanism 95 for adjusting the pressure inside the first storage container 91 is provided in the first storage container 91. Similarly, a pressure adjustment mechanism 97 for adjusting the pressure inside the second storage container 92 is provided in the second storage container 92. On-off valves 93 and 94 are respectively provided on a flow path connecting the first circulation port 64A to the first storage container 91 and a flow path connecting the second circulation port 65A to the second storage container 92.

The first storage container 91 and the second storage container 92 are containers for storing a cell suspension to be subjected to membrane separation processing. As the cell suspension moves between the first storage container 91 and the second storage container 92, the cell suspension flows along the surface of a filtration membrane 61 to be subjected to membrane separation processing. The cell suspension is concentrated to a desired concentration by reciprocating between the first storage container 91 and the second storage container 92. The cell suspension concentrated to a desired concentration is collected in the first storage container 91 or the second storage container 92.

In a case where the cell suspension is to be moved from the first storage container 91 to the second storage container 92, the surface of the cell suspension stored in the first storage container 91 is pressurized by the pressure adjustment mechanism 95, and the on-off valves 93 and 94 enter an open state. In a case where the cell suspension is to be moved from the second storage container 92 to the first storage container 91, the surface of the cell suspension stored in the second storage container 92 is pressurized by the pressure adjustment mechanism 97, and the on-off valves 93 and 94 enter an open state. The pressure adjustment mechanisms 95 and 97 have a mechanism that pressurizes the surface of the cell suspension with, for example, clean air. The pressure adjustment mechanisms 95 and 97 generate a liquid flow of the cell suspension by generating a pressure difference between the first storage container 91 and the second storage container 92.

According to the filtration device 60B of the present exemplary embodiment, it is unnecessary to use a pump of a type of generating a liquid flow by a squeezing operation of a tube, for example, a tube pump having a concern about damage to cells. That is, according to the filtration device 60B of the present exemplary embodiment, it is possible to generate a liquid flow necessary for the membrane separation processing of a cell suspension without damaging cells.

[Cell Culture Device]

Figure 11:
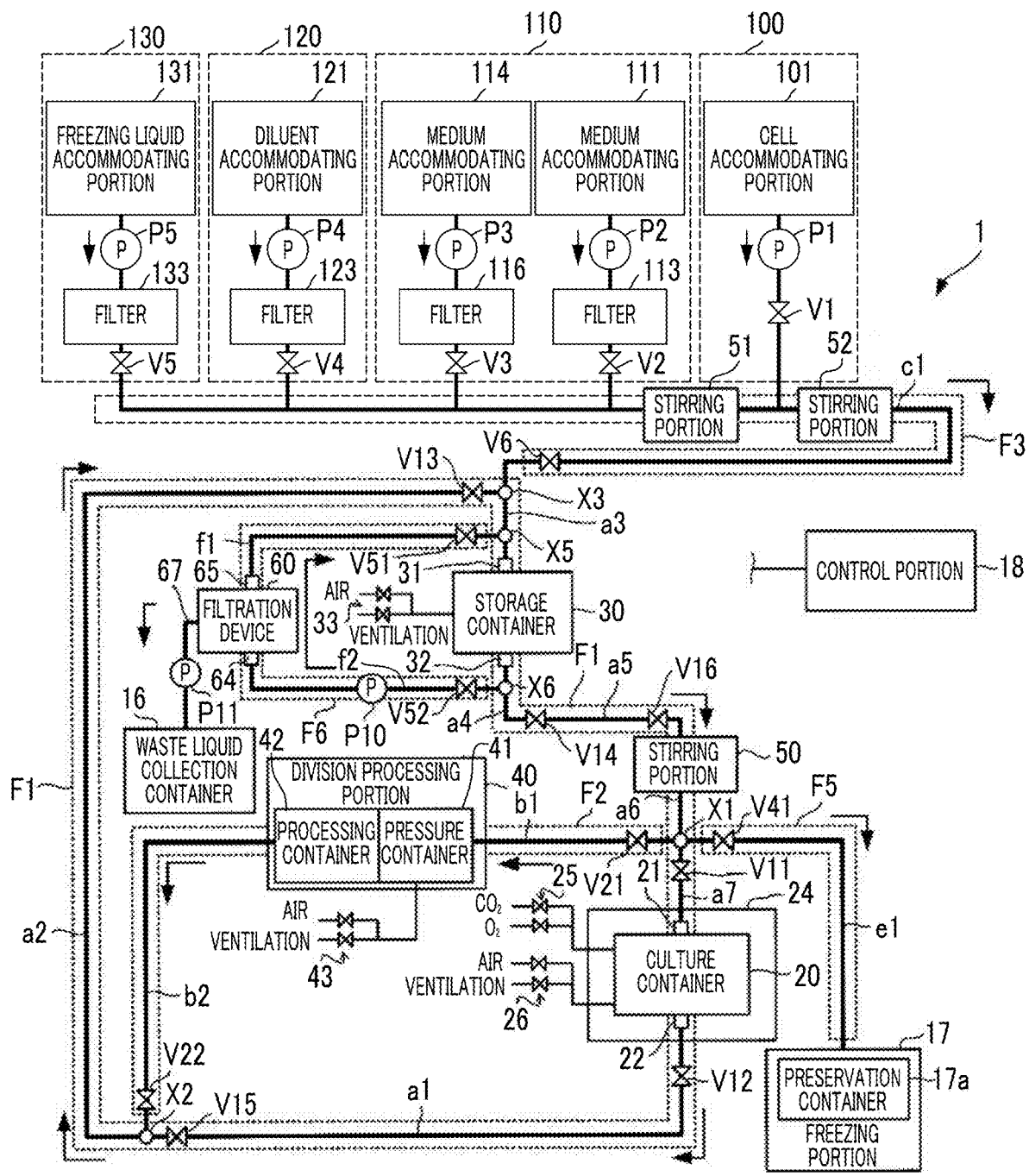
FIG. 11 is a view showing a configuration of a cell culture device according to the exemplary embodiment of the present disclosure.

FIG. 11 is a diagram showing a configuration of a cell culture device 1 according to the exemplary embodiment of the present disclosure including the filtration device 60. The cell culture device 1 comprises a cell supply portion 100, a medium supply portion 110, a diluent supply portion 120, and a freezing liquid supply portion 130 in addition to the filtration device 60. In addition, the cell culture device 1 comprises a culture container 20, a storage container 30, a division processing portion 40, a waste liquid collection container 16, and a freezing portion 17.

The cell culture device 1 accommodates cells supplied from the cell supply portion 100 within the culture container 20 together with a medium (culture solution) supplied from the medium supply portion 110 and cultures the cells in a state in which the cells are made to, for example, float in the medium within the culture container 20.

<Cell Supply Portion>

The cell supply portion 100 has a cell accommodating portion 101 which accommodates cells to be cultured using the cell culture device 1 in a state where pluripotent stem cells are frozen; and a pump P1 which sends out the cells accommodated in the cell accommodating portion 101 out into a flow path F3 including a pipe c1. In addition, the cell supply portion 100 includes an on-off valve V1, which is provided on a downstream side of the pump P1, of a pipe connecting the cell accommodating portion 101 to the pipe c1. The cells accommodated in the cell accommodating portion 101 are sent out into the flow path F3 using the pump P1 being driven and the on-off valve V1 entering an open state.

<Medium Supply Portion>

The medium supply portion 110 includes: medium accommodating portions 111 and 114 accommodating a medium (culture solution) used for culturing of the cells; pumps P2 and P3 which send out media respectively accommodated in the medium accommodating portions 111 and 114 to the flow path F3; and filters 113 and 116 which are used for sterilizing the media respectively sent out from the pumps P2 and P3. In addition, the medium supply portion 110 includes: an on-off valve V2, which is provided on a downstream side of the filter 113, of a pipe connecting the medium accommodating portion 111 to the pipe c1; and an on-off valve V3, which is provided on a downstream side of the filter 116, of a pipe connecting the medium accommodating portion 114 to the pipe c1. In this manner, the medium supply portion 110 includes a medium supply function of two lines consisting of a first line including the medium accommodating portion 111, the pump P2, the filter 113, and the on-off valve V2, and a second line including the medium accommodating portion 114, the pump P3, the filter 116, and the on-off valve V3, and therefore, two media different from each other can be supplied. The number of lines in the medium supply portion 110 can be appropriately increased and decreased in accordance with a cell culture protocol or the like. That is, the medium supply portion 110 may be formed so as to supply three or more types of media, or may be formed so as to supply one medium. The medium accommodated in the medium accommodating portion 111 is sent out to the flow path F3 using the pump P2 being driven and the on-off valve V2 entering an open state. The medium accommodated in the medium accommodating portion 114 is sent out to the flow path F3 using the pump P3 being driven and the on-off valve V3 entering an open state.

Media which can be applied to a cell culture using the cell culture device 1 according to the present exemplary embodiment are not particularly limited, and all media can be applied thereto. Specific examples thereof include liquid media such as a base medium for mammalian cells (for example, Dulbecco's Modified Eagle's Medium (DMEM), Dulbecco's Modified Eagle Medium: Nutrient Mixture F-12 (DMEM/F-12), Eagle's minimal essential medium (EMEM), Basal Medium Eagle (BME), Roswell Park Memorial Institute 1640 Medium (RPMI1640 Medium), E8 base medium, Skeletal Muscle Cell Basal Medium (SkBM), MCDB104, and MCDB153, 199, L15), a commercially available culture solution for maintaining stem cells, a base medium for insect cells, a medium for yeast, and a medium for bacteria.

Polymer compounds without cytotoxicity may be added to the media which can be applied to cell culture using the cell culture device 1 according to the present exemplary embodiment for the purpose of continuously floating the cells and/or the purpose of preventing the cells from being closely attached to each other. Examples of the polymer compounds added to the media for the above-described purposes include a polymer compound that adjusts a specific gravity of a medium, a polymer compound that adjusts viscosity of a medium, and a polymer compound that forms a three-dimensional network structure in a medium. Examples of such polymer compounds include polysaccharides such as cellulose, methylcellulose, carboxymethyl cellulose, gellan gum, deacylated gellan gum, hyaluronic acid, alginic acid, carrageenan, xanthan gum, diutan gum, starch, and pectin; proteins such as collagen and gelatin; synthetic polymers such as polyethylene glycol and polyvinyl pyrrolidone.

Various types of generally addable components, for example, antibiotics such as penicillin and streptomycin; vitamins such as ascorbic acid and retinoic acid, or vitamin derivatives; sugar sources such as glucose; amino acids; mineral salts; serum or serum substitutes; proteins such as transferrin; hormones such as insulin; growth factors; differentiation inhibitory factors; antioxidants such as 2-mercaptoethanol and dithiothreitol; metal ions such as a calcium ion, a magnesium ion, a zinc ion, an iron ion, and a copper ion may be added to the media which can be applied to the cell culture using the cell culture device 1 according to the present exemplary embodiment.

<Diluent Supply Portion>

The diluent supply portion 120 includes: a diluent accommodating portion 121 which accommodates a diluent to be used for a diluting processing to be appropriately performed during a cell culture process; a pump P4 which sends the diluent accommodated in the diluent accommodating portion 121 out into the flow path F3; and a filter 123 which is used for sterilizing the diluent sent out from the pump P4. In addition, the diluent supply portion 120 has: an on-off valve V4, which is provided on a downstream side of the filter 123, of a pipe connecting the diluent accommodating portion 121 to the pipe c1. The diluent accommodated in the diluent accommodating portion 121 is sent out into the flow path F3 using the pump P4 being driven and the on-off valve V4 entering an open state.

The diluent which can be applied to the cell culture using the cell culture device 1 according to the present exemplary embodiment is not particularly limited, and examples of the diluent include a base medium for mammalian cells (for example, DMEM, DMEM/F-12, MEM, DME, RPMI1640, MCDB104, 199, MCDB153, L15, SkBM, Basal Medium, or E8 base medium). In a case where the diluting processing is unnecessary in the cell culture process, it is possible to omit the diluent supply portion 120.

<Freezing Liquid Supply Portion>

The freezing liquid supply portion 130 includes: a freezing liquid accommodating portion 131 which accommodates a freezing liquid used in a case of cryopreservation of cultured cells in the freezing portion 17; a pump P5 which sends the freezing liquid accommodated in the freezing liquid accommodating portion 131 out into the flow path F3; and a filter 133 which is used for sterilizing the freezing liquid sent out from the pump P5. In addition, the freezing liquid supply portion 130 includes an on-off valve V5, which is provided on a downstream side of the filter 133, of a pipe connecting the freezing liquid accommodating portion 131, the pump P5, and the filter 133. The freezing liquid accommodated in the freezing liquid accommodating portion 131 is sent out into the flow path F3 using the pump P5 being driven and the on-off valve V5 entering an open state. In a case where it is unnecessary to cryopreserve the cultured cells, it is possible to omit the freezing liquid supply portion 130 in the cell culture device 1.

<Culture Container>

The culture container 20 is a container for accommodating the cells supplied from the cell supply portion 100 together with a medium supplied from the medium supply portion 110 and culturing the accommodated cells. The form of the culture container 20 is not particularly limited, and it is possible to use a container made of glass or stainless steel, or a container having a form of a plastic bag. The culture container 20 includes an inflow port 21 for allowing the cells and a medium to flow into the culture container 20 and an outflow port 22 for allowing the cells and the medium which have been accommodated in the culture container 20 to flow out to the outside of the culture container 20.

The culture container 20 can be accommodated in an incubator 24, which is airtight closed and of which the temperature is controlled to, for example, 30° C. to 40° C. (preferably 37° C.) and the $CO_2$ concentration is controlled to, for example, 2% to 10% (preferably 5%). The incubator 24 comprises a gas supply mechanism 25 for supplying oxygen ($O_2$) and carbon dioxide ($CO_2$) to the cells accommodated in the culture container 20 together with a medium. In addition, the incubator 24 comprises a pressure adjustment mechanism 26 which adjusts the pressure in the culture container 20. The pressure adjustment mechanism 26 pressurizes the atmosphere within the culture container 20 by introducing air into the culture container 20, or releases the atmosphere within the culture container 20 into the air by discharging the atmosphere within the culture container 20 to the outside. The pressure adjustment mechanism 26 allows the cells and a medium which have been accommodated in the culture container 20 to flow into a circulation flow path F1 by increasing the pressure within the culture container 20 more than the pressure within the circulation flow path F1 to be described below.

<Circulation Flow Path>

The cell culture device 1 has the circulation flow path F1 including pipes a1 to a7 connecting the outflow port 22 to the inflow port 21 of the culture container 20. Cells and a medium which have been accommodated in the culture container 20 circulate within the circulation flow path F1 in each processing to be described below which is performed in culture process. The cells and the medium flowing inside the circulation flow path F1 flow into the culture container 20 via the inflow port 21, and the cells and the medium which have been accommodated inside the culture container 20 flow out to the inside the circulation flow path F1 via the outflow port 22.

An on-off valve V11 is provided in the pipe a7 forming the circulation flow path F1 connected to the inflow port 21 of the culture container 20. An on-off valve V12 is provided in the pipe a1 forming the circulation flow path F1 connected to the outflow port 22 of the culture container 20. The on-off valve V11 is made to enter an open state in a case where the cells and a medium are allowed to flow into the culture container 20 from the circulation flow path F1 and is made to enter a closed state in other cases. The on-off valve V12 is made to enter an open state in a case where the cells and a medium are allowed to flow out from the inside of the culture container 20 to the inside of the circulation flow path F1 and is made to enter a closed state in other cases.

The flow path F3 formed by the pipe c1 connected to the cell supply portion 100, the medium supply portion 110, the diluent supply portion 120, and the freezing liquid supply portion 130 is connected to the circulation flow path F1 in a connection region X3. That is, cells accommodated in the cell accommodating portion 101, media respectively accommodated in the medium accommodating portions 111 and 114, a diluent accommodated in the diluent accommodating portion 121, and a freezing liquid accommodated in the freezing liquid accommodating portion 131 are supplied to the circulation flow path F1 via the flow path F3 and the connection region X3.

An on-off valve V6 is provided in the vicinity of the connection region X3 in the pipe c1 forming the flow path F3. The on-off valve V6 is made to enter an open state in a case where the cell supply portion 100, the medium supply portion 110, the diluent supply portion 120, and the freezing liquid supply portion 130 respectively supply cells, a medium, a diluent, or a freezing liquid to the inside of the circulation flow path F1 and is made to enter a closed state in other cases.

<Storage Container>

The storage container 30 is provided within the circulation flow path F1, that is, in the middle of the circulation flow path F1. The storage container 30 is a container for temporarily storing cells, a medium, a diluent, or a freezing liquid flowing inside the circulation flow path F1, and is used in subculture processing, medium replacement processing, division processing, and freezing processing to be described below which are performed during a culture period. The form of the storage container 30 is not particularly limited, and it is possible to use, for example, a container made of glass or stainless steel or a container having a form of a plastic bag.

The storage container 30 includes: an inflow port 31 for allowing cells, a medium, a diluent, or a freezing liquid flowing inside the circulation flow path F1 to flow into the storage container 30; and an outflow port 32 for allowing the cells, the medium, the diluent, or the freezing liquid which have been accommodated in the storage container 30 to flow out to the inside the circulation flow path F1. The inflow port 31 of the storage container 30 is connected to the outflow port 22 of the culture container 20 using the pipes a1 to a3 forming the circulation flow path F1. The outflow port 32 of the storage container 30 is connected to the inflow port 21 of the culture container 20 using the pipes a4 to a7 forming the circulation flow path F1. In addition, in the present exemplary embodiment, the connection region X3 to which the circulation flow path F1 and the flow path F3 are connected is disposed in the vicinity of the inflow port 31 of the storage container 30. However, the connection position between the circulation flow path F1 and the flow path F3 can be disposed at any position within the circulation flow path F1.

An on-off valve V13 is provided in the vicinity of the inflow port 31 of the storage container 30 in the pipe a2 forming the circulation flow path F1. The on-off valve V13 is made to enter an open state in a case where cells, a medium, and the like are allowed to flow into the storage container 30 from the circulation flow path F1 and is made to enter a closed state in other cases. In addition, an on-off valve V14 is provided in the vicinity of the outflow port 32 of the storage container 30 in the pipe a5 forming the circulation flow path F1. The on-off valve V14 is made to enter an open state in a case where cells, a medium, and the like are transferred to the culture container 20, the division processing portion 40, or the freezing portion 17 from the storage container 30, and is made to enter a closed state in other cases.

The storage container 30 comprises a pressure adjustment mechanism 33 which adjusts the pressure within the storage container 30. The pressure adjustment mechanism 33 pressurizes the atmosphere within the storage container 30 by introducing air into the storage container 30, or releases the atmosphere within the storage container 30 into the air by discharging the atmosphere within the storage container 30 to the outside. The pressure adjustment mechanism 33 allows cells, a medium, a diluent, and a freezing liquid which have been stored in the storage container 30 to flow out into the circulation flow path F1 from the outflow port 32 by increasing the pressure within the storage container 30 more than the pressure within the circulation flow path F1.

The cell culture device 1 includes a flow path F2 including pipes b1 and b2 which connect a connection region X1 positioned between the outflow port 32 of the storage container 30 and the inflow port 21 of the culture container 20, within the circulation flow path F1, to a connection region X2 positioned between the inflow port 31 of the storage container 30 and the outflow port 22 of the culture container 20, within the circulation flow path F1. Cells, a medium, and the like flowing inside the circulation flow path F1 can flow into the flow path F2 via the connection region X1. In addition, cells, a medium, and the like flowing inside the flow path F2 can flow into the circulation flow path F1 via the connection region X2.

<Division Processing Portion>

The division processing portion 40 is provided within the flow path F2, that is, in the middle of the flow path F2. The division processing portion 40 comprises a processing container 42 for performing division processing in which a cell aggregation generated by culturing the cells within the culture container 20 is divided. The division processing performed within the processing container 42 may be a mechanical division processing or may be enzymatic processing in which a cell dissociation enzyme is used. In a case where a mechanical division processing is applied, a mesh filter (not shown in the drawing) can be disposed inside the processing container 42. By making a cell aggregation pass through the mesh filter, the cell aggregation is divided into a size in accordance with the mesh size of the mesh filter. In contrast, in a case where division processing using enzymatic processing is applied, a cell dissociation enzyme such as trypsin-ethylenediaminetetraacetic acid (EDTA) can be accommodated in the processing container 42. The cell aggregation is divided by immersing the cell aggregation in the cell dissociation enzyme over a certain period of time.

The division processing portion 40 divides a cell aggregation flowing into the flow path F2 via the connection region X1 from the circulation flow path F1, in the processing container 42. The cells which have been subjected to the division processing flow out into the circulation flow path F1 via the connection region X2.

The division processing portion 40 comprises: a pressure container 41 communicating with the processing container 42; and a pressure adjustment mechanism 43 which adjusts the pressure within the pressure container 41 and the processing container 42. The pressure adjustment mechanism 43 pressurizes the atmosphere within the pressure container 41 and the processing container 42 by introducing air into the pressure container 41, or releases the atmosphere within the pressure container 41 and the processing container 42 into the air by discharging the atmosphere within the pressure container 41 to the outside. The pressure adjustment mechanism 43 allows cells which have been subjected to division processing to flow out into the circulation flow path F1 by increasing the pressure within the pressure container 41 and the processing container 42 more than the pressure within the circulation flow path F1.

An on-off valve V21 is provided in the vicinity of the connection region X1 in the pipe b1 forming the flow path F2. The on-off valve V21 is made to enter an open state in a case where cells or the like are transferred to the division processing portion 40 from the storage container 30, and is made to enter a closed state in other cases. On the other hand, an on-off valve V22 is provided in the vicinity of the connection region X2 in the pipe b2 forming the flow path F2. The on-off valve V22 is made to enter an open state in a case where cells or the like which have been subjected to division processing using the division processing portion 40 are made to flow out into the circulation flow path F1, and is made to enter a closed state in other cases.

An on-off valve V15 is provided on an upstream side of the connection region X2 and in the vicinity of the connection region X2 in the pipe a1 forming the circulation flow path F1. The on-off valve V15 is made to enter an open state in a case where cells, a medium, and the like are transferred to the storage container 30 from the culture container 20, and is made to enter a closed state in other cases.

<Stirring Portion>

Stirring portions 50, 51 and 52 each has a function of stirring a fluid flowing in. The stirring portions 50, 51, and 52 preferably have a configuration without a driving portion as a so-called static mixer, and can include, for example, a tubular body and a stirring element which is installed so as to be fixed inside the tubular body and forms a helical flow path inside the tubular body. The flow path inside the tubular body constituting the static mixer does not necessarily have a helical shape. The static mixer may have a structure in which a plate-like member forming the flow path inside the tubular body is appropriately disposed inside the tubular body or a structure in which the inner diameter of the tubular body is partially changed, so as to stir a fluid passing through the inside of the tubular body.

The stirring portion 50 is provided between the outflow port 32 of the storage container 30 and the inflow port 21 of the culture container 20 within the circulation flow path F1. More specifically, the stirring portion 50 is provided between the outflow port 32 of the storage container 30 and the connection region X1 within the circulation flow path F1. The stirring portion 50 may be provided between the connection region X1 and the inflow port 21 of the culture container 20 within the circulation flow path F1. The stirring portion 51 is provided between the medium supply portion 110 and the cell supply portion 100 within the flow path F3. The stirring portion 52 is provided on a downstream side of a region, to which a pipe from the cell supply portion 100 is connected, in the flow path F3.

<Filtration Device>

The cell culture device 1 includes a flow path F6 connecting the inflow port 31 and the outflow port 32 of the storage container 30. The flow path F6 is configured to include a pipe f1 connected to the circulation flow path F1 at a connection region X5 and a pipe f2 connected to the circulation flow path F1 at a connection region X6.

The filtration device 60 is provided within the flow path F6, that is, in the middle of the flow path F6. The inflow port 64 of the filtration device 60 is connected to the outflow port 32 of the storage container 30 via the pipe f2, and the outflow port 65 of the filtration device 60 is connected to the inflow port 31 of the storage container 30 via the pipe f1. The waste liquid collection container 16 is connected to the discharge flow path 67 of the filtration device 60. Pumps P10 and P11 disposed in the pipe f2 are driven in a case of performing the membrane separation processing in the filtration device 60. A liquid containing debris discharged to the permeation side of the filtration device 60 through the membrane separation processing is collected in the waste liquid collection container 16.

An on-off valve V51 is provided in the vicinity of the connection region X5 within the pipe f1 forming the flow path F6. In addition, an on-off valve V52 is provided in the vicinity of the connection region X6 within the pipe f2 forming the flow path F6. The on-off valves V51 and V52 are made to enter an open state during a period until a membrane-separated cell suspension which has been subjected to membrane separation processing in the filtration device 60 is collected in the storage container 30 and are made to enter a closed state in other cases.

A used medium, a used diluent, and a freezing liquid or the like accompanying the cells supplied from the cell supply portion 100 in a frozen state are included in the waste liquid collected in the waste liquid collection container 16. The form of the waste liquid collection container 16 is not particularly limited, and it is possible to use, for example, a container made of glass or stainless steel or a container having a form of a plastic bag.

<Freezing Portion>

The cell culture device 1 includes a flow path F5 including a pipe e1 connected to the circulation flow path F1 in the connection region X1. The freezing portion 17 is provided at an end portion of the flow path F5. The freezing portion 17 includes a preservation container 17a accommodating the cells flowing into the flow path F5 via the connection region X1 from the circulation flow path F1 together with a freezing liquid supplied from the freezing liquid supply portion 130. The preservation container 17a may have a form of, for example, a vial, a cryotube, or a bag. The freezing portion 17 can include a freezer freezing cells or a freezing liquid which have been accommodated in the preservation container 17a. In addition, the freezing portion 17 may comprise a tank filled with liquid nitrogen or may be constituted so as to accommodate the preservation container 17a in a tank. In addition, the freezing portion 17 may include, for example, a CRYO LIBRARY (registered trademark) system manufactured by TAIYO NIPPON SANSO CORPORATION. An on-off valve V41 is provided in the vicinity of the connection region X1 in the pipe e1 forming the flow path F5. The on-off valve V41 is made to enter an open state in a case where the cells and a freezing liquid are transferred into the freezing portion 17 from the storage container 30, and is made to enter a closed state in other cases. The connection position between the flow path F5 and the circulation flow path F1 may be any position as long as the position is between the outflow port 32 of the storage container 30 and the inflow port 21 of the culture container 20. In addition, in a case where it is unnecessary to cryopreserve the cells, it is possible to omit the freezing portion 17.

<Control Portion>

A control portion 18 integrally controls operations of the pumps P1 to P5, P10, and P11, the on-off valves V1 to V6, V11 to V16, V21, V22, V41, V51, and V52, the gas supply mechanism 25, and the pressure adjustment mechanisms 26, 33, and 43. Accordingly, culturing of cells in accordance with a predetermined cell culture protocol is automatically performed without human intervention. The electrical connection wiring between the control portion 18 and each of the above-described components controlled by the control portion 18 is not shown in FIG. 11 from the viewpoint of avoiding complications of the drawing.

Hereinafter, an example of a process which can be performed in the cell culture device 1 according to the present exemplary embodiment will be shown. The cell culture device 1 performs, for example, subculture processing, medium replacement processing, division processing, and freezing processing to be exemplified below. The subculture processing, medium replacement processing, division processing, and freezing processing to be described below are performed by the control portion 18 which controls operations of the on-off valves V1 to V6, V11 to V16, V21, V22, V31, V41, V51, and V52, the pumps P1 to P5, P10, and P11, and the pressure adjustment mechanisms 26, 33, and 43.

<Subculture Processing>

Figure 12:
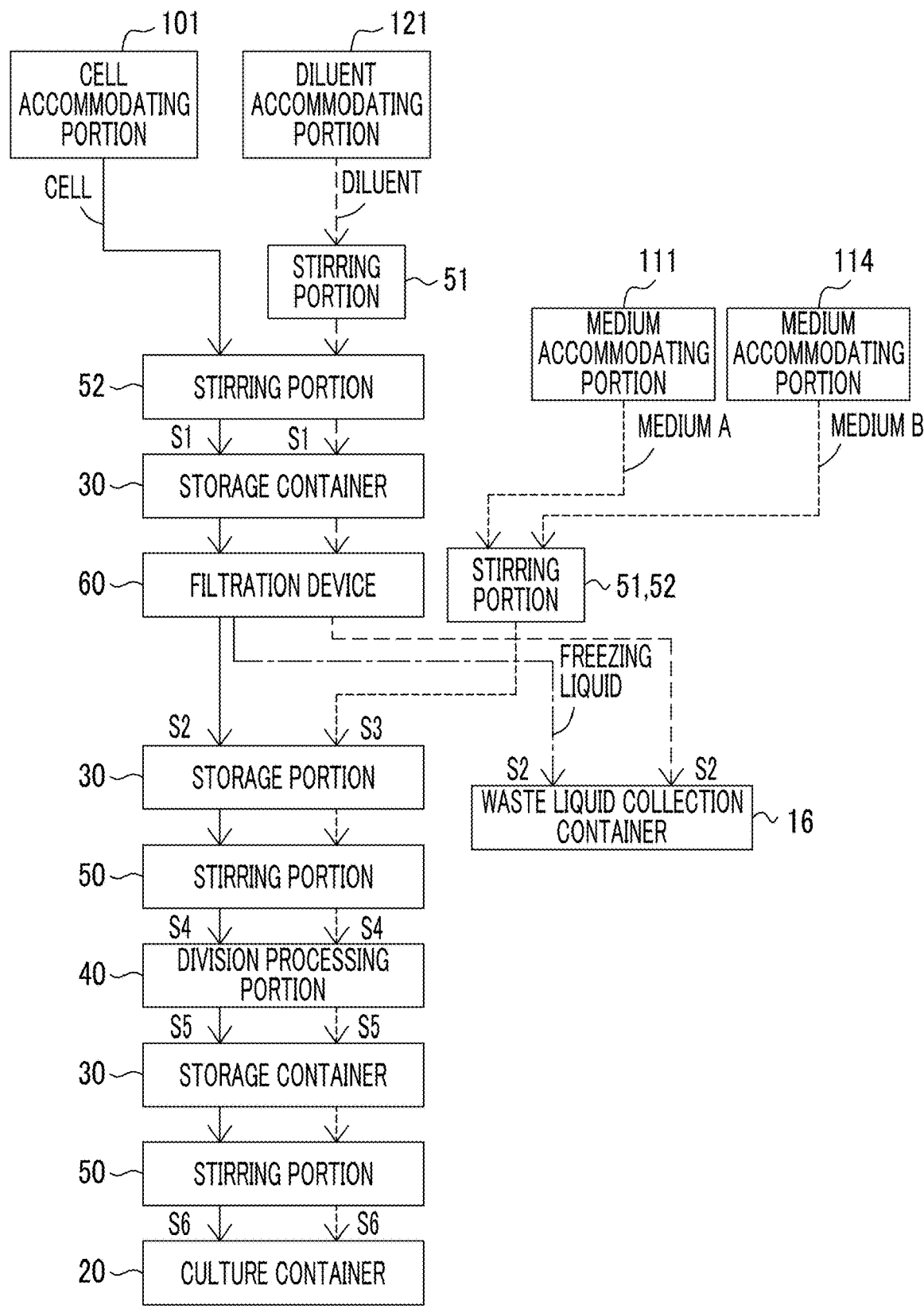
FIG. 12 is a view showing a flow of cells, a medium, and the like in a case where the cell culture device according to the exemplary embodiment of the present disclosure performs subculture processing.

The cell culture device 1 performs subculture processing of starting cell culture by accommodating cells accommodated in the cell accommodating portion 101 in the culture container 20 together with media accommodated in the medium accommodating portions 111 and 114, as follows. In the following description, a case where division processing in the division processing portion 40 is mechanical division processing will be exemplified. FIG. 12 is a view showing a flow of cells, media, and the like in a case where the cell culture device 1 performs subculture processing in the cell culture device. A correspondence between the flow of cells, media, and the like and each processing step shown below is shown in FIG. 12.

In Step S1, cells accommodated in the cell accommodating portion 101 in a frozen state and a diluent accommodated in the diluent accommodating portion 121 flow into the storage container 30 via the flow path F3 and the circulation flow path F1. The cells and the diluent are stirred and mixed with each other by passing through the stirring portion 52 within the flow path F3.

In Step S2, the on-off valves V51 and V52 are made to enter an open state and the pumps P10 and P11 are driven. Accordingly, the cell suspension which contains the cells stored in the storage container 30 and the freezing liquid and diluent accompanying the cells, flows into the filtration device 60. The filtration device 60 performs membrane separation processing of removing the freezing liquid and the diluent from the cell suspension containing the cells, the freezing liquid, and the diluent. The freezing liquid and the diluent are collected in the waste liquid collection container 16, and the cells subjected to the membrane separation processing are collected in the storage container 30.

In Step S3, media A and B accommodated in the medium accommodating portions 111 and 114 flow into the storage container 30 via the flow path F3 and the circulation flow path F1, and join the cells stored in the storage container 30. The media A and B are stirred and mixed with each other by passing through the stirring portions 51 and 52.

In Step S4, the cells and medium stored in the storage container 30 are transferred into the division processing portion 40 via the stirring portion 50. The cells flowing into the division processing portion 40 are subjected to division processing within the processing container 42. Accordingly, the cells in a frozen state are divided. In Step S5, the cells subjected to the division processing are transferred into the storage container 30 together with the medium.

In Step S6, the cells and the medium which are stored in the storage container 30 flow into the culture container 20 via the stirring portion 50. The cells and the medium are stirred and mixed with each other by passing through the stirring portion 50. Accordingly, the cells which have been supplied from the cell supply portion 100 are accommodated in the culture container 20 in a state where the distance between the cells in the medium becomes uniform.

In the above-described example, the membrane separation processing in the filtration device 60 is performed only once. However, the number of times of performing the membrane separation processing may be set to twice or more as necessary by repeatedly circulating the cell suspension between the storage container 30 and the filtration device 60.

<Medium Replacement Processing>

Figure 13:
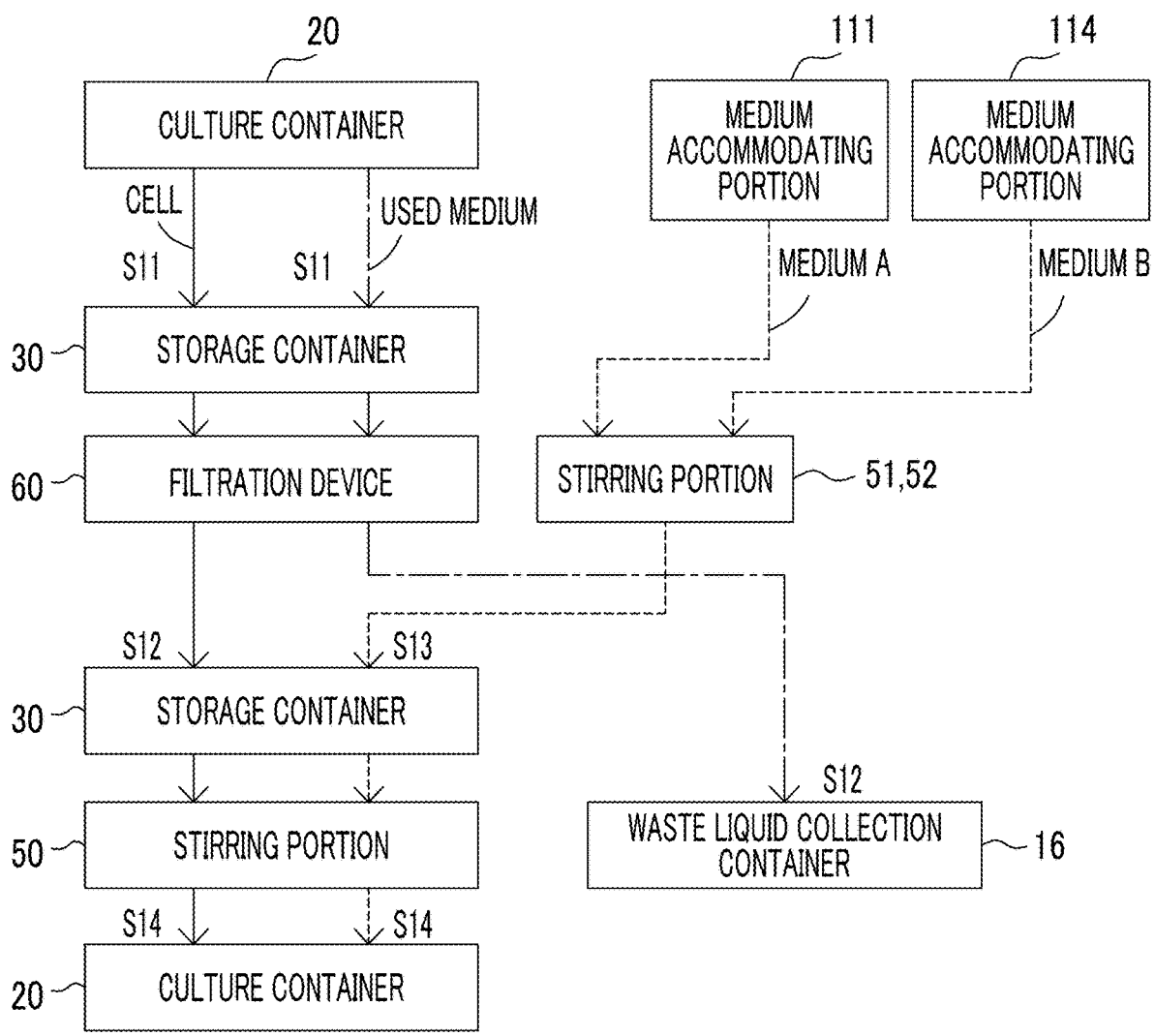
FIG. 13 is a view showing a flow of cells, a medium, and the like in a case where the cell culture device according to the exemplary embodiment of the present disclosure performs medium replacement processing.

In cell culture, a medium is deteriorated due to dead cells or metabolites of proteins secreted from cells. For this reason, a medium replacement processing of replacing a used medium in the culture container 20 with a fresh medium at an appropriate timing within the culture period is required. The cell culture device 1 according to the present exemplary embodiment performs the above-described medium replacement processing as follows. FIG. 13 is a view showing a flow of cells, media, and the like in a case where the cell culture device 1 performs the medium replacement processing. A correspondence between the flow of cells, media, and the like and each processing step shown below is shown in FIG. 13.

In Step S11, the used medium containing cells and debris is transferred from the culture container 20 into the storage container 30. In Step S12, the on-off valves V51 and V52 are made to enter an open state and the pumps P10 and P11 are driven. Accordingly, the cell suspension which contains the cells and the used medium stored in the storage container 30 flows into the filtration device 60. The filtration device 60 performs membrane separation processing in which the used medium containing debris is removed from the cell suspension containing the cells and the used medium. The used medium is collected in the waste liquid collection container 16, and the cells subjected to the membrane separation processing are collected in the storage container 30.

In Step S13, fresh media A and B accommodated in the medium accommodating portions 111 and 114 flow into the storage container 30 via the flow path F3 and the circulation flow path F1, and join the cells stored in the storage container 30. The media A and B are stirred and mixed with each other by passing through the stirring portions 51 and 52.

In Step S14, the cells and the fresh medium which are stored in the storage container 30 flow into the culture container 20 via the stirring portion 50. The cells and the fresh medium are stirred and mixed with each other by passing through the stirring portion 50. Accordingly, the cells are accommodated in the culture container 20 in a state where the distance between the cells floating in the medium becomes uniform.

In the above-described example, the membrane separation processing in the filtration device 60 is performed only once. However, the number of times of performing the membrane separation processing may be set to twice or more as necessary by repeatedly circulating the cell suspension containing the cells and the used medium between the storage container 30 and the filtration device 60.

<Division Processing>

During culture of pluripotent stem cells, in a case where the sizes of cell aggregations called spheres generated through culturing cells become too large, problems may arise such that cells start differentiation due to an adhesive fusion of the cell aggregations or such that cells in central portions of cell aggregations necrose.

Figure 14:
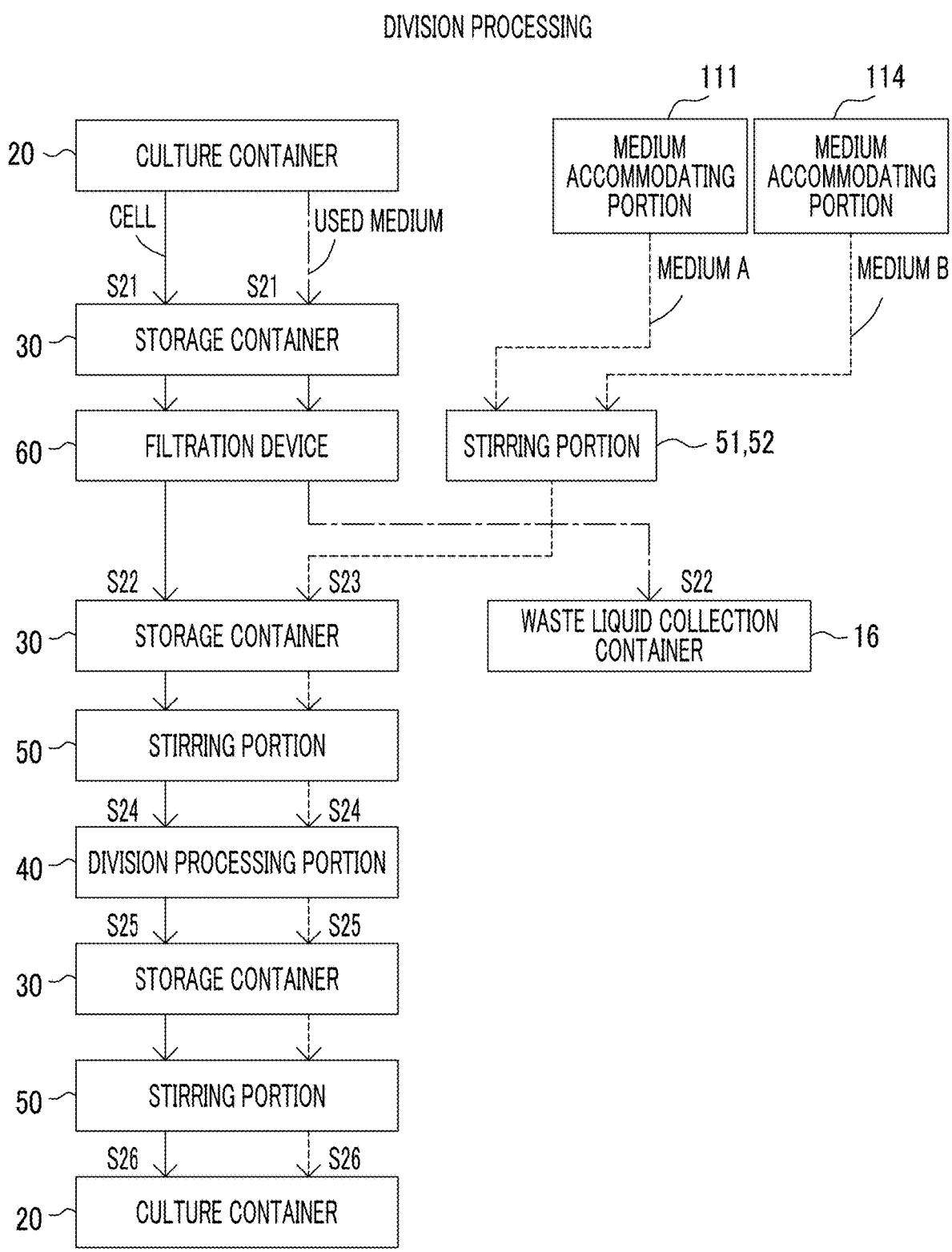
FIG. 14 is a view showing a flow of cells, a medium, and the like in a case where the cell culture device according to the exemplary embodiment of the present disclosure performs division processing.

Accordingly, in some cases, division processing in which a cell aggregation is divided at an appropriate timing during a culture period is necessary in order to prevent the size of the cell aggregation from becoming too large. In the cell culture device 1 according to the present exemplary embodiment, the above-described division processing is performed as follows. In the following description, a case where the division processing in the division processing portion 40 is mechanical division processing, will be exemplified. FIG. 14 is a view showing a flow of cells, media, and the like in a case where the cell culture device 1 performs division processing. A correspondence between the flow of cells, media, and the like and each processing step shown below is shown in FIG. 14.

In Step S21, the cells and the used medium are transferred from the culture container 20 into the storage container 30. In Step S22, the on-off valves V51 and V52 are made to enter an open state and the pumps P10 and P11 are driven. Accordingly, the cell suspension which contains the cells and the used medium stored in the storage container 30 flows into the filtration device 60. The filtration device 60 performs membrane separation processing in which the used medium is removed from the cell suspension containing the cells and the used medium. The used medium is collected in the waste liquid collection container 16, and the cells subjected to the membrane separation processing are collected in the storage container 30.

In Step S23, fresh media A and B accommodated in the medium accommodating portions 111 and 114 flow into the storage container 30 via the flow path F3 and the circulation flow path F1, and join the cells stored in the storage container 30. The media A and B are stirred and mixed with each other by passing through the stirring portions 51 and 52.

In Step S24, the cells and the fresh medium stored in the storage container 30 are transferred into the division processing portion 40, and division processing is performed on cell aggregations in the division processing portion 40. In Step S25, the cells subjected to the division processing are transferred into the storage container 30 together with the medium.

In Step S26, the cells and the medium which are stored in the storage container 30 flow into the culture container 20 via the stirring portion 50. The cells and the medium are stirred and mixed with each other by passing through the stirring portion 50. Accordingly, the cells are accommodated in the culture container 20 in a state where the distance between the cells floating in the medium becomes uniform.

In the above-described example, the membrane separation processing in the filtration device 60 is performed only once. However, the number of times of performing the membrane separation processing may be set to twice or more as necessary by repeatedly circulating the cell suspension containing the cells and the used medium between the storage container 30 and the filtration device 60. In addition, in the above-described example, the membrane separation processing and supply of a fresh medium are performed in the filtration device 60 before the division processing, but the membrane separation processing and the supply of a fresh medium may be performed in the filtration device 60 after the division processing.

<Freezing Processing>

Figure 15:
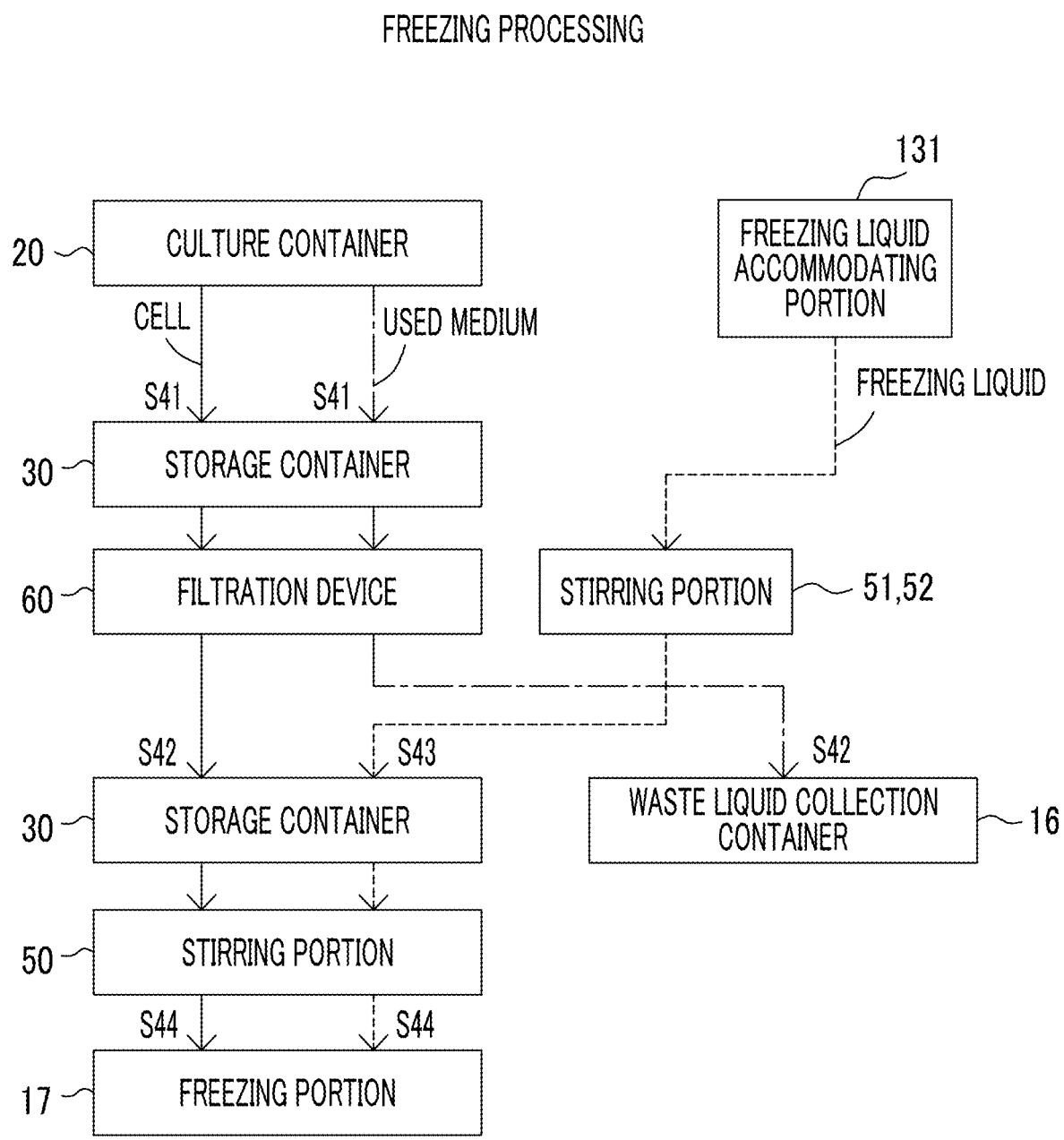
FIG. 15 is a view showing a flow of cells, a medium, and the like in a case where the cell culture device according to the exemplary embodiment of the present disclosure performs freezing processing.

In a case of preservation after collecting the cells which have been cultured, cells are generally collected in a preservation container for cryopreservation. The cell culture device 1 according to the present exemplary embodiment performs freezing processing, in which cultured cells are collected and frozen, as follows. FIG. 15 is a view showing a flow of cells, media, and the like in a case where the cell culture device 1 performs freezing processing. A correspondence between the flow of cells, media, and the like and each processing step shown below is shown in FIG. 15.

In Step S41, the cells and the used medium are transferred from the culture container 20 into the storage container 30. In Step S42, the on-off valves V51 and V52 are made to enter an open state and the pumps P10 and P11 are driven. Accordingly, the cell suspension which contains the cells and the used medium stored in the storage container 30 flows into the filtration device 60. The filtration device 60 performs membrane separation processing in which the used medium is removed from the cell suspension containing the cells and the used medium. The used medium is collected in the waste liquid collection container 16, and the cells subjected to the membrane separation processing are collected in the storage container 30.

In Step S43, a freezing liquid accommodated in the freezing liquid accommodating portion 131 flows into the storage container 30 via the flow path F3 and the circulation flow path F1, and join the cells stored in the storage container 30. The freezing liquid is stirred by passing through the stirring portions 51 and 52.

In Step S44, the cells and the freezing liquid stored in the storage container 30 are accommodated in the preservation container 17*a* of the freezing portion 17 via the stirring portion 50 and the flow path F5. The cells and the freezing liquid are stirred and mixed with each other by passing through the stirring portion 50. The freezing portion 17 freezes the cells accommodated in the preservation container 17*a* together with the freezing liquid.

In the above-described example, the membrane separation processing in the filtration device 60 is performed only once. However, the number of times of performing the membrane separation processing may be set to twice or more as necessary by repeatedly circulating the cell suspension containing the cells and the used medium between the storage container 30 and the filtration device 60.

<Cell Culture Processing>

Figure 16:
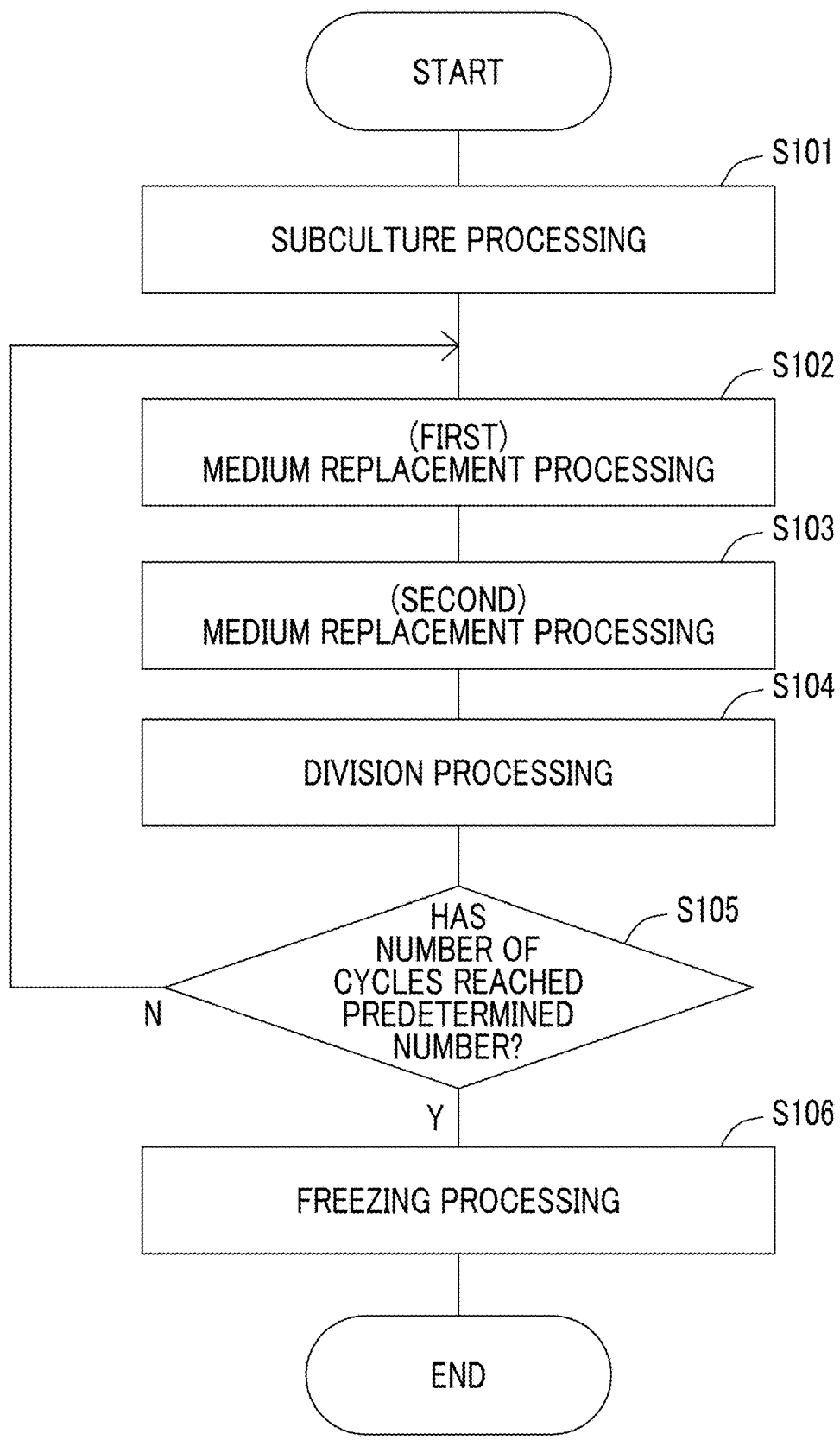
FIG. 16 is a flowchart showing a flow of processing in a cell culture program executed by a control portion according to the exemplary embodiment of the present disclosure.

The cell culture device 1 can automatically perform cell culture without human intervention using the control portion 18 executing a cell culture processing program exemplified below. FIG. 16 is a flowchart showing a flow of processing of the cell culture program executed by the control portion 18.

In Step S101, the control portion 18 performs the above-described subculture processings to start cell culture by accommodating cells supplied from the cell supply portion 100 and a medium supplied from the medium supply portion 110 in the culture container 20.

In Step S102, the used media in the culture container 20 are replaced with fresh media accommodated in the medium accommodating portions 111 and 114 and the cell culture is continued by the control portion 18 performing the above-described (first) medium replacement processing after a predetermined period of time elapses from the start of the cell culture.

In Step S103, the used media in the culture container 20 are replaced with fresh media accommodated in the medium accommodating portions 111 and 114 and the cell culture is continued by the control portion 18 performing the above-described (second) medium replacement processing after a predetermined period of time elapses from the execution of the first medium replacement processing.

In Step S104, the control portion 18 divides cell aggregations and the cell culture is continued by performing the above-described division processing after a predetermined period of time elapses from the execution of the second medium replacement processing.

In Step S105, the control portion 18 determines whether or not the number of culture cycles, in which the processing in the above-described processing of Steps S102 to S104 is regarded as one cycle, has reached a predetermined number. In a case where it is determined that the number of culture cycles has not reached the predetermined number, the control portion 18 returns the process back to Step S102. In contrast, in a case where it is determined that the number of culture cycles has reached the predetermined number, the control portion 18 advances the process to Step S106. The scale of the cell culture increases in accordance with the progress of the culture cycles.

In step S106, the cultured cells are accommodated in the preservation container 17*a* of the freezing portion 17 and cryopreserved by the control portion 18 performing the above-described freezing processing.

In the above-described example, the medium replacement processing has been performed twice within one culture cycle. However, the number of times of performing the medium replacement processing within one culture cycle can be appropriately changed.

According to the cell culture device 1 of the present exemplary embodiment, it is possible to continuously perform a series of processings, such as medium replacement processing and division processing, which are required for cell culture, in a closed system. Accordingly, this enables mass production of homogeneous cells. According to the cell culture device 1 of the present exemplary embodiment, it is possible to perform a series of processings from the subculture processing to the freezing processing required for cell culture without manual intervention. The cell culture device 1 according to the present exemplary embodiment can also be used for culturing cells other than pluripotent stem cells and cells derived from pluripotent stem cells.

Second Exemplary Embodiment

The membrane separation method according to the present disclosure can be applied to cell culture for expressing antibodies in non-human cells. By using the membrane separation method of the present disclosure, it is possible to enhance the efficiency of expressing antibodies by removing debris from a cell suspension containing non-human cells which have been cultured in a culture container.

Cells used for expressing antibodies are not particularly limited, but examples thereof include animal cells (non-human cells), eukaryotic cells such as plant cells and yeast, prokaryotic cells such as *Bacillus subtilis*, and *Escherichia coli*. Animal cells (non-human cells) such as CHO cells, BHK-21 cells, and SP2/0-Ag14 cells are preferable, and CHO cells are more preferable.

Antibodies to be expressed in non-human cells are not particularly limited, but examples thereof include an anti-IL-6 receptor antibody, an anti-IL-6 antibody, an anti-glypican-3 antibody, an anti-CD3 antibody, an anti-CD20 antibody, an anti-GPIIb/IIIa antibody, an anti-TNF antibody, an anti-CD25 antibody, an anti-EGFR antibody, an anti-Her2/neu antibody, an anti-RSV antibody, an anti-CD33 antibody, an anti-CD52 antibody, an anti-IgE antibody, an anti-CD11a antibody, an anti-VEGF antibody, and an anti-VLA4 antibody. Antibodies include not only monoclonal antibodies derived from animals such as humans, mice, rats, hamsters, rabbits, and monkeys, but also artificially modified antibodies such as chimeric antibodies, humanized antibodies, and bispecific antibodies.

Obtained antibodies or fragments thereof can be homogeneously purified. Separation and purification methods used for ordinary polypeptides may be used for separation and purification of antibodies or fragments thereof. For example, separation and purification of antibodies can be performed by appropriately selecting and combining chromatography columns of affinity chromatography or the like, filters, ultrafiltration, salting-out, dialysis, SDS polyacrylamide gel electrophoresis, and isoelectric focusing phoresis, but the present invention is not limited thereto. The concentration of obtained antibodies can be measured through measurement of absorbance, enzyme-linked immunosorbent assay (ELISA), or the like.

FIG. 17 is a view showing a configuration of a cell culture device 2 according to a second exemplary embodiment of the present disclosure which performs cell culture for expressing antibodies in non-human cells while appropriately performing membrane separation processing. The cell culture device 2 is configured to include a filtration device 60C, a cell culture container 610, a medium accommodating portion 620, and a collection container 630.

The basic configuration of the filtration device 60C is the same as that of the filtration device 60 (refer to FIG. 1) according to the above-described first exemplary embodiment. The filtration device 60C is a device for performing membrane separation processing of a cell suspension in which non-human cells as single cells capable of expressing antibodies are separated from debris using the filtration membrane 600.

The filtration device 60C comprises the filtration membrane 600 separating the space inside the container into a supply side 604 and a permeation side 605. The typical structure of the filtration membrane 600 is the same as that of the filtration membrane 61 shown in FIG. 2. Hereinafter, in a case of mentioning the structure of the filtration membrane 600, FIG. 2 may be appropriately referred to. A twill weave mesh 61A formed by twill-weaving a fibrous member as shown in FIG. 3A can be suitability used as the filtration membrane 600, for example. In addition, it is possible to suitably use, for example, a laminated mesh 61D, which is formed by laminating two sheets of plain weave meshes 61*b* and 61*c* as shown in FIG. 4, as the filtration membrane 600.

The filtration device 60C includes: circulation ports 601 and 602 for allowing a cell suspension to flow into and out from the supply side 604; and a discharge port 603 for discharging debris discharged to the permeation side 605 to the collection container 630. One end of a pipe T2 is connected to the circulation port 601, and the other end of the pipe T2 is connected to the cell culture container 610. In addition, one end of a pipe T1 is connected to the circulation port 602, and the other end of the pipe T1 is connected to a reciprocating pump P101. One end of a pipe T3 is connected to the discharge port 603, and the other end of the pipe T3 is connected to the collection container 630. A withdrawing pump P103 is provided on the pipe T3. The cell culture container 610 and the medium accommodating portion 620 are connected to each other by a pipe T4, and a liquid feeding pump P102 is provided on the pipe T4. The pipes T1 to T4 are composed of, for example, a tubular member such as a silicon tube.

The cell culture device 2 comprises pressure sensors 701 to 703, and the gauge pressure of each portion is monitored. The pressure sensor 701 monitors the gauge pressure in the vicinity of the circulation port 602 in the pipe T1. The pressure sensor 702 monitors the gauge pressure in the vicinity of the circulation port 601 in the pipe T2. The pressure sensor 703 monitors the gauge pressure in the vicinity of the discharge port 603 in the pipe T3. That is, the gauge pressure applied to the surface of the filtration membrane 600 on the supply side 604 is monitored by the pressure sensors 701 and 702, and the gauge pressure applied to the surface of the filtration membrane 600 on the permeation side 605 is monitored by the pressure sensor 703.

In the cell culture container 610, non-human cells as single cells capable of expressing antibodies are cultured. The filtration device 60C performs membrane separation processing of a cell suspension containing debris and non-human cells cultured in cell culture container 610.

By operating the reciprocating pump P101, the liquid feeding pump P102, and the withdrawing pump P103, the cell suspension in the cell culture container 610 flows into the filtration device 60C from the circulation port 601. By the reciprocating operation of the reciprocating pump P101, the cell suspension flowing into the filtration device 60C reciprocates along the surface of the filtration membrane 600 on the supply side 604. While the cell suspension is flowing on the filtration membrane 600, debris which is contained in the cell suspension and has a relatively small size permeates through the filtration membrane 600 together with a liquid such as a medium and is discharged to the permeation side 605. The debris discharged to the permeation side 605 is collected into the collection container 630 via the pipe T3. On the other hand, non-human cells as single cells which are contained in the cell suspension and have relatively large sizes are collected into the cell culture container 610 without permeating through the filtration membrane 600. A fresh medium in an amount corresponding to the amount of filtrate collected in the collection container 630 is supplied to the cell culture container 610 from the medium accommodating portion 620.

By using the filtration membrane 600 in the membrane separation processing for separating non-human cells as single cells from debris, non-human cells flowing along the surface of the filtration membrane 600 on the supply side 604 of the filtration device 60C can enter the filtration membrane 600 from the opening OP1 (refer to FIG. 2) on the supply side. However, since the opening OP2 (refer to FIG. 2) on the permeation side of the filtration membrane 600 is disposed at a position deviated from the opening OP1 on the supply side, or since the path connecting the opening OP1 to the opening OP2 is nonlinear, the non-human cells which have entered the filtration membrane 600 cannot easily flow out to the permeation side compared to the debris. On the other hand, since the size of the debris is smaller than those of the non-human cells, the debris can easily flow out to the permeation side of the filtration membrane 600. In addition, the debris can flow out to the permeation side through a side of a non-human cell which has entered the opening OP1 of the filtration membrane 600. According to the filtration membrane 600 of the present exemplary embodiment, since the opening OP2 on the permeation side is disposed at a position deviated from the opening OP1 on the supply side or the path connecting the opening OP1 to the opening OP2 or is nonlinear, the flowing out of the non-human cell, which has entered the filtration membrane 600, to the permeation side is suppressed, and therefore, it is possible to appropriately separate the non-human cell from the debris. In addition, according to the filtration membrane 600 according to the present exemplary embodiment, since it is difficult for the non-human cell to enter a deep portion of the filtration membrane 600 in a thickness direction, it is possible to suppress blocking (clogging) of the filtration membrane 600 and to reduce damage to non-human cells in the membrane separation processing.

In a case of separating non-human cells from debris using the filtration membrane 600, the diameters of the openings OP1 and OP2 (refer to FIG. 2) of the filtration membrane 600 are preferably 0.1 to 2 times, more preferably 0.15 to 1 times, and still more preferably 0.2 to 0.8 times the diameters of the non-human cells. By setting the diameters of the openings OP1 and OP2 to be greater than or equal to 0.1 times the diameters of non-human cells, it is possible to appropriately discharge debris among the non-human cells and the debris which are contained in a cell suspension to the permeation side. By setting the diameters of the openings OP1 and OP2 to be less than or equal to 2 times the diameters of the non-human cells, it is possible to suppress the non-human cells from being caught on the surface of the filtration membrane 600 and to suppress the non-human cells from flowing out to the permeation side.

In the case of separating non-human cells from debris using the filtration membrane 600, it is preferable to secure the uniformity of the diameters of the openings OP1 and OP2 (refer to FIG. 2) of the filtration membrane 600. That is, when an average value of distribution of the diameters of the openings OP1 and OP2 of the filtration membrane 600 is set to X and a standard deviation is set to $\sigma$, the fluctuation rate represented by $\sigma/X$ preferably satisfies $0 < \sigma/X \leq 0.1$, more preferably satisfies $0 < \sigma/X \leq 0.05$, and still more preferably satisfies $0 < \sigma/X \leq 0.02$. By satisfying $0 < \sigma/X \leq 0.1$, it is possible to discharge the debris to the permeation side while suppressing the discharge of the non-human cells to the permeation side. $\sigma$ and X can be measured through a mercury intrusion method and can be obtained by a known statistical analysis method.

It is preferable to set the membrane surface differential pressure as the difference between the pressure applied to the surface on the supply side 604 of the filtration membrane 600 and the pressure applied to the surface of the permeation side 605 of the filtration membrane 600 to 0.01 kilopascals to 60 kilopascals while performing the membrane separation processing of a cell suspension using the filtration device 60C. By setting the membrane surface differential pressure of the filtration membrane 600 to be greater than or equal to 0.01 kilopascals, it is possible to appropriately discharge the debris from the supply side to the permeation side. In addition, by setting the membrane surface differential pressure of the filtration membrane 600 to be less than or equal to 60 kilopascals, it is possible to perform the membrane separation processing while suppressing non-human cells from being divided (crushed) by the filtration membrane.

In a case of separating non-human cells from debris using the filtration membrane 600, the thickness of the filtration membrane 600 is preferably less than or equal to 150 μm, more preferably less than or equal to 100 μm, and still more preferably less than or equal to 80 μm. By setting the thickness of the filtration membrane 600 to be less than or equal to 150 μm, the risk of clogging and the risk of damage to cells can be reduced by supplementing cells using the filtration membrane 600.

In the case of separating non-human cells from debris using the filtration membrane 600, the gauge pressure applied to the supply side 604 of the filtration membrane 600 is preferably −70 kilopascals to 70 kilopascals, more preferably −40 kilopascals to 40 kilopascals, and still more preferably −20 kilopascals to 20 kilopascals. By setting the gauge pressure applied to the supply side 604 of the filtration membrane 600 to −70 kilopascals to 70 kilopascals, the risk of damage non-human cells can be reduced.

In the case of separating non-human cells from debris using the filtration membrane 600, the diameters of the non-human cells as single cells are preferably 5 μm to 25 μm, more preferably 7 μm to 22 μm, and still preferably 8 μm to 20 μm. By setting the diameters of non-human cells to 5 μm to 25 μm, membrane separation between non-human cells and debris becomes easy.

In the case of separating non-human cells from debris using the filtration membrane 600, the number density [cells/ml] of non-human cells which are contained in a filtrate that has permeated through the filtration membrane 600 is preferably less than or equal to 50% of the number density [cells/ml] of non-human cells contained in a cell suspension before permeating through the filtration membrane 600, more preferably less than or equal to 20% thereof, and still more preferably less than or equal to 5% thereof.

In the case of separating non-human cells from debris using the filtration membrane 600, the number density [cells/ml] of debris which is contained in a filtrate that has permeated through the filtration membrane 600 and has a diameter of 1/10 to 1/2 of the diameters of the non-human cells is preferably 50% to 100% of the number density [cells/ml] of debris having a diameter of 1/10 to 1/2 of the diameters of the non-human cells contained in the cell suspension before permeating through the filtration membrane 600, more preferably 70% to 100% thereof, and still more preferably 80% to 100% thereof.

In addition, when the amount of cell suspension in the cell culture container 610 in the cell culture device 2 shown in FIG. 17 is set to L and the amount of a filtrate that has permeated through the filtration membrane 600 per day in membrane separation processing is set to N, 0.1≤N/L≤6 is preferably satisfied, 0.15≤N/L≤5 is more preferably satisfied, and 0.2≤N/L≤4.5 is still more satisfied. By satisfying 0.1≤N/L≤6, debris can be efficiently withdrawn from the cell suspension contained in the cell culture container 610, and the risk of damage to cells can be reduced.

Third Exemplary Embodiment

The membrane separation method according to the present disclosure can be applied to cell culture for producing platelets in megakaryocytes. By using the membrane separation method of the present disclosure, it is possible to separate and collect platelets by separating platelets from a cell suspension containing platelets and megakaryocytic cells which have been cultured in a culture container. By culturing megakaryocytic cells having an ability of producing platelets in the culture container after separation of platelets, it is possible to increase the total capacity of platelets obtained after the culture.

Megakaryocytes and platelets may be megakaryocytes and platelets collected from adult tissues, may be megakaryocytes and platelets differentiated from cells, such as pluripotent stem cells, hematopoietic precursor cells, and mesenchymal cells, which have differentiation potency, may be megakaryocytes and platelets produced in cells having no differentiation potency into megakaryocytes using a direct reprogramming technique as a usual method, or may be a combination thereof.

The organism species from which megakaryocytes and platelets are derived are not particularly limited, but are preferably mammals (for example, humans, mice, rats, hamsters, guinea pigs, sheep, pigs, and monkeys), and more preferably humans.

Examples of pluripotent stem cells include embryonic stem cells (ES cells), nuclear transplantation embryonic stem cells (ntES cells), and induced pluripotent stem cells (iPS cells), but are not limited thereto.

Examples of the hematopoietic precursor cells include bone marrow-derived cells, umbilical cord blood-derived cells, (G-CSF-)mobilized peripheral blood-derived cells, ES cell-derived mesodermal cells, or peripheral blood-derived cells, but are not limited thereto. Examples of these hematopoietic precursor cells include CD34-positive cells (for example, $CD34^+$ cells, $CD133^+$ cells, SP cells, $CD34^+$ $CD38^-$ cells, and $c\text{-}kit^+$ cells, or those exhibiting $CD3^-$, $CD4^-$, $CD8^-$, and $CD34^+$) (WO2004/110139A).

Examples of mesenchymal cells include mesenchymal stem cells and adipose precursor cells, but are not limited thereto.

Examples of cells having no differentiation potency into megakaryocytes in an ordinary method include fibroblasts, but are not limited thereto.

Methods for producing megakaryocytes and platelets by differentiating cells such as pluripotent stem cells, hematopoietic precursor cells, and mesenchymal cells, having differentiation potency may be performed according to methods commonly known to those skilled in the art, and are not particularly limited thereto. By culturing cells having differentiation potency under appropriate culture conditions using a medium for inducing differentiation which is suitable differentiating the cells into megakaryocytes, it is possible to differentiate the cells having differentiation potency into megakaryocytes, and therefore, platelets are produced from the megakaryocytes. As a method for producing megakaryocytes and platelets using a direct reprogramming technique on cells having no differentiation potency into megakaryocytes in a usual method, it is possible to perform differentiation into megakaryocytes by differentiating the cells having no differentiation potency into megakaryocytes in a usual method, by performing gene introduction so as to express genes inducing to megakaryocytes or by adding specific nucleic acids, proteins, low molecular compounds, and the like to a culture solution.

FIG. 17 is a view showing a configuration of a cell culture device 2 according to a third exemplary embodiment of the present disclosure which performs cell culture for producing platelets in megakaryocytic cells while appropriately performing membrane separation processing. The cell culture device 2 is configured to include a filtration device 60C, a cell culture container 610, a medium accommodating portion 620, and a collection container 630.

The basic configuration of the filtration device 60C is the same as that of the filtration device 60 (refer to FIG. 1) according to the above-described first exemplary embodiment. The filtration device 60C is a device for performing membrane separation processing of a cell suspension in which megakaryocytic cells as single cells capable of producing platelets are separated from platelets using the filtration membrane 600.

The filtration device 60C comprises the filtration membrane 600 separating the space inside the container into a supply side 604 and a permeation side 605. The typical structure of the filtration membrane 600 is the same as that of the filtration membrane 61 shown in FIG. 2. Hereinafter, in a case of mentioning the structure of the filtration membrane 600, FIG. 2 may be appropriately referred to. A twill weave mesh 61A formed by twill-weaving a fibrous member as shown in FIG. 3A can be suitability used as the filtration membrane 600, for example. In addition, it is possible to suitably use, for example, a laminated mesh 61D, which is formed by laminating two sheets of plain weave meshes 61b and 61c as shown in FIG. 4, as the filtration membrane 600.

The filtration device 60C includes: circulation ports 601 and 602 for allowing a cell suspension to flow into and out from the supply side 604; and a discharge port 603 for discharging platelets discharged to the permeation side 605 to the collection container 630. One end of a pipe T2 is connected to the circulation port 601, and the other end of the pipe T2 is connected to the cell culture container 610. In addition, one end of a pipe T1 is connected to the circulation port 602, and the other end of the pipe T1 is connected to a reciprocating pump P101. One end of a pipe T3 is connected to the discharge port 603, and the other end of the pipe T3 is connected to the collection container 630. A withdrawing pump P103 is provided on the pipe T3. The cell culture container 610 and the medium accommodating portion 620 are connected to each other by a pipe T4, and a liquid feeding pump P102 is provided on the pipe T4. The pipes T1 to T4 are composed of, for example, a tubular member such as a silicon tube.

The cell culture device 2 comprises pressure sensors 701 to 703, and the gauge pressure of each portion is monitored. The pressure sensor 701 monitors the gauge pressure in the vicinity of the circulation port 602 in the pipe T1. The pressure sensor 702 monitors the gauge pressure in the vicinity of the circulation port 601 in the pipe T2. The pressure sensor 703 monitors the gauge pressure in the vicinity of the discharge port 603 in the pipe T3. That is, the gauge pressure applied to the surface of the filtration membrane 600 on the supply side 604 is monitored by the pressure sensors 701 and 702, and the gauge pressure applied to the surface of the filtration membrane 600 on the permeation side 605 is monitored by the pressure sensor 703.

In the cell culture container 610, megakaryocytic cells as single cells capable of producing platelets are cultured. The filtration device 60C performs membrane separation processing of a cell suspension containing platelets and megakaryocytic cells cultured in cell culture container 610.

By operating the reciprocating pump P101, the liquid feeding pump P102, and the withdrawing pump P103, the cell suspension in the cell culture container 610 flows into the filtration device 60C from the circulation port 601. By the reciprocating operation of the reciprocating pump P101, the cell suspension flowing into the filtration device 60C reciprocates along the surface of the filtration membrane 600 on the supply side 604. While the cell suspension is flowing on the filtration membrane 600, platelets which are contained in the cell suspension and have relatively small sizes permeate through the filtration membrane 600 together with a liquid such as a medium and are discharged to the permeation side 605. The platelets discharged to the permeation side 605 are collected into the collection container 630 via the pipe T3. On the other hand, megakaryocytic cells as single cells which are contained in the cell suspension and have relatively large sizes are collected into the cell culture container 610 without permeating through the filtration membrane 600. A fresh medium in an amount corresponding to the amount of filtrate collected in the collection container 630 is supplied to the cell culture container 610 from the medium accommodating portion 620.

By using the filtration membrane 600 in the membrane separation processing for separating megakaryocytic cells as single cells from platelets, megakaryocytic cells flowing along the surface of the filtration membrane 600 on the supply side 604 of the filtration device 60C can enter the filtration membrane 600 from the opening OP1 (refer to FIG. 2) on the supply side. However, since the opening OP2 (refer to FIG. 2) on the permeation side of the filtration membrane 600 is disposed at a position deviated from the opening OP1 on the supply side, or since the path connecting the opening OP1 to the opening OP2 is nonlinear, the megakaryocytes which have entered the filtration membrane 600 cannot easily flow out to the permeation side compared to the platelets. On the other hand, since the sizes of the platelets are smaller than those of the megakaryocytic cells, the platelets can easily flow out to the permeation side of the filtration membrane 600. In addition, the platelets can flow out to the permeation side through sides of megakaryocytic cells which have entered the opening OP1 of the filtration membrane 600. According to the filtration membrane 600 of the present exemplary embodiment, since the opening OP2 on the permeation side is disposed at a position deviated from the opening OP1 on the supply side or the path connecting the opening OP1 to the opening OP2 or is nonlinear, the flowing out of the megakaryocytic cells, which have entered the filtration membrane 600, to the permeation side is suppressed, and therefore, it is possible to appropriately separate the megakaryocytic cells from the platelets. In addition, according to the filtration membrane 600 according to the present exemplary embodiment, since it is difficult for the megakaryocytic cells to enter a deep portion of the filtration membrane 600 in a thickness direction, it is possible to suppress blocking (clogging) of the filtration membrane 600 and to reduce damage to megakaryocytic cells in the membrane separation processing.

In a case of separating megakaryocytic cells from platelets using the filtration membrane 600, the diameters of the openings OP1 and OP2 (refer to FIG. 2) of the filtration membrane 600 are preferably 0.05 to 2 times, more preferably 0.1 to 1 times, and still more preferably 0.1 to 0.8 times the diameters of the megakaryocytic cells. By setting the diameters of the openings OP1 and OP2 to be greater than or equal to 0.05 times the diameters of megakaryocytic cells, it is possible to appropriately discharge platelets among the megakaryocytic cells and the platelets which are contained in a cell suspension to the permeation side. By setting the diameters of the openings OP1 and OP2 to be less than or equal to 2 times the diameters of the megakaryocytic cells, it is possible to suppress the megakaryocytic cells from being caught on the surface of the filtration membrane 600 and to suppress the megakaryocytic cells from flowing out to the permeation side.

In the case of separating megakaryocytic cells from platelets using the filtration membrane 600, it is preferable to secure the uniformity of the diameters of the openings OP1 and OP2 (refer to FIG. 2) of the filtration membrane 600. That is, when an average value of distribution of the diameters of the openings OP1 and OP2 of the filtration membrane 600 is set to X and a standard deviation is set to σ, the fluctuation rate represented by σ/X preferably satisfies 0<σ/X≤0.1, more preferably satisfies 0<σ/X≤0.05, and still more preferably satisfies 0<σ/X≤0.02. By satisfying 0<σ/X≤0.1, it is possible to discharge the platelets to the permeation side while suppressing the discharge of the megakaryocytic cells to the permeation side. σ and X can be measured through a mercury intrusion method and can be obtained by a known statistical analysis method.

It is preferable to set the membrane surface differential pressure as the difference between the pressure applied to the surface on the supply side 604 of the filtration membrane 600 and the pressure applied to the surface of the permeation side 605 of the filtration membrane 600 to 0.01 kilopascals to 60 kilopascals while performing the membrane separation processing of a cell suspension using the filtration device 60C. By setting the membrane surface differential pressure of the filtration membrane 600 to be greater than or equal to 0.01 kilopascals, it is possible to appropriately discharge the platelets from the supply side to the permeation side. In addition, by setting the membrane surface differential pressure of the filtration membrane 600 to be less than or equal to 60 kilopascals, it is possible to perform the membrane separation processing while suppressing megakaryocytic cells from being divided (crushed) by the filtration membrane.

In a case of separating megakaryocytic cells from platelets using the filtration membrane 600, the thickness of the filtration membrane 600 is preferably less than or equal to 150 μm, more preferably less than or equal to 100 μm, and still more preferably less than or equal to 80 μm. By setting the thickness of the filtration membrane 600 to be less than or equal to 150 μm, the risk of clogging and the risk of damage to cells can be reduced by supplementing cells using the filtration membrane 600.

In the case of separating megakaryocytic cells from platelets using the filtration membrane 600, the gauge pressure applied to the supply side 604 of the filtration membrane 600 is preferably −70 kilopascals to 70 kilopascals, more preferably −40 kilopascals to 40 kilopascals, and still more preferably −20 kilopascals to 20 kilopascals. By setting the gauge pressure applied to the supply side 604 of the filtration membrane 600 to −70 kilopascals to 70 kilopascals, the risk of damage megakaryocytic cells can be reduced.

In the case of separating megakaryocytic cells from platelets using the filtration membrane 600, the diameters of the megakaryocytic cells as single cells are preferably 5 μm to 40 μm and more preferably 7 μm to 30 μm. The diameters of the platelets are preferably 1 μm to 5 μm and more preferably 2 μm to 4 μm.

In the case of separating megakaryocytic cells from platelets using the filtration membrane 600, the number density [cells/ml] of megakaryocytic cells which are contained in a filtrate that has permeated through the filtration membrane 600 is preferably less than or equal to 10% of the number density [cells/ml] of megakaryocytic cells contained in a cell suspension before permeating through the filtration membrane 600, more preferably less than or equal to 5% thereof, and still more preferably less than or equal to 1% thereof.

In the case of separating megakaryocytic cells from platelets using the filtration membrane 600, the number density [cells/ml] of platelets which are contained in a filtrate that has permeated through the filtration membrane 600 is preferably 50% to 100% of the number density [cells/ml] of platelets contained in a cell suspension before permeating through the filtration membrane 600, more preferably 80% to 100% thereof, and still more preferably 90% to 100% thereof.

In addition, when the amount of cell suspension in the cell culture container 610 in the cell culture device 2 shown in FIG. 17 is set to L and the amount of a filtrate that has permeated through the filtration membrane 600 per day in membrane separation processing is set to N, $0.1 \leq N/L \leq 6$ is preferably satisfied, $0.15 \leq N/L \leq 5$ is more preferably satisfied, and $0.2 \leq N/L \leq 4.5$ is still more satisfied. By satisfying $0.1 \leq N/L \leq 6$, platelets can be efficiently withdrawn from the cell suspension contained in the cell culture container 610, and the risk of damage to cells can be reduced.

Hereinafter, the present disclosure will be more specifically described with reference to examples and comparative examples. The material, the usage, the proportion, processing contents, a processing procedure, and the like shown in each example below can be appropriately changed without departing from the gist of the present invention. Accordingly, the scope of the present disclosure should not be interpreted restrictively by specific examples shown below.

EXAMPLE 1

Example 1 relates to a case of separating cell aggregations from single cells and debris by performing membrane separation processing on a cell suspension containing the cell aggregations, single cells and debris.

In the following, "M" represents a molar concentration relating to the substance concentration, and 1 M is 1 mol/L.

In the following, "PBS" means phosphate buffered saline and "IMDM" means an Iscove's modified Dulbecco's medium.

In the following, the "sphere" means a spherical cell aggregation.

<Materials>
[Human Induced Pluripotent Stem Cell Line (hiPS Cell Line)]
   253G1, Distributed from iPS PORTAL, Inc. (448-5 Kajii-cho, Imadegawa-Sagaru, Kawaramachi-dori, Kamigyo-ku, Kyoto, Japan)
[Base Medium and Medium Additive]
   TeSR-E8, model number ST-05940 of STEMCELL Technologies
   3% Methyl cellulose solution (in IMDM, methyl cellulose concentration is w/v %), model number HSC001 from R&D Systems 10 mM Y-27632 solution which is solution obtained by dissolving Y-27632 (ROCK inhibitor, model number Y0503 of Sigma-Aldrich) in Dulbecco's PBS (Ca- and Mg-free)
[Medium]
   A medium 1 was prepared such that 50 mL of a 3% methyl cellulose solution was added to 450 mL of TeSR-E8 and the mixture was thoroughly stirred. A 10 mM Y-27632 solution was added thereto in such an amount that the final concentration of Y-27632 became 10 μM.
   A medium 2 was prepared such that 50 mL of a 3% methyl cellulose solution was added to 450 mL of TeSR-E8, and the mixture was thoroughly stirred.
[Culture Dish and Centrifuge Tube]
   Ultra-Low Attachment Plate with 6 wells and lid, model number Costar 3471 of Corning
   15 mL Centrifuge tube, model number 339650 of Thermo Fisher Scientific Inc.

<Peeling from Plane and Production of Sphere>
The hiPS cell line 253G1 flat-cultured in a 70% confluent state was rinsed with Dulbecco's PBS (Ca- and Mg-free), and then peeled from the plane with a 0.5 M ethylenediamine tetraacetic acid (EDTA) solution. Subsequently, the medium was replaced with a medium 1. The cells were transferred to Ultra-Low Attachment Plate together with the medium and were allowed to stand in an incubator at 37° C. and at a $CO_2$ gas concentration of 5%.

After 1 to 2 days from the start of culture, the medium was replaced with a medium 2 to prepare 300 mL of a cell suspension containing spheres having diameters of 50 to 300 μm. The Ultra-Low Attachment Plate was taken out of the incubator and moved vertically and horizontally on the plane to uniformly disperse the spheres in wells. Thereafter, the cell suspension containing 300 mL of spheres was transferred to a 1 mL tube, 700 μl of TeSR-E8 was added thereto, centrifugation processing was performed at 4,000 rpm for 3 minutes, and a supernatant was removed. Subsequently, 300 μL of TrypLE Select (model number 12563 manufactured by Gibco) was added to the cell suspension, and the mixture was stirred with a vortex mixer. The mixture was stirred again with a vortex mixer after being left to stand for 3 minutes in an atmosphere of 37° C. FIG. 18A is a micrograph of the cell suspension obtained through the above-described processing. The number of cells of the cell suspension obtained through the above-described processing was measured with a NUCLEOCOUNTER (model number NC200 manufactured by ChemoMetec), and it was $1.5 \times 10^6$ cells/mL.

In addition, the viability of the cells was 92.2%.
<Membrane Separation Processing>
Membrane separation processing was performed on the cell suspension obtained through the above-described processing under each condition shown in Table 1. The membrane separation processing was performed using a sterilized filtration module forming a sealed space. A filtration membrane is disposed in the filtration module. The membrane separation processing was performed using a tangential flow method in which a cell suspension was allowed to flow along the surface of a filtration membrane from an inflow port to an outflow port of the filtration module.

A permeation side (filtrate side) of the filtration module was connected to a tube connector, and a syringe (model number SS50-LZ manufactured by TERUMO CORPORATION) was connected to the other end of the tube connector via a luer lock type tube connector. By controlling the suction speed of the syringe using a syringe pump (model number PHD-2000 manufactured by Harvard), the filtration flow rate was changed, thereby changing the membrane surface differential pressure of the filtration membrane. Filtration membranes having meshes and opening diameters shown in Table 1 were used. The opening diameters of the filtration membrane were obtained as particle diameters at which the blocking ratio becomes 95% (that is, a 95% separation particle diameter obtained from a particle permeation test) by performing the filtration test with standard particles.

<Differences Between Examples>

In each example, filtration membranes and the inter-membrane differential pressures were differentiated as shown in Table 1. Filtration membranes composed of twill weave meshes were used in Examples 1-1 to 1-9 and Reference Examples 1-1 and 1-2. A filtration membrane formed by laminating two plain weave meshes while deviating the positions of nets to each other was used in Example 1-10. Filtration membranes composed of one plain weave mesh were used in Comparative Examples 1-1 and 1-2. The material of the meshes used as filtration membranes in Examples 1-1 to 1-10, Comparative Examples 1-1 and 1-2, and Reference Examples 1-1 and 1-2 is SUS316 stainless steel.

<Measurement of Inter-Membrane Differential Pressure>

A pressure M1 of the inflow port of the filtration module, a pressure M2 of the outflow port, and a pressure M3 on the permeation side (filtrate side) are measured using a pressure sensor (model number ACPM49903N manufactured by SPECTRUM), and a membrane surface differential pressure ΔM of the filtration membrane was calculated using Equation (1).

phase contrast microscope (model number IX73 manufactured by Olympus Corporation) at a magnification of 10 times. The filtration area was 50 cm$^2$.

The results of comprehensive determination in a case where the membrane separation processing is performed according to each condition is shown in Table 1. The determination criteria for the comprehensive determination A, B, C, and D were set as follows. In Table 1, MESH means the net number in 24.5 mm (1 inch) of wefts of a mesh forming a filtration membrane. In Table 1, a maximum inter-membrane differential pressure means a maximum value of inter-membrane differential pressures of a filtration membrane during membrane separation processing.

A: The shapes of spheres after the membrane separation processing are kept, and no deformed cells are seen on the filtration membrane. There is debris on the permeation side (filtrate side), but there are no divided spheres thereon.

B: The shapes of spheres after the membrane separation processing are kept, but there are deformed spheres on the filtration membrane. There is debris on the permeation side (filtrate side), but there are no divided spheres thereon.

C: The shapes of spheres after the membrane separation processing are kept, but there are deformed spheres on the filtration membrane. There are some divided spheres on the permeation side (filtrate side).

D: The shapes of spheres after the membrane separation processing are collapsed, and there are many divided spheres on the permeation side (filtrate side).

TABLE 1

| | Average diameter [μm] of cell aggregations | Filtration membrane | | | | | Maximum inter-membrane differential pressure [kPa] | Determination |
| | | Weaving method | Net | | Thread diameter [μm]: warp/weft | 95% Separation particle diameter [μm] | | |
| | | | MESH | Length × width | | | | |
|---|---|---|---|---|---|---|---|---|
| Example 1-1 | 175 | Twill weave | 2600 MESH | 350 × 2600 | 30/22 | 5 | 13.8 | A |
| Example 1-2 | 175 | Twill weave | 2000 MESH | 200 × 2000 | 50/28 | 12 | 13.8 | A |
| Example 1-3 | 175 | Twill weave | 1400 MESH | 165 × 1400 | 65/40 | 15 | 6.9 | A |
| Example 1-4 | 175 | Twill weave | 1000 MESH | 120 × 1000 | 65/53 | 20 | 6.9 | A |
| Example 1-5 | 175 | Twill weave | 700 MESH | 80 × 700 | 100/65 | 30 | 6.9 | A |
| Example 1-6 | 175 | Twill weave | 500 MESH | 32 × 500 | 180/110 | 50 | 6.9 | B |
| Example 1-7 | 175 | Twill weave | 300 MESH | 30 × 300 | 260/190 | 80 | 6.9 | B |
| Example 1-8 | 175 | Twill weave | 200 MESH | 20 × 200 | 350/280 | 115 | 6.9 | B |
| Example 1-9 | 175 | Twill weave | 2600 MESH | 350 × 2600 | 30/22 | 5 | 68.9 | C |
| Example 1-10 | 175 | Plain weave × 2 sheets | — | — | 5 | 37 | — | 68.9 | B |
| Comparative Example 1-1 | 175 | Plain weave × 1 sheet | — | — | 5 | 37 | — | 13.8 | C |
| Comparative Example 1-2 | 175 | Plain weave × 1 sheet | — | — | 5 | 37 | — | 68.9 | D |
| Reference Example 1-1 | 175 | Twill weave | 4300 MESH | 635 × 4300 | 20/13 | 2 | 74.5 | D |
| Reference Example 1-2 | 175 | Twill weave | 3500 MESH | 500 × 3500 | 25/15 | 4 | 41.4 | D |

<Measurement of Cell Diameter>

The cell suspension before the membrane separation processing was collected and the mean diameter of cells was determined using Vi-CELL of BECKMAN COULTER.

<Determination of Membrane Separation Processing>

A concentrated liquid obtained through the membrane separation processing, the filtrate discharged to the permeation side, and the surface of the filtration membrane after the membrane separation processing are observed using a As shown in Table 1, in a case (Examples 1-1 to 1-8) where a twill weave mesh was used as a filtration membrane and a case (Example 1-10) where a filtration membrane obtained by laminating two plain weave meshes while deviating the positions of nets to each other was used, favorable comprehensive determination results were obtained. In addition, it was confirmed that, in the case where a twill weave mesh was used as a filtration membrane, the ranges of the net size and the inter-membrane differential pressure of the filtration membrane from which the comprehensive determination A or B can be obtained become wide.

Figure 18B:
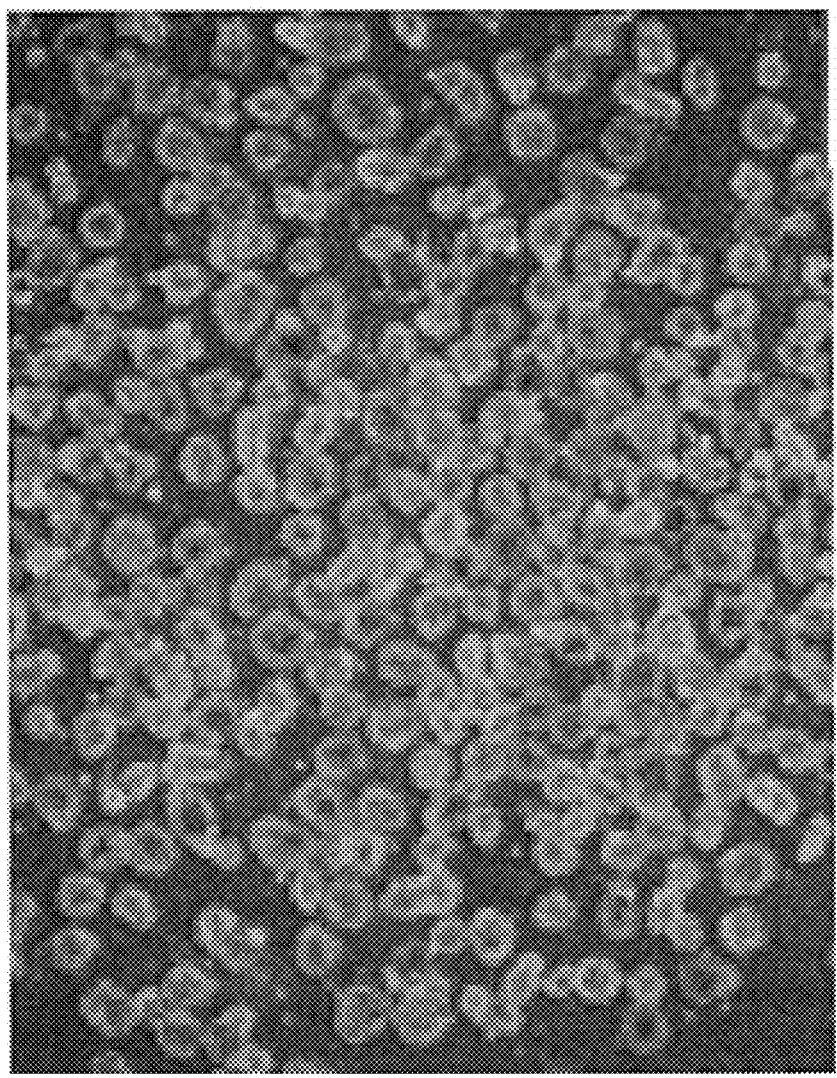
FIG. 18B is a micrograph of a cell suspension after membrane separation processing is performed under a condition of Example 1-1 in Table 1.

FIG. 18A is a micrograph of a cell suspension before membrane separation processing. FIG. 18B is a micrograph of a cell suspension after membrane separation processing is performed under a condition of Example 1-1 in Table 1. The cell suspension is concentrated and debris is removed. FIG. 18C is a micrograph of a filtrate discharged to a permeation side after membrane separation processing is performed under the condition of Example 1-1 in Table 1. There is debris in the filtrate, but there are no divided spheres therein. FIG. 18D is a micrograph of a filtrate discharged to a permeation side after membrane separation processing is performed under a condition of Comparative Example 1-1 in Table 1. There are many divided spheres in the filtrate.

EXAMPLE 2

Example 2 relates to a case of separating single cells from debris by performing membrane separation processing on a cell suspension containing the single cells and debris.

<Preparation of Single Cells>

According to the procedure described in Example 1, 50 g of a cell suspension containing spheres having a diameter of about 300 μm prepared from a hiPS cell line 253G1 was subjected to centrifugation for 2 minutes, and a supernatant was removed. Thereafter, TrypLE Select (model number 12563 manufactured by GIBCO) was added thereto, the mixture was stirred with a vortex mixer, and allowed to stand in an atmosphere of 37° C. for 3 minutes. Then, the mixture was stirred with a vortex mixer again to prepare a cell suspension containing single cells. The number of cells was adjusted by changing the amount of culture media TrypLE Select and TeSR-E8.

<Membrane Separation Processing>

Membrane separation processing was performed on the cell suspension obtained through the above-described processing under each condition shown in Table 2. The membrane separation processing was performed using a sterilized filtration module forming a sealed space. A filtration membrane is disposed in the filtration module. The membrane separation processing was performed using a tangential flow method in which a cell suspension was allowed to flow along the surface of a filtration membrane from an inflow port to an outflow port of the filtration module.

A permeation side (filtrate side) of the filtration module was connected to a tube connector, and a syringe (model number SS50-LZ manufactured by TERUMO CORPORATION) was connected to the other end of the tube connector via a luer lock type tube connector. By controlling the suction speed of the syringe using a syringe pump (model number PHD-2000 manufactured by Harvard), the filtration flow rate was changed, thereby changing the membrane surface differential pressure of the filtration membrane.

Filtration membranes having meshes, opening diameters, and opening diameter distributions (coefficients of variation σ/X) shown in Table 2 were used. The opening diameters of the filtration membrane were obtained as particle diameters at which the blocking ratio becomes 95% (that is, a 95% separation particle diameter obtained from a particle permeation test) by performing the filtration test with standard particles. The opening diameter distributions (coefficients of variation σ/X) of the filtration membranes were measured through a mercury intrusion method, and an average value X and a standard deviation σ were obtained through a well-known statistical analysis method.

<Differences Between Examples>

In each example, filtration membranes and the inter-membrane differential pressures were differentiated as shown in Table 1. Filtration membranes composed of twill weave meshes were used in Examples 2-1 and 2-2 and Reference Examples 2-1 and 2-2. A filtration membrane formed by laminating two plain weave meshes while deviating the positions of nets to each other was used in Example 2-3. Filtration membranes composed of one plain weave mesh were used in Comparative Examples 2-1 and 2-2. The material of the meshes used as filtration membranes in Examples 2-1 to 2-3, Comparative Examples 2-1 and 2-2, and Reference Examples 2-1 and 2-2 is SUS316 stainless steel.

<Measurement of Inter-Membrane Differential Pressure>

A pressure M1 of the inflow port of the filtration module, a pressure M2 of the outflow port, and a pressure M3 on the permeation side (filtrate side) are measured using a pressure sensor (model number ACPM49903N manufactured by SPECTRUM), and a membrane surface differential pressure ΔM of the filtration membrane was calculated using Equation (1).

<Measurement of Cell Diameter>

The cell suspension before the membrane separation processing was collected and the mean diameter of cells was determined using Vi-CELL of BECKMAN COULTER.

<Determination of Membrane Separation Processing>

A concentrated liquid obtained through the membrane separation processing, the filtrate discharged to the permeation side, and the surface of the filtration membrane after the membrane separation processing are observed using a phase contrast microscope (model number IX73 manufactured by Olympus Corporation) at a magnification of 10 times. The filtration area was 50 cm².

The results of comprehensive determination in a case where the membrane separation processing is performed according to each condition are shown in Table 2. The determination criteria for the comprehensive determination A, B, and C were set as follows.

A: The shapes of single cells after the membrane separation processing are maintained. There is debris on the permeation side (filtrate side), but there is no single cell discharged to the permeation side (filtrate side).

B: The shapes of single cells after the membrane separation processing are maintained, and debris and slight single cells are seen on the permeation side (filtrate side).

C: Debris and numerous single cells are seen on the permeation side (filtrate side).

TABLE 2

| | Average value of cell diameters [μm] | Filtration membrane | | | | | | Maximum inter-membrane differential pressure [kPa] | Deter-mination |
|---|---|---|---|---|---|---|---|---|---|
| | | Weaving method | Net | | Thread diameter [μm]: warp/weft | 95% Separation particle diameter [μm] | Coefficients of variation σ/X | | |
| | | | MESH | Length × width | | | | | |
| Example 2-1 | 15 | Twill weave | 4300 MESH | 635 × 4300 | 20/13 | 2 | 0.019 | 5.3 | A |
| Example 2-2 | 15 | Twill weave | 3500 MESH | 500 × 3500 | 25/15 | 4 | 0.011 | 5.3 | B |
| Example 2-3 | 15 | Plain weave × 2 sheets | — | 5 | 37 | — | 0.087 | 5.3 | B |
| Comparative Example 2-1 | 15 | Plain weave × 1 sheet | — | 5 | 37 | — | 0.031 | 5.3 | C |
| Comparative Example 2-2 | 15 | Plain weave × 1 sheet | — | 5 | 37 | — | 0.031 | 68.9 | C |
| Reference Example 2-1 | 15 | Twill weave | 2000 MESH | 200 × 2000 | 50/28 | 12 | 0.008 | 2.4 | C |
| Reference Example 2-2 | 15 | Twill weave | 1000 MESH | 120 × 1000 | 65/53 | 20 | 0.009 | 1.6 | C |

As shown in Table 2, in a case (Examples 2-1 and 2-2) where a twill weave mesh was used as a filtration membrane and a case (Example 2-3) where a filtration membrane obtained by laminating two plain weave meshes while deviating the positions of nets to each other was used, favorable comprehensive determination results were obtained.

EXAMPLE 3

Example 3 relates to a case of separating non-human cells from debris by performing membrane separation processing on a cell suspension containing the non-human cells as single cells and the debris.
<Materials>
Cells: Chinese hamster ovary (CHO) cells were used.
Medium: Serum-free medium (CD Opti CHO AGT Medium of Life technologies) was used as a medium.
<Batch Culture of Cells>
Cells were seeded in a culture container in which 1 L of culture medium is placed, and the cell concentration was adjusted so as to become $5 \times 10^5$ cells/ml. Subsequently, batch culture was performed in a culture container at 37° C., a stirring speed of 100 rpm of a stirrer, an AIR flow rate of 47.5 ml/min, an $O_2$ flow rate of 8 ml/min, and a $CO_2$ flow rate of 2.5 ml/min for 5 days. The cell concentration after 5 days was $1 \times 10^7$ cells/ml and the viability of the cells was 95%.
<Filtration/Perfusion Culture>
Next, membrane separation processing was performed using a filtration module of which one circulation port on a supply side is connected to a culture container via a tube and the other circulation port is connected to a reciprocatable diaphragm pump (ATF2system of Refine Technology) via a tube. The diaphragm pump was operated to supply a cell suspension in the culture container into the filtration module. The diaphragm pump was set so as to repeat the reciprocation every 5 seconds at a flow rate of 1 L/min, so that the cell suspension was allowed to flow alternately in parallel to the filtration membrane. Filtration membranes having meshes, opening diameters, opening diameter distributions (coefficients of variation σ/X), and membrane thicknesses shown in Table 3 were used. The opening diameters of the filtration membrane were obtained as particle diameters at which the blocking ratio becomes 95% (that is, a 95% separation particle diameter obtained from a particle permeation test) by performing the filtration test with standard particles. The opening diameter distributions (coefficients of variation σ/X) of the filtration membranes were measured through a mercury intrusion method, and an average value X and a standard deviation σ were obtained through a well-known statistical analysis method. The membrane thicknesses of the filtration membranes were obtained using a contact type membrane thickness meter (manufactured by Anritsu).

A filtrate was withdrawn from a discharge port on the permeation side of the filtration module connected to a collection tank of debris and antibodies via a tube using a tube pump (MASTER FLEX TUBE PUMP of Cole Parmer). The filtration conditions were set so that N/L became 1 when the total liquid amount of a cell suspension in a culture container was set to L and the withdrawal flow rate of filtrate per day was set to N. In addition, a medium was supplied from a medium supply tank internally connected to the culture container via a tube using a tube pump (MASTER FLEX TUBE PUMP of Cole Parmer) at the same flow rate as that of the withdrawal liquid amount of the filtrate so that the amount of cell suspension in the culture container becomes constant.
<Differences Between Examples>
In each example, cell types, filtration membranes, filtration conditions, and pressures (adjusted according to filtration conditions) were differentiated as shown in Table 3. Filtration membranes composed of twill weave meshes were used in Examples 3-1 to 3-8 and Examples 3-11 to 3-18. Filtration membranes formed by laminating two plain weave meshes while deviating the positions of nets to each other were used in Examples 3-9 and 3-10. A filtration membrane composed of one plain weave mesh was used in Comparative Example 3-1. A filtration membrane composed of a microfiltration (MF) membrane was used in Comparative Example 3-2. A filtration membrane composed of a sintered porous filter was used in Comparative Examples 3-3. A filtration membrane composed of a ceramic filter was used in Comparative Example 3-4. The material of the meshes used as filtration membranes in Examples 3-1 to 3-18 and Comparative Example 3-1 is SUS316 stainless steel.

<Measurement>

After filtration/perfusion culture was performed for 1 day, the following measurements were performed.

<Measurement of Pressure>

A pressure M1 of the circulation port provided on the diaphragm pump on the supply side of the filtration module, a pressure M2 of the circulation port provided on the culture container on the supply side of the filtration module, and a pressure M3 on the permeation side of the filtration module were measured. The pressure was measured with a digital pressure monitor KrosFlo of Spectrum Laboratories. The membrane surface differential pressure ΔM of the filtration membrane was calculated using Equation (1).

<Measurement of Cell Diameter>

A cell suspension was collected from the culture container and the average diameter of cells was obtained using Vi-CELL of BECKMAN COULTER.

<Number Concentration and Viability of Cells>

A cell suspension was collected from the culture container, a filtrate was collected from the permeation side of the filtration module, and the number concentration and viability of living cells were respectively obtained using Vi-CELL of BECKMAN COULTER.

<Number Concentration of Debris>

A cell suspension was collected from the culture container, a filtrate was collected from the filtrate side of the filtration module, and the number concentration of the debris was obtained using Multisizer 4 of BECKMAN COULTER. The debris had a diameter of 1/10 to 1/2 of the average diameter of the cells.

<Determination of Filtration>

Evaluation was made based on the following criteria as a comprehensive determination on filtration.

A: The ratio of the number density of cells on the permeation side (filtrate side) to the supply side is less than or equal to 5%, the ratio of the number density of debris on the permeation side (filtrate side) to the supply side is greater than or equal to 80%, and the viability of cells is greater than or equal to 90%

B: The ratio of the number density of cells on the permeation side (filtrate side) to the supply side is less than or equal to 20%, the ratio of the number density of debris on the permeation side (filtrate side) to the supply side is greater than or equal to 70%, and the viability of cells is greater than or equal to 80%

C: The ratio of the number density of cells on the permeation side (filtrate side) to the supply side is less than or equal to 50%, the ratio of the number density of debris on the permeation side (filtrate side) to the supply side is greater than or equal to 50%, and the viability of cells is greater than or equal to 70%

D: The ratio of the number density of cells on the permeation side (filtrate side) to the supply side exceeds 50%, the ratio of the number density of debris on the permeation side (filtrate side) to the supply side is less than 50%, or the viability of cells is less than 70%

TABLE 3

| | Cell | | Filtration membrane | | | | | | Opening diameter | |
| --- | --- | --- | --- | --- | --- | --- | --- | --- | --- | --- |
| | Type | Average value of cell diameters [μm] | Weaving method | Hydrophilic processing | Net MESH | Net Length × width | Thread diameter [μm]: warp/weft | Membrane thickness [μm] | Ratio with cell diameter | 95% Separation particle diameter [μm] |
| Example 3-1 | CHO cell 1 | 14 | Twill weave | None | 3500 | 500 × 3500 | 25/15 | 55 | 0.29 | 4 |
| Example 3-2 | CHO cell 1 | 14 | Twill weave | None | 2600 | 350 × 2600 | 30/20 | 80 | 0.36 | 5 |
| Example 3-3 | CHO cell 1 | 14 | Twill weave | None | 2000 | 200 × 2000 | 50/28 | 110 | 0.86 | 12 |
| Example 3-4 | CHO cell 1 | 14 | Twill weave | None | 1000 | 120 × 1000 | 65/53 | 180 | 1.43 | 20 |
| Example 3-5 | CHO cell 2 | 8 | Twill weave | None | 1000 | 120 × 1000 | 65/53 | 180 | 2.50 | 20 |
| Example 3-6 | CHO cell 1 | 14 | Twill weave | None | 4300 | 635 × 4300 | 20/13 | 40 | 0.14 | 2 |
| Example 3-7 | CHO cell 3 | 22 | Twill weave | None | 4300 | 635 × 4300 | 20/13 | 40 | 0.09 | 2 |
| Example 3-8 | CHO cell 1 | 14 | Twill weave | Done | 3500 | 500 × 3500 | 25/15 | 55 | 0.29 | 4 |
| Example 3-9 | CHO cell 1 | 14 | Plain weave × 2 sheets | None | — | — | — | 120 | 0.36 | 5 |
| Example 3-10 | CHO cell 1 | 14 | Plain weave × 2 sheets | None | — | — | — | 160 | 0.43 | 6 |
| Example 3-11 | CHO cell 1 | 14 | Twill weave | None | 3500 | 500 × 3500 | 25/15 | 55 | 0.29 | 4 |
| Example 3-12 | CHO cell 1 | 14 | Twill weave | None | 3500 | 500 × 3500 | 25/15 | 55 | 0.29 | 4 |
| Example 3-13 | CHO cell 1 | 14 | Twill weave | None | 3500 | 500 × 3500 | 25/15 | 55 | 0.29 | 4 |
| Example 3-14 | CHO cell 1 | 14 | Twill weave | None | 3500 | 500 × 3500 | 25/15 | 55 | 0.29 | 4 |
| Example 3-15 | CHO cell 1 | 14 | Twill weave | None | 3500 | 500 × 3500 | 25/15 | 55 | 0.29 | 4 |

TABLE 3-continued

|  |  |  |  |  |  |  |  |  |  |  |
|---|---|---|---|---|---|---|---|---|---|---|
| Example 3-16 | CHO cell 1 | 14 | Twill weave | None | 3500 | 500 × 3500 | 25/15 | 55 | 0.29 | 4 |
| Example 3-17 | CHO cell 1 | 14 | Twill weave | None | 3500 | 500 × 3500 | 25/15 | 55 | 0.29 | 4 |
| Example 3-18 | BHK cell | 12 | Twill weave | None | 3500 | 500 × 3500 | 25/15 | 55 | 0.33 | 4 |
| Comparative Example 3-1 | CHO cell 1 | 14 | Plain weave × 1 sheet | None | — | — | — | 60 | 0.36 | 5 |
| Comparative Example 3-2 | CHO cell 1 | 14 | MF membrane | None | — | — | — | 160 | 0.01 | 0.2 |
| Comparative Example 3-3 | CHO cell 1 | 14 | Sintered porous filter | None | — | — | — | 1500 | 0.71 | 10 |
| Comparative Example 3-4 | CHO cell 1 | 14 | Ceramic filter | None | — | — | — | 1500 | 0.71 | 10 |

|  | Filtration membrane Opening diameter Co-efficients of variation $\sigma/X$ | Filtration condition N/L [day] | Pressure | | Inter-membrane differential pressure [kPa] | Evaluation result | | | |
|---|---|---|---|---|---|---|---|---|---|
|  |  |  | Gauge pressure on supply side | | | Number density ratio of cells: supply side/ permeation side [%] | Number density ratio of debris: permeation side/ supply side [%] | Cell viability [%] | Comprehensive determination |
|  |  |  | Minimum pressure [kPa] | Maximum pressure [kPa] |  |  |  |  |  |
| Example 3-1 | 0.01 | 1 | −7 | 8 | 0.5 | 1 | 96 | 95 | A |
| Example 3-2 | 0.01 | 1 | −6 | 7 | 0.3 | 5 | 98 | 92 | A |
| Example 3-3 | 0.01 | 1 | −7 | 7 | 0.16 | 14 | 100 | 89 | B |
| Example 3-4 | 0.01 | 1 | −5 | 6 | 0.05 | 32 | 100 | 80 | C |
| Example 3-5 | 0.01 | 1 | −4 | 5 | 0.02 | 47 | 100 | 72 | C |
| Example 3-6 | 0.02 | 1 | −9 | 9 | 4 | 1 | 77 | 94 | B |
| Example 3-7 | 0.02 | 1 | −7 | 9 | 11 | 1 | 60 | 94 | C |
| Example 3-8 | 0.01 | 1 | −7 | 8 | 1.1 | 3 | 94 | 88 | B |
| Example 3-9 | 0.09 | 1 | −6 | 8 | 0.13 | 11 | 81 | 87 | B |
| Example 3-10 | 0.13 | 1 | −7 | 8 | 0.12 | 23 | 79 | 78 | C |
| Example 3-11 | 0.01 | 1 | −36 | 37 | 21 | 19 | 99 | 82 | B |
| Example 3-12 | 0.01 | 1 | −72 | 72 | 64 | 34 | 100 | 62 | C |
| Example 3-13 | 0.01 | 3 | −17 | 8 | 5 | 4 | 97 | 92 | A |
| Example 3-14 | 0.01 | 5 | −22 | 7 | 22 | 11 | 98 | 85 | B |
| Example 3-15 | 0.01 | 6.5 | −38 | 6 | 31 | 27 | 99 | 78 | C |
| Example 3-16 | 0.01 | 0.15 | −6 | 7 | 0.4 | 1 | 98 | 88 | B |
| Example 3-17 | 0.01 | 0.04 | −5 | 6 | 0.2 | 1 | 98 | 79 | C |
| Example 3-18 | 0.01 | 1 | −7 | 8 | 0.14 | 6 | 96 | 95 | A |
| Comparative Example 3-1 | 0.03 | 1 | −7 | 8 | 0.14 | 69 | 99 | 44 | D |
| Comparative Example 3-2 | 0.25 | 1 | −18 | 19 | 17 | 1 | 1 | 91 | D |

TABLE 3-continued

| | | | | | | | | | |
|---|---|---|---|---|---|---|---|---|---|
| Comparative Example 3-3 | 0.12 | 1 | −6 | 7 | 0.7 | 72 | 95 | 40 | D |
| Comparative Example 3-4 | 0.06 | 1 | −22 | 21 | 16 | 13 | 91 | 22 | D |

As shown in Table 3, it is possible to obtain favorable comprehensive determination results in Examples 3-1 to 3-18 compared to Comparative Examples 3-1 to 3-4.

EXAMPLE 4

Example 4 relates to a case of separating human megakaryocytes from human platelets by performing membrane separation processing on a cell suspension containing the human megakaryocytes as single cells and the human platelets as debris.

<Materials>

Medium: a medium obtained by adding 50 ml of *bovine* serum (Life Technologies) to 450 ml of RPMI 1640 (Life Technologies) was used.

Megakaryocyte: MEG-01 (ATCC) was used as a megakaryocyte. This was mixed with the medium to prepare a cell suspension ($6 \times 10^5$ cells/ml).

Platelets: Platelets isolated from rat peripheral blood were used as platelets. 10 ml of whole blood collected from rats was collected in a 15 ml conical tube for centrifugation (Falcon) containing citric acid-dextrose solution (ACD) (sigma-aldrich). The whole blood was centrifuged at 300×g at room temperature for 7 minutes, and a plasma layer and a buffy coat layer after centrifugation were collected. The collected liquid was subjected to centrifugation in the same manner and only a plasma layer was collected. Thereafter, the plasma layer was centrifuged at 1800×g at room temperature for 5 minutes, and a supernatant was collected to obtain platelets. The platelets were mixed with the medium to prepare a cell suspension ($6 \times 10^7$ cells/ml).

By mixing the megakaryocyte liquid with the platelet liquid in an equal amount, the mixture was used as a cell suspension for cell separation test.

<Cell Filtration Test>

Membrane separation processing was performed using a filtration module (KS-47 of ADVANTEC) in which one circulation port on a supply side of the filtration module is connected to a syringe (TERUMO CORPORATION) containing a cell suspension via a tube. The syringe was installed in a syringe pump (PHD ULTRA 4400 of HARVARD APPARATUS) which was operated so that the cell suspension was supplied to a filtration membrane in the filtration module at a flow rate of 1 ml/min in a dead-end method orthogonal to the filtration membrane. A filtrate discharged from a discharge port on a permeation side of the filtration module was collected.

Filtration membranes having meshes, opening diameters, opening diameter distributions (coefficients of variation σ/X), and membrane thicknesses shown in Table 4 were used. The opening diameters of the filtration membrane were obtained as particle diameters at which the blocking ratio becomes 95% (that is, a 95% separation particle diameter obtained from a particle permeation test) by performing the filtration test with standard particles. The opening diameter distributions (coefficients of variation σ/X) of the filtration membranes were measured through a mercury intrusion method, and an average value X and a standard deviation σ were obtained through a well-known statistical analysis method. The membrane thicknesses of the filtration membranes were obtained using a contact type membrane thickness meter (manufactured by Anritsu).

<Differences Between Examples>

In each example, filtration membranes were differentiated as shown in Table 4. Filtration membranes composed of twill weave meshes were used in Examples 4-1 to 4-3. Filtration membranes composed of one plain weave mesh were used in Comparative Examples 4-1 to 4-4. The material of the meshes used as filtration membranes is SUS316 stainless steel.

<Measurement>

After collecting a filtrate, the following measurements were performed.

<Number Concentration of Megakaryocytes>

A filtrate was collected from the permeation side of the filtration module and the concentration of megakaryocytes was obtained using Vi-CELL of BECKMAN COULTER. The blocking ratio of the megakaryocytes obtained from the following equation was obtained. Blocking ratio (%) of megakaryocytes=100−(concentration of megakaryocytes in filtrate/concentration of megakaryocytes in source liquid)×100

<Number Concentration of Platelets>

A filtrate was collected from the permeation side of the filtration module and the concentration of platelets was obtained using XT-2000iv of Sysmex Corporation. The permeability of platelets obtained from the following equation was obtained. Permeability (%) of platelets=(concentration of platelets in filtrate/concentration of platelets in original liquid)×100

<Determination of Filtration>

Evaluation was made based on the following criteria as a comprehensive determination on filtration.

A: The blocking ratio of megakaryocytes is less than 5% and the permeability of platelets is greater than or equal to 90%

B: The blocking ratio of megakaryocytes is less than 10% and the permeability of platelets is greater than or equal to 90%

C: The blocking ratio of megakaryocytes is greater than or equal to 10% or the permeability of platelets is less than 90%

TABLE 4

| | Average value of cell diameters [μm] | Weaving method | Net MESH | Net Length × width | Thread diameter [μm]: warp/weft | Membrane thickness [μm] | Ratio with cell diameter | Opening diameter 95% Separation particle diameter [μm] | Coefficients of variation σ/X | Evaluation result Blocking ratio [%] of megakaryocytes | Permeability [%] of platelets | Comprehensive determination |
|---|---|---|---|---|---|---|---|---|---|---|---|---|
| Example 4-1 | 15 | Twill weave | 4300 | 635 × 4300 | 20/13 | 53 | 0.14 | 2 | 0.019 | 1 | 95 | A |
| Example 4-2 | 15 | Twill weave | 3400 | 450 × 3400 | 25/16 | 66 | 0.29 | 4 | 0.011 | 1 | 96 | A |
| Example 4-3 | 15 | Twill weave | 3000 | 400 × 3000 | 30/18 | 55 | 0.32 | 4.5 | 0.01 | 5 | 94 | B |
| Comparative Example 4-1 | 15 | Plain weave | — | — | — | 50 | 0.34 | 4.8 | 0.02 | 42 | 92 | C |
| Comparative Example 4-2 | 15 | Plain weave | — | — | — | 60 | 0.36 | 5 | 0.03 | 86 | 87 | C |
| Comparative Example 4-3 | 15 | Plain weave | — | — | — | 50 | 0.34 | 4.8 | 0.02 | 36 | 90 | C |
| Comparative Example 4-4 | 15 | Plain weave | — | — | — | 60 | 0.36 | 5 | 0.03 | 93 | 91 | C |

As shown in Table 4, it is possible to obtain favorable comprehensive determination results in Examples 4-1 to 4-3 compared to Comparative Examples 4-1 to 4-4.

The entire disclosure of JP2016-130579 and JP2017-095673 is incorporated herein by reference.

All documents, patent applications, and technical standards described herein are incorporated herein by reference to the same extent as a case in which incorporation of an individual document, patent application, and technical standard by reference is specifically and individually written.

What is claimed is:

1. A membrane separation method of a cell suspension comprising:
   providing a filtration membrane which includes an inlet-side opening formed on a first surface and an outlet-side opening, which is formed on a second surface on an opposite side of the first surface and communicates with the inlet-side opening, and in which the inlet-side opening and the outlet-side opening are disposed at positions deviated in a direction parallel to the first and second surfaces of the filtration membrane; and
   performing membrane separation processing of the cell suspension;
   wherein the filtration membrane is a component within a filtration device comprising a single chamber that comprises an inflow port through which the cell suspension flows to enter the filtration device and an outflow port through which the cell suspension flows to exit the filtration device,
   wherein as the cell suspension flows between the inflow port and the outflow port, the cell suspension flows along a direction of the first and second surfaces of the filtration membrane,
   wherein the single chamber further comprises a discharge port that discharges from the chamber a portion of the cell suspension that has passed through the filtration membrane, the discharge port being disposed at one side of the filtration membrane, and the inflow port and outflow port being disposed at another side of the filtration membrane, and
   wherein the filtration membrane comprises a mesh formed by twill-weaving a fibrous membrane.

2. The membrane separation method according to claim 1,
   wherein the cell suspension contains a cell aggregation, a single cell, and debris, and
   wherein the cell aggregation is separated from the single cell and the debris using the filtration membrane in the membrane separation processing.

3. The membrane separation method according to claim 2, wherein a diameter of the inlet-side opening of the filtration membrane is 0.01 to 3.0 times a diameter of the cell aggregation.

4. The membrane separation method according to claim 2, wherein the cell aggregation is an aggregation of human-derived cells, and the single cell is a human-derived cell.

5. The membrane separation method according to claim 1,
   wherein the cell suspension contains a single cell and debris, and
   wherein the single cell is separated from the debris using the filtration membrane in the membrane separation processing.

6. The membrane separation method according to claim 5,
   wherein the single cell is a human-derived cell, and
   wherein a diameter of the inlet-side opening of the filtration membrane is 0.05 to 0.8 times a diameter of the single cell.

7. The membrane separation method according to claim 6, wherein the human-derived cell is a stem cell.

8. The membrane separation method according to claim 5, wherein the single cell is a non-human cell, and
wherein a diameter of the inlet-side opening of the filtration membrane is 0.1 to 2 times a diameter of the single cell.

9. The membrane separation method according to claim 5, wherein the single cell is a non-human cell, and
wherein $0<\sigma/X\leq0.1$ is satisfied, where an average value of opening diameter distribution of the filtration membrane is set to X and a standard deviation is set to $\sigma$.

10. The membrane separation method according to claim 5,
wherein the single cell is a non-human cell, and
wherein a thickness of the filtration membrane is less than or equal to 150 µm.

11. The membrane separation method according to claim 5,
wherein the single cell is a non-human cell, and
wherein a gauge pressure applied to the first surface of the filtration membrane is −70 kilopascals to 70 kilopascals.

12. The membrane separation method according to claim 5,
wherein the single cell is a non-human cell, and
wherein a number density of the single cell contained in a filtrate that has permeated through the filtration membrane is less than or equal to 50% of a number density of the single cell contained in the cell suspension before permeating through the filtration membrane.

13. The membrane separation method according to claim 5,
wherein the single cell is a non-human cell, and
wherein a number density of debris which has a diameter of 1/10 to 1/2 of the diameter of the single cell and is contained in the filtrate that has permeated through the filtration membrane is 50% to 100% of a number density of debris which has a diameter of 1/10 to 1/2 of the diameter of the single cell and is contained in the cell suspension before permeating through the filtration membrane.

14. The membrane separation method according to claim 5,
wherein the single cell is a non-human cell, and
wherein the diameter of the single cell is 5 µm to 25 µm.

15. The membrane separation method according to claim 5, wherein the single cell is a CHO cell.

16. The membrane separation method according to claim 5, wherein the single cell is a human-derived cell.

17. The membrane separation method according to claim 16, wherein the human-derived cell is a stem cell.

18. The membrane separation method according to claim 16, wherein the human-derived cell is a megakaryocyte.

19. The membrane separation method according to claim 1, wherein the membrane separation processing is performed by setting a difference between a pressure applied to the first surface of the filtration membrane and a pressure applied to the second surface of the filtration membrane to 0.01 kilopascals to 60 kilopascals.

20. The membrane separation method according to claim 1, wherein the membrane separation processing is performed using the filtration membrane whose surfaces have been subjected to hydrophilic treatment.

21. The membrane separation method according to claim 1, wherein the filtration membrane is configured by laminating a plurality of meshes, each of which has through-holes, while deviating the positions of the through-holes to each other in a direction parallel to the first and second surfaces of the filtration membrane.

22. The membrane separation method according to claim 21, wherein the meshes are made of metal.

23. The membrane separation method according to claim 1, wherein the membrane separation processing is performed by reciprocating the cell suspension along the first and second surfaces of the filtration membrane.

24. A membrane separation method for performing membrane separation processing of a cell suspension comprising:
providing a culture container for culturing cells, and
using a filtration membrane, in which an inlet-side opening formed on a first surface and an outlet-side opening which is formed on a second surface on an opposite side of the first surface and communicates with the inlet-side opening are disposed at positions deviated in a direction parallel to the first and second surfaces of the filtration membrane, of a cell culture device including the culture container and a filtration portion which includes the filtration membrane and is connected to the culture container via a flow path in which cells cultured in the culture container circulate,
wherein $0.1\leq N/L\leq6$ is satisfied when the amount of the cell suspension in the culture container is set to L and the amount of a filtrate per day that has permeated through the filtration membrane in the membrane separation processing is set to N,
wherein the filtration portion comprises an inflow port through which the cell suspension flows to enter the filtration portion and an outflow port through which the cell suspension flows to exit the filtration portion,
wherein as the cell suspension flows between the inflow port and the outflow port, the cell suspension flows along a direction of the first and second surfaces of the filtration membrane, and
wherein the filtration membrane comprises a mesh formed by twill-weaving a fibrous membrane.

* * * * *